(12) United States Patent
Horiguchi et al.

(10) Patent No.: US 10,927,087 B2
(45) Date of Patent: Feb. 23, 2021

(54) METHOD FOR PRODUCING POLYMERIZABLE COMPOUND

(71) Applicant: DIC Corporation, Tokyo (JP)

(72) Inventors: Masahiro Horiguchi, Kita-adachi-gun (JP); Junichi Mamiya, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 59 days.

(21) Appl. No.: 15/781,950

(22) PCT Filed: Nov. 29, 2016

(86) PCT No.: PCT/JP2016/085300
§ 371 (c)(1),
(2) Date: Jun. 6, 2018

(87) PCT Pub. No.: WO2017/098952
PCT Pub. Date: Jun. 15, 2017

(65) Prior Publication Data
US 2018/0354922 A1 Dec. 13, 2018

(30) Foreign Application Priority Data
Dec. 7, 2015 (JP) .............................. JP2015-238535

(51) Int. Cl.
| | | |
|---|---|---|
| C07D 277/82 | (2006.01) | |
| C08F 16/32 | (2006.01) | |
| C08F 20/22 | (2006.01) | |
| C08F 20/30 | (2006.01) | |
| C08F 20/34 | (2006.01) | |
| C08F 20/38 | (2006.01) | |
| B29L 11/00 | (2006.01) | |
| C08F 220/38 | (2006.01) | |

(52) U.S. Cl.
CPC ............ *C07D 277/82* (2013.01); *C08F 16/32* (2013.01); *C08F 20/22* (2013.01); *C08F 20/38* (2013.01); *B29L 2011/0066* (2013.01); *C08F 220/387* (2020.02); *G02F 2202/022* (2013.01)

(58) Field of Classification Search
CPC .. C07D 277/82; C07D 303/34; C07D 303/36; C07D 305/06; C07C 69/52; C07C 43/168; C08F 16/32; C08F 20/22; C08F 20/30; C08F 20/34; C08F 20/38
See application file for complete search history.

(56) References Cited

U.S. PATENT DOCUMENTS

| | | |
|---|---|---|
| 2006/0189602 A1 | 8/2006 | Zhou et al. |
| 2014/0235857 A1 | 8/2014 | Sakamoto et al. |
| 2015/0191473 A1 | 7/2015 | Laurent et al. |
| 2016/0145363 A1 | 5/2016 | Sakamoto et al. |
| 2016/0200841 A1 | 7/2016 | Sakamoto |
| 2016/0257659 A1 | 9/2016 | Sakamoto et al. |
| 2016/0280672 A1 | 9/2016 | Sakamoto et al. |

FOREIGN PATENT DOCUMENTS

| | | |
|---|---|---|
| JP | 2008-526687 A | 7/2008 |
| JP | 2015-518009 A | 6/2015 |
| WO | 2012/147904 A1 | 11/2012 |
| WO | 2013/046781 A1 | 4/2013 |
| WO | 2014/010325 A1 | 1/2014 |
| WO | 2015/025793 A1 | 2/2015 |
| WO | 2015/064698 A1 | 5/2015 |
| WO | WO-2015064698 A1 * | 5/2015 |

OTHER PUBLICATIONS

Hou et al., "The synthesis and biological activity of N-benzothiazolyl-N'-tert-butylhydrazide compounds" in Chinese, Jingxi Huagong Zhongjianti , 2002, vol. 32, No. 4 , pp. 18-19, (2 pages).
Raj Put et al., "Synthesis,Spectral Analysis and in Vitro Biological Evaluation of Azetidinone Derivatfves of 5-Nitroindazole", Heterocyclic Letters, 2013, vol. 3, No. 2, pp. 191-196, (6 pages).
International Search Report dated Feb. 28, 2017, issued in counterpart International Application No. PCT/JP2016/085300 (5 pages).
Notification of Reasons for Refusal dated Nov. 9, 2017, issued in counterpart Japanese Patent Application No. 2017-549347, w/English translation (16 pages).
Decision to Grant a Patent dated Apr. 10, 2018, issued in counterpart Japanese Patent Application No. 2017-549347, w/English translation (7 pages).

* cited by examiner

*Primary Examiner* — Vu A Nguyen
(74) *Attorney, Agent, or Firm* — Westerman, Hattori, Daniels & Adrian, LLP

(57) ABSTRACT

The polymerizable compound has a hydrazone moiety. The present invention also provides a polymerizable composition in which discoloration and reduction of aligning property do not easily occur. Furthermore, the present invention provides a polymer obtained by polymerizing a polymerizable composition containing a compound obtained by the production method and an optically anisotropic body using the polymer. The present invention provides a method for producing a polymerizable compound including a step of reacting a compound represented by General Formula (I-B-a) with a compound represented by General Formula (I-B-b) to obtain a compound represented by General Formula (I-C), and provides a composition which contains a compound obtained by this production method.

5 Claims, No Drawings

METHOD FOR PRODUCING POLYMERIZABLE COMPOUND

TECHNICAL FIELD

The present invention relates to a method for producing a polymerizable compound having a hydrazone moiety, in which a substituent such as an alkyl group is introduced on a nitrogen atom, and a benzothiazole moiety, a polymerizable composition containing the compound, a polymerizable liquid crystal composition, and an optically anisotropic body using the polymerizable liquid crystal composition.

BACKGROUND ART

Compounds (polymerizable compounds) having a polymerizable group are used for various optical materials. For example, it is possible to produce a polymer having uniform alignment by aligning a polymerizable composition including a polymerizable compound in a liquid crystal state and then carrying out polymerization. Such a polymer can be used for a polarizing plate, a retardation plate, or the like, which is necessary for a display. In many cases, polymerizable compositions including two or more kinds of polymerizable compounds are used in order to satisfy the required optical properties, polymerization rate, solubility, melting point, glass transition temperature, polymer transparency, mechanical strength, surface hardness, heat resistance, and light fastness. At that time, the polymerizable compound to be used is required to impart good physical properties to the polymerizable composition without adversely affecting other characteristics.

In order to improve the viewing angle of the liquid crystal display, there is a demand to reduce or reverse the birefringence wavelength dispersion of the retardation film. As materials for this purpose, various polymerizable compounds having reverse wavelength dispersion or low wavelength dispersion have been developed. As such a compound, a polymerizable compound is known which has a hydrazone moiety, in which a substituent such as an alkyl group is introduced on a nitrogen atom, and a benzothiazole moiety. Examples of key intermediates in the production of the compounds include 2-hydrazino-benzothiazole having a substituent such as an alkyl group on a nitrogen atom. In the producing of the key intermediates, in the related art, from the viewpoint of yield, ease of synthesis, productivity, and the like, a method is known in which 2-hydrazino-benzothiazole and alkyl halide or the like are reacted in the presence of a base (PTL 1 to PTL 3). However, in the case of producing a polymerizable compound using an intermediate obtained by this method, there is a problem in that discoloration and/or reduction of aligning property easily occurs when the retardation film containing the polymerizable compound is irradiated with ultraviolet light for a long period. In the case where a film in which discoloration and/or reduction of aligning property occurs is used, for example, in a display, there is a problem that the quality of the display product may be greatly reduced in that unevenness in the brightness of the screen may occur and colors may become unnatural. Therefore, there is a demand for the development of a method for producing a polymerizable compound capable of solving such a problem.

CITATION LIST

Patent Literature

[PTL 1] WO2014/010325A1
[PTL 2] WO2013/046781A1
[PTL 3] WO2012/147904A1

SUMMARY OF INVENTION

Technical Problem

The present invention provides a method for producing a polymerizable compound, which has a hydrazone moiety, in which a substituent such as an alkyl group is introduced on a nitrogen atom, and a benzothiazole moiety, and a composition containing the compound. In addition, the present invention provides a polymerizable composition in which discoloration and reduction in aligning property do not easily occur when a film-shaped polymer obtained by polymerizing a polymerizable composition containing a polymerizable compound obtained by the production method is irradiated with ultraviolet light for a long period. Furthermore, the present invention provides a polymer obtained by polymerizing a polymerizable composition containing a compound obtained by the production method, and an optically anisotropic body using the polymer.

Solution to Problem

As a result of intensive research to solve the above problems, the present inventors developed a method for producing a polymerizable compound, which has a hydrazone moiety, in which a substituent such as an alkyl group is introduced on a nitrogen atom, and a benzothiazole moiety. That is, the present invention provides a method for producing a polymerizable compound which includes a step of obtaining a compound represented by General Formula (I-C) by reacting a compound represented by General Formula (I-B-a) with a compound represented by General Formula (I-B-b); a polymerizable composition containing the above compound; resins, resin additives, oils, filters, adhesives, pressure sensitive adhesives, oils and fats, inks, pharmaceuticals, cosmetics, detergents, building materials, packaging materials, liquid crystal materials, organic EL materials, organic semiconductor materials, electronic materials, display elements, electronic devices, communication equipment, automobile parts, aircraft parts, mechanical parts, agricultural chemicals, food, each using the compound, and products using any one of them; a polymerizable liquid crystal composition; a polymer obtained by polymerizing the polymerizable liquid crystal composition; and an optically anisotropic body using the polymer.

Advantageous Effects of Invention

In the case where the optically anisotropic body using the polymerizable liquid crystal composition containing the compound produced by the production method of the present invention is irradiated with ultraviolet light for a long period, discoloration does not easily occur and reduction in aligning property does not easily occur, thus, the compound produced by the production method of the present invention is useful for optical material applications such as optical compensation films.

DESCRIPTION OF EMBODIMENTS

The present invention relates to a method for producing a polymerizable compound, which has a hydrazone moiety, in which a substituent such as an alkyl group is introduced on a nitrogen atom, and a benzothiazole moiety; a composition containing the above polymerizable compound; resins, resin additives, oils, filters, adhesives, pressure sensitive adhesives, oils and fats, inks, pharmaceuticals, cosmetics, detergents, building materials, packaging materials, liquid crystal materials, organic EL materials, organic semiconductor materials, electronic materials, display elements, electronic devices, communication equipment, automobile parts, aircraft parts, mechanical parts, agricultural chemicals, food, and products utilizing the same, which use the above compound; a polymerizable liquid crystal composition; a polymer obtained by polymerizing the polymerizable liquid crystal composition; and an optically anisotropic body using the polymer.

General Formula (I-B-a):

[Chem. 1]

$$W^2\text{—NH—NH}_2 \qquad \text{(I-B-a)}$$

$W^2$ represents a linear or branched alkyl group having 2 to 20 carbon atoms in which one —$CH_2$— or two or more non-adjacent —$CH_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, or represents a linear or branched hydroxyalkyl group having 3 to 20 carbon atoms in which one —$CH_2$— or two or more non-adjacent —$CH_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=C—CF—, or —C≡C—, and arbitrary hydrogen atoms in the alkyl group may be substituted with a fluorine atom. From the viewpoint of ease of synthesis, discoloration and aligning property in the case of being irradiated with ultraviolet light, in General Formula (I-B-a), it is preferable that the group represented by $W^2$ represents a linear or branched alkyl group having 2 to 20 carbon atoms in which one —$CH_2$— or two or more non-adjacent —$CH_2$—'s may each independently be substituted with —O—, —S—, —CH=CH—, —CF=CF—, or —C≡C—, or represents a linear or branched hydroxyalkyl group having 3 to 20 carbon atoms in which one —$CH_2$— or two or more non-adjacent —$CH_2$—'s may each independently be substituted with —O—, —S—, —CH=CH—, —CF=CF—, or —C≡C—, provided that arbitrary hydrogen atoms in the alkyl group and the hydroxyalkyl group may be substituted with a fluorine atom; and in General Formula (I-B-a), the group represented by $W^2$ preferably represents a compound selected from Formula (W2-a-1) to Formula (W2-a-6) below:

[Chem. 2]

 (W2-a-1)

 (W2-a-2)

 (W2-a-3)

 (W2-a-4)

 (W2-a-5)

 (W2-a-6)

(in the formulae, k2a represents an integer of 2 to 20, k2b represents an integer of 1 to 5, k2c represents an integer of 3 to 20, and k2d represents an integer of 1 to 5). From the viewpoint of liquid crystallinity, reverse wavelength dispersion, and solubility in a solvent of the compound represented by formula (I), in Formula (W2-a-1), k2a more preferably represents an integer of 4 to 12, even more preferably represents an integer of 4 to 8, and particularly preferably represents 6. In Formulae (W2-a-2) and (W2-a-3), k2b more preferably represents an integer of 1 to 4, even more preferably represents an integer of 1 to 3, and particularly preferably represents 2. In Formula (W2-a-4), k2c more preferably represents an integer of 3 to 12, even more preferably represents an integer of 3 to 8, and particularly preferably represents an integer of 4 to 6. In Formulae (W2-a-5) and (W2-a-6), k2d more preferably represents an integer of 1 to 4, even more preferably represents an integer of 1 to 3, and particularly preferably represents 2. In Formula (W2-a-1) to Formula (W2-a-6), the groups represented by Formula (W2-a-1), Formula (W2-a-3), Formula (W2-a-4), or Formula (W2-a-6) are more preferable.

As the compound represented by General Formula (I-B-a), compounds represented by formula (I-B-a-1) to formula (I-B-a-4) are preferable:

[Chem. 3]

 (I-B-a-1)

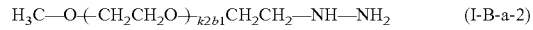 (I-B-a-2)

 (I-B-a-3)

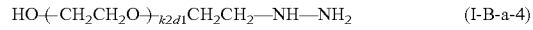 (I-B-a-4)

(in the formulae, k2a1 represents an integer of 2 to 20, k2b1 represents an integer of 1 to 5, k2c1 represents an integer of 3 to 20, and k2d1 represents an integer of 1 to 5), compounds represented by formula (I-B-a-1-1) to formula (I-B-a-1-4) are more preferable:

[Chem. 4]

 (I-B-a-1-1)

 (I-B-a-2-1)

 (I-B-a-3-1)

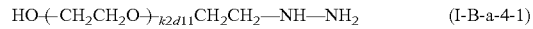 (I-B-a-4-1)

(in the formulae, k2a11 represents an integer of 4 to 12, k2b11 represents an integer of 1 to 4, k2c11 represents an integer of 3 to 12, and k2d11 represents an integer of 1 to 4), and compounds represented by formula (I-B-a-2-1-1) and formula (I-B-a-4-1-1) are particularly preferable:

[Chem. 5]

 (I-B-a-2-1-1)

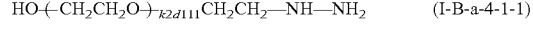 (I-B-a-4-1-1)

(in the formulae, k2b111 represents an integer of 1 to 3, and k2d111 represents an integer of 1 to 3).

General Formula (I-B-b):

[Chem. 6]

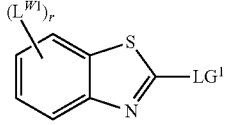

(I-B-b)

[Chem. 7]

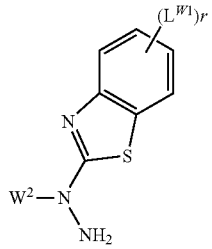

(I-C)

$L^{W1}$ represents a fluorine atom, a chlorine atom, a bromine atom, an iodine atom, a pentafluorosulfuranyl group, a nitro group, a cyano group, a dimethylamino group, a diethylamino group, a diisopropylamino group, or a linear or branched alkyl group having 1 to 20 carbon atoms, in which one —$CH_2$— or two or more non-adjacent —$CH_2$—'s may each independently be substituted with —O—, —S—, —CH=CH—, —CF=CF—, or —C≡C—, and arbitrary hydrogen atoms in the alkyl group may be substituted with a fluorine atom. In addition, plural $L^{W1}$'s, if any, may be the same or different. From the viewpoint of ease of synthesis and ease of availability of raw materials, $L^{W1}$ preferably represents a fluorine atom, a chlorine atom, a nitro group, a cyano group, a dimethylamino group, or a linear alkyl group having 1 to 12 carbon atoms, in which one —$CH_2$— or two or more non-adjacent —$CH_2$—'s may each independently be substituted with —O—, or —S—; and particularly preferably represents a fluorine atom, a chlorine atom, a nitro group, a cyano group, a dimethylamino group, a methyl group, or a methoxy group.

In General Formula (I-B-b), r represents an integer of 0 to 4. From the viewpoint of ease of synthesis and ease of availability of raw materials, r preferably represents an integer of 0 to 2, more preferably represents 0 or 1, and particularly preferably represents 0.

In General Formula (I-B-b), $LG^1$ represents a group which reacts with the compound represented by General Formula (I-B-a) to thereby be desorbed. From the viewpoint of ease of synthesis, ease of availability of raw materials, and reactivity, $LG^1$ preferably represents a fluorine atom, a chlorine atom, a bromine atom, an iodine atom, a methoxy group, a methylsulfanyl group, a hydroxyl group, a mercapto group, an amino group, a methylamino group, a dimethylamino group, a hydrazinyl group, or a benzothiazol-2-yl disulfanyl group, more preferably represents a fluorine atom, a chlorine atom, a bromine atom, an iodine atom, a methoxy group, an amino group, or a hydrazinyl group, even more preferably represents a fluorine atom, a chlorine atom, a bromine atom, or an iodine atom, still more preferably represents a fluorine atom or a chlorine atom, and particularly preferably represents a chlorine atom.

In a step in which the compound represented by General Formula (I-B-a) is reacted with the compound represented by General Formula (I-B-b) to obtain a compound represented by General Formula (I-C), reaction conditions in which the reaction is carried out in the presence of an alkali or a base are preferable. From the viewpoint of yield and ease of purification, it is preferable to use a base and, as the base, ammonia, a primary amine, a secondary amine, a tertiary amine, an aromatic amine, or salts thereof are preferable, secondary amines, tertiary amines, and aromatic amines are more preferable from the viewpoint of yield, and tertiary amines are even more preferable. More specifically, N,N-dimethylethylamine, triethylamine, N-ethyldiisopropylamine, pyridine, piperidine, and N,N-dimethylaminopyridine are preferable, and triethylamine and N-ethyldiisopropylamine are more preferable. As the alkali, calcium hydroxide, lithium hydroxide, magnesium hydroxide, potassium hydroxide, sodium hydroxide, sodium hydrogen carbonate, sodium carbonate, potassium hydrogen carbonate, potassium carbonate, cesium carbonate, calcium carbonate, and the like are preferable.

The reaction temperature is preferably −100° C. to 200° C. and, from the viewpoint of yield and reaction rate, more preferably −50° C. to 150° C., even more preferably −20° C. to 120° C., and yet more preferably 0° C. to 80° C.

As the reaction solvent, an organic solvent, water, an ionic liquid, or a supercritical fluid may be used alone, a plurality thereof may be mixed and used, a two-phase system may be used, or a solventless reaction may be used. Examples of organic solvents include isopropyl alcohol, 2-methoxyethanol, ethylene glycol, methanol, ethanol, propanol, chloroform, dichloromethane, 1,2-dichloroethane, acetone, acetonitrile, N,N-dimethylacetamide, dimethyl sulfoxide, ethyl acetate, butyl acetate, tetrahydrofuran, toluene, hexane, pentane, methyl isobutyl ketone, methyl ethyl ketone, dimethoxy ethane, and the like.

In the case where a reaction is carried out in a two-phase system between an organic solvent and water, it is also possible to add a phase transfer catalyst. Examples of the phase transfer catalyst include benzalkonium chloride, benzyltrimethylammonium bromide, polyoxyethylene (10) octylphenyl ether [Triton X-100], polyoxyethylene (20) sorbitan monolaurate [Tween 20], polyoxyethylene (20) sorbitan monopalmitate [Tween 40], polyoxyethylene (20) sorbitan monostearate [Tween 60] polyoxyethylene (23) lauryl ether [Brij 35], sorbitan monopalmitate [Span 40], and the like.

The amount of the reaction solvent is not particularly limited as long as it is possible to sufficiently release the reaction heat generated by the reaction, but if the amount of the solvent is excessively small, reaction heat accumulates in the reaction system and by-products are easily generated. On the other hand, if the amount of the solvent is excessively large, the concentration of the reactant decreases and the reaction rate significantly decreases. From the above viewpoint, the amount of the solvent is preferably 0.01 milliliter to 1 liter with respect to 1 gram of the compound represented by General Formula (I-B-b), the amount of the solvent is more preferably 0.1 milliliter to 100 milliliters with respect to 1 gram of the compound represented by General Formula (I-B-b), the amount of the solvent is even more preferably 1 milliliter to 20 milliliters with respect to 1 gram of the compound represented by General Formula (I-B-b), and the amount of the solvent is particularly preferably 2 milliliter to 10 milliliters with respect to 1 gram of the compound represented by General Formula (I-B-b).

The compound represented by general formula (I-C) preferably represents a compound selected from formula (I-C-1) to formula (I-C-6).

[Chem. 8]

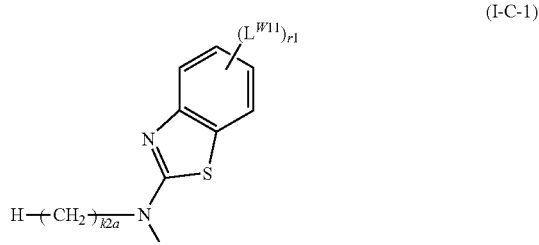
(I-C-1)

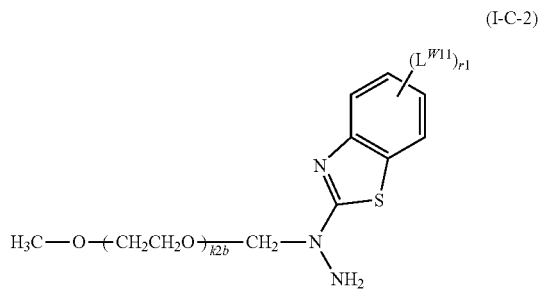
(I-C-2)

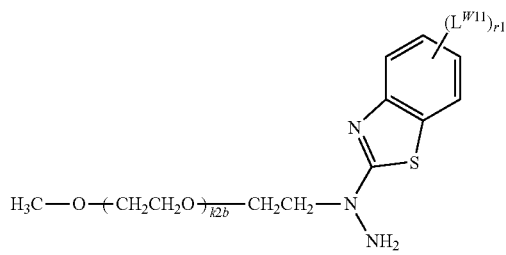
(I-C-3)

[Chem. 9]

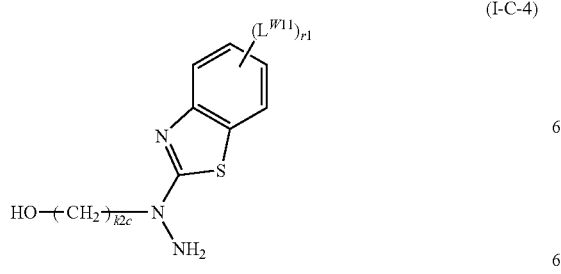
(I-C-4)

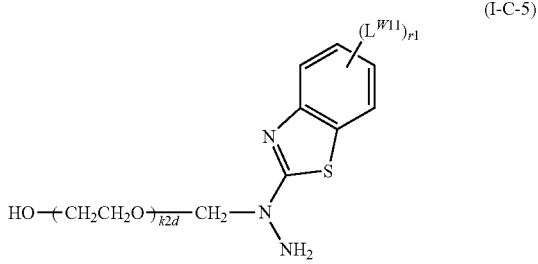
(I-C-5)

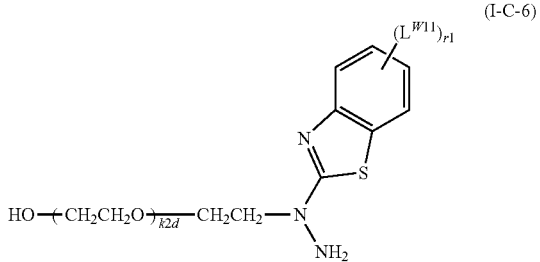
(I-C-6)

(In the formulae, k2a represents an integer of 2 to 20, k2b represents an integer of 1 to 5, k2c represents an integer of 3 to 20, k2d represents an integer of 1 to 5, $L^{W11}$ represents a fluorine atom, a chlorine atom, a nitro group, a cyano group, a dimethylamino group, or a linear alkyl group having 1 to 12 carbon atoms in which one —$CH_2$— or two or more non-adjacent —$CH_2$—'s may be each independently substituted with —O— or —S—, and r1 represents an integer of 0 to 2). From the viewpoint of the liquid crystallinity, the reverse wavelength dispersion property, and the solubility in a solvent of the compound represented by General Formula (I), in formula (I-C-1), k2a more preferably represents an integer of 4 to 12, even more preferably represents an integer of 4 to 8, and particularly preferably represents 6. In formula (I-C-2) and formula (I-C-3), k2b more preferably represents an integer of 1 to 4, even more preferably represents an integer of 1 to 3, and particularly preferably represents 2. In formula (I-C-4), k2c more preferably represents an integer of 3 to 12, even more preferably represents an integer of 3 to 8, and particularly preferably represents an integer of 4 to 6. In formula (I-C-5) and formula (I-C-6), k2d more preferably represents an integer of 1 to 4, even more preferably represents an integer of 1 to 3, and particularly preferably represents 2. In formula (I-C-1) to formula (I-C-6), a compound represented by formula (I-C-1), formula (I-C-3), formula (I-C-4), or formula (I-C-6) is more preferable, a compound represented by any one of formula (I-C-1-1) to formula (I-C-6-1) is even more preferable.

[Chem. 10]

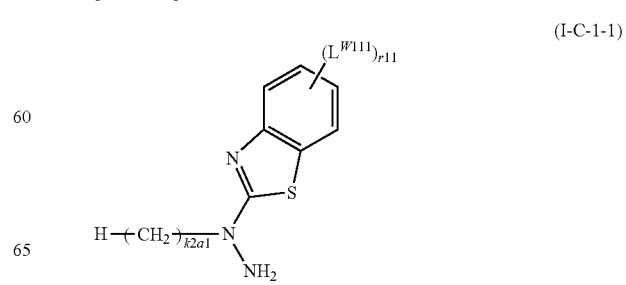
(I-C-1-1)

-continued (I-C-3-1)

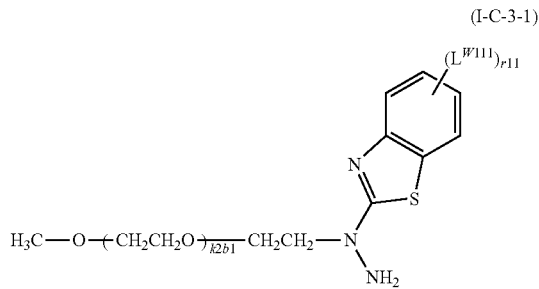

(I-C-4-1)

(I-C-6-1)

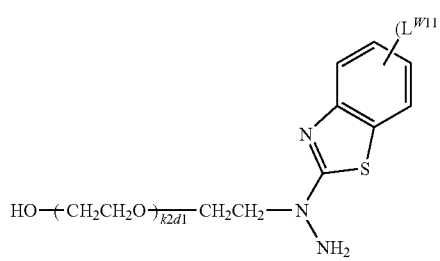

(In the formulae, k2a1 represents an integer of 2 to 20, k2b1 represents an integer of 1 to 5, k2c1 represents an integer of 3 to 20, k2d1 represents an integer of 1 to 5, $L^{W111}$ represents a fluorine atom, a chlorine atom, a nitro group, a cyano group, a dimethylamino group, a methyl group, or a methoxy group, and r11 represents 0 or 1). A compound represented by any one of formula (I-C-1-1-1) to formula (I-C-6-1-1) is yet more preferable.

[Chem. 11]

(I-C-1-1-1)

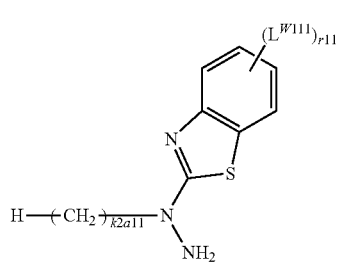

-continued (I-C-3-1-1)

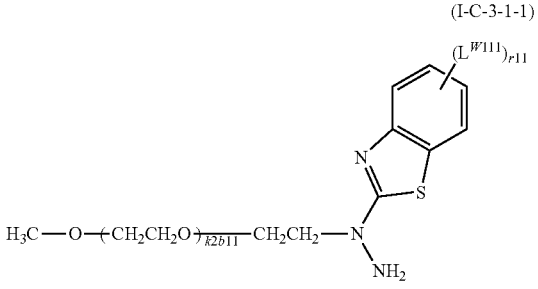

(I-C-4-1-1)

(I-C-6-1-1)

(In the formulae, k2a11 represents an integer of 4 to 12, k2b11 represents an integer 1 of 4, k2c11 represents an integer of 3 to 12, k2d11 represents an integer of 1 to 4, $L^{W111}$ represents a fluorine atom, a chlorine atom, a nitro group, a cyano group, a dimethylamino group, a methyl group, or a methoxy group, and r11 represents 0 or 1). A compound represented by formula (I-C-3-1-1) or formula (I-C-6-1-1) is particularly preferable.

[Chem. 12]

(I-C-3-1-1)

(I-C-6-1-1)

(In the formulae, k2b111 represents an integer of 1 to 3, and k2d111 represents an integer of 1 to 3.)

As the polymerizable compound for producing the compound represented by General Formula (I-C) as an intermediate, compounds represented by General Formula (I):

[Chem. 13]

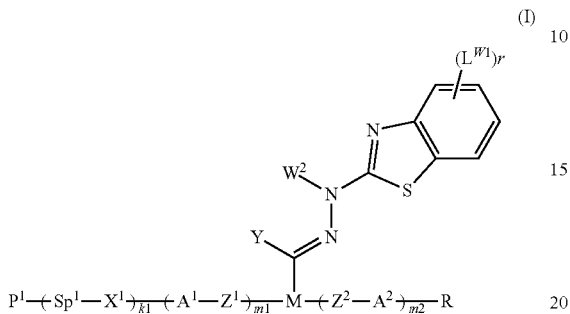
(I)

are preferable.

In General Formula (I), $P^1$ represents a polymerizable group, and the polymerizable group is a group polymerizable by radical polymerization, radical addition polymerization, cationic polymerization, or anionic polymerization, and preferably represents a group selected from formula (P-1) to formula (P-20).

[Chem. 14]

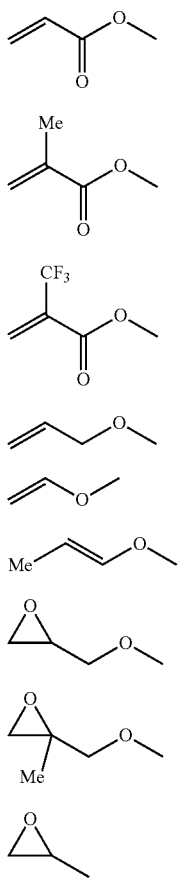

(P-1)
(P-2)
(P-3)
(P-4)
(P-5)
(P-6)
(P-7)
(P-8)
(P-9)

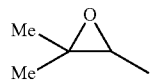
(P-10)

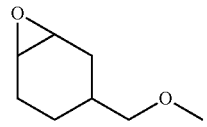
(P-11)

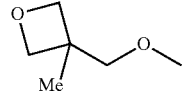
(P-12)

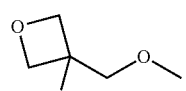
(P-13)

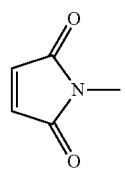
(P-14)

HS—
(P-15)

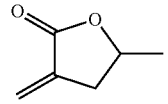
(P-16)

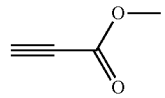
(P-17)

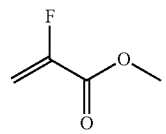
(P-18)

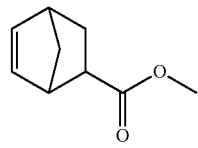
(P-19)

(P-20)

In particular, in the case where ultraviolet polymerization is carried out as a polymerization method, Formula (P-1), Formula (P-2), Formula (P-3), Formula (P-4), Formula (P-5), Formula (P-7), Formula (P-11), Formula (P-13), Formula (P-15), or Formula (P-18) is preferable, Formula (P-1), Formula (P-2), Formula (P-3), Formula (P-7), Formula (P-11), or Formula (P-13) is more preferable, Formula (P-1), Formula (P-2), or Formula (P-3) is even more preferable, and Formula (P-1) or Formula (P-2) is particularly preferable.

In General Formula (I), $Sp^1$ represents a spacer group, and plural $Sp^1$'s, if any, may be the same or different. The spacer group preferably represents an alkylene group having 1 to 20 carbon atoms in which one —$CH_2$— or two or more non-adjacent —$CH_2$—'s may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C—. From the viewpoint of ease of availability of raw materials and ease of synthesis, it is preferable that plural Sp's, if any, may be the same or different and each independently represents an alkylene group having 1 to 20 carbon atoms in which one —$CH_2$— or two or more non-adjacent —$CH_2$—'s may each independently be substituted with —O—, —COO—, —OCO—, —OCO—O—, —CO—NH—, —NH—CO—, —CH=CH—, or —C≡C—, it is more preferable that plural $Sp^1$'s, if any, may be the same or different and each independently represents an alkylene group having 1 to 10 carbon atoms in which one —$CH_2$— or two or more non-adjacent —$CH_2$—'s may each independently be substituted with —O—, —COO—, and —OCO—, it is even more preferable that plural $Sp^1$'s, if any, may be the same or different and each independently represents an alkylene group having 1 to 10 carbon atoms, and it is particularly preferable that plural $Sp^1$'s, if any, may be the same or different and each independently represents an alkylene group having 2 to 8 carbon atoms.

In General Formula (I), $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and plural $X^1$'s, if any, may be the same or different. From the viewpoint of ease of availability of raw materials and ease of synthesis, it is preferable that plural $X^1$'s, if any, may each be the same or different and each represents —O—, —S—, —$OCH_2$—, —$CH_2O$—, —COO—, —OCO—, —CO—S—, —S—CO—, —O—CO—O—, —CO—NH—, —NH—CO—, —COO—$CH_2CH_2$—, —OCO—$CH_2CH_2$—, —$CH_2CH_2$—COO—, —$CH_2CH_2$—OCO—, or a single bond; it is more preferable that plural $X^1$'s, if any, may each be the same or different and each represents —O—, —$OCH_2$—, —$CH_2O$—, —COO—, —OCO—, —COO—$CH_2CH_2$—, —OCO—$CH_2CH_2$—, —$CH_2CH_2$—COO—, —$CH_2CH_2$—OCO—, or a single bond; and it is particularly preferable that plural $X^1$'s, if any, may each be the same or different and each represents —O—, —COO—, —OCO—, or a single bond.

In General Formula (I), k1 represents an integer of 0 to 10, but from the viewpoint of solubility in a solvent and liquid crystallinity in the case of being added to a liquid crystal composition, k1 preferably represents an integer of 0 to 5, more preferably represents an integer of 1 to 3, and particularly preferably represents 1.

In General Formula (I), R represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which arbitrary hydrogen atoms in the group may be substituted with a fluorine atom, and in which one —$CH_2$— or two or more non-adjacent —$CH_2$—'s may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C—; or R represents a group represented by —$(X^2$—$Sp^2)_{k2}$-$P^2$. In the case where R represents a group other than the group represented by —$(X^2$—$Sp^2)$—$P^2$, from the viewpoint of liquid crystallinity and ease of synthesis, R more preferably represents a hydrogen atom, a fluorine atom, a chlorine atom, or a linear or branched alkyl group having 1 to 12 carbon atoms in which one —$CH_2$— or two or more non-adjacent —$CH_2$—'s may each independently be substituted with —O—, —COO—, —OCO—, or —O—CO—O—, even more preferably represents a hydrogen atom, a fluorine atom, a chlorine atom, or a linear alkyl group or a linear alkoxy group having 1 to 12 carbon atoms, and particularly preferably represents a linear alkyl group or a linear alkoxy group having 1 to 12 carbon atoms. In addition, in the case where R represents a group represented by —$(X^2$—$Sp^2)_{k2}$-$P^2$, the preferable structures of $P^2$, $Sp^2$, $X^2$, and k2 are respectively the same as the preferable structures of $P^1$, $Sp^1$, $X^1$, and k1.

In the case of forming a film where emphasis is placed on mechanical strength and curability, R more preferably represents a group represented by —$(X^2$—$Sp^2)_{k2}$-$P^2$. In addition, in the case of forming a film where emphasis is placed on having a small degree of cure shrinkage, R more preferably represents a group other than the group represented by —$(X^2$—$Sp^2)_{k2}$-$P^2$.

In General Formula (I), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted with one or more substituents L, plural $A^1$'s, if any, may be the same or different, and plural $A^2$'s, if any, may be the same or different. From the viewpoint of liquid crystallinity, ease of synthesis, and ease of availability of raw materials, it is preferable that plural $A^1$'s or plural $A^2$'s, if any, may be the same or different and each independently represents a 1,4-phenylene group, a 1,4-cyclohexylene group, or a naphthalene-2,6-diyl group, which may be unsubstituted or substituted with one or more substituents L, it is more preferable that plural $A^1$'s or plural $A^2$'s, if any, may each be the same or different and each independently represents a group selected from Formula (A-1) to Formula (A-11).

[Chem. 15]

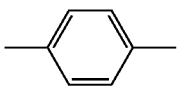 (A-1)

 (A-2)

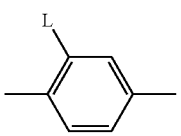 (A-3)

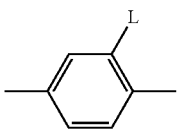 (A-4)

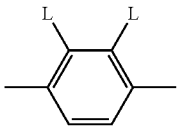 (A-5)

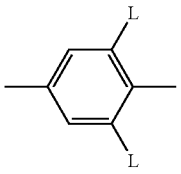 (A-6)

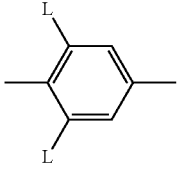 (A-7)

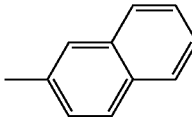 (A-8)

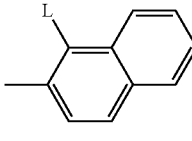 (A-9)

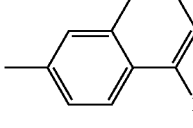 (A-10)

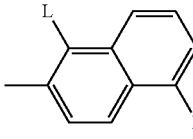 (A-11)

It is even more preferable that plural $A^1$'s or plural $A^2$'s, if any, may each be the same or different and each independently represents a group selected from Formula (A-1) to Formula (A-8), it is yet more preferable that plural A's or plural $A^2$'s, if any, may be the same or different and each independently represents a group selected from Formula (A-1) to Formula (A-4), and it is particularly preferable that plural $A^1$'s or plural $A^2$'s, if any, may each be the same or different and each independently represents Formula (A-1) or Formula (A-2).

In General Formula (I), L each independently represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more non-adjacent —$CH_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom; or L may represent a group represented by $P^L$—($Sp^L$-$X^L$)—, in which $P^L$ represents a polymerizable group, and the polymerizable group is a group polymerizable by radical polymerization, radical addition polymerization, cationic polymerization, or anionic polymerization, $Sp^L$ represents a linear alkylene group having 1 to 10 carbon atoms in which one —$CH_2$— or two or more non-adjacent —$CH_2$—'s may each independently be substituted with —O—, —COO—, or —OCO—, or a single bond, and, plural $Sp^L$'s, if any, may be the same or different, $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and plural $X^L$ s, if any, may be the same or different (however, $P^L$ ($Sp^L$-$X^L$)$_{kL}$— does not include —O—O— bonds), kL represents an integer of 0 to 10, and plural kL's, if present in the compound, may be the same or different. From the viewpoint of liquid crystallinity and ease of synthesis, it is preferable that plural L's, if any, may each be the same or different and each represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms in which arbitrary hydrogen atoms may be substituted with a fluorine atom, and in which one —$CH_2$— or two or more non-adjacent —$CH_2$—'s may each independently be substituted with a group selected from —O—, —S—, —CO—, —COO—, —OCO—, —O—CO—O—, —CH=CH—, —CF=CF—, or —C≡C—, it is more preferable that plural L's, if any, may each be the same or different and each represents a fluorine atom, a chlorine atom, or a linear or branched alkyl group having 1 to 12 carbon atoms in which arbitrary hydrogen atoms may be substituted with a fluorine atom and in which one —$CH_2$ or two or more non-adjacent —$CH_2$—'s may independently be substituted with a group selected from —O—, —COO—, or —OCO—, it is even more preferable that plural L's, if any, may each be the same or different and each represents a fluorine atom, a chlorine atom, or a linear or branched alkyl group or alkoxy group having 1 to 12 carbon atoms in which arbitrary hydrogen atoms may be substituted with a fluorine atom, and it is particularly preferable that plural L's, if any, may each be the same or different and each represents a fluorine atom, a chlorine atom, or a linear alkyl group or a linear alkoxy group having 1 to 8 carbon atoms.

In General Formula (I), $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH—COO—, —CH$_2$—OCO—, —CH=CH—, —N=N—, —CH=N—, —N=CH—, —CH=N—N=CH—, —CF=CF—, —C≡C—, or a single bond, plural $Z^1$'s, if any, may be the same or different, and plural $Z^2$'s, if any, may be the same or different. From the viewpoint of liquid crystallinity, ease of availability of raw materials, and ease of synthesis, it is preferable that plural $Z^1$'s or plural $Z^2$'s, if any, may each be the same or different and each independently represents —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, it is more preferable that plural $Z^1$'s or plural $Z^2$'s, if any, may each be the same or different and each independently represents —OCH$_2$—, —CH$_2$O—, —COO—, —OCO—, —CF$_2$O—, —OCF$_2$—, —CH$_2$CH$_2$—, or a single bond, and it is particularly preferable that plural $Z^1$'s or plural $Z^2$'s, if any, may each be the same or different and each independently represents —OCH$_2$—, —CH$_2$O—, —COO—, —OCO—, or a single bond.

In General Formula (I), m1 and m2 each independently represent an integer of 0 to 6, and m1+m2 represents an integer of 0 to 6. From the viewpoint of solubility in a solvent, liquid crystallinity, discoloration and aligning property in the case of being irradiated with ultraviolet light, m1 and m2 preferably each independently represents an integer of 1 to 3, and particularly preferably each independently represents 1 or 2.

In General Formula (I), M represents a trivalent aromatic group which may be substituted. From the viewpoint of ease of synthesis and ease of availability of raw materials, M preferably represents a group selected from Formula (M-1) to Formula (M-6):

[Chem. 16]

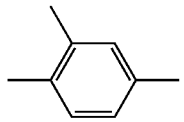
(M-1)

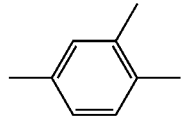
(M-2)

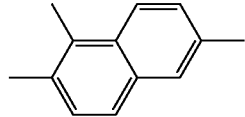
(M-3)

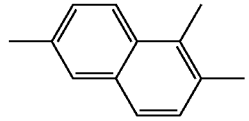
(M-4)

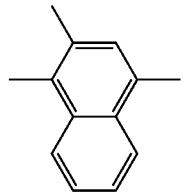
(M-5)

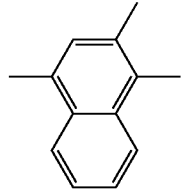
(M-6)

(in the formulae, these groups may be unsubstituted or substituted with one or more substituents $L^M$, and arbitrary —CH='s may each independently be substituted with —N=), M more preferably represents a group selected from Formula (M-1), Formula (M-2), Formula (M-5), or Formula (M-6) which may be unsubstituted or substituted with one or more substituents $L^M$, M even more preferably represents a group selected from Formula (M-1) or Formula (M-2) which may be unsubstituted or substituted with one or more substituents L, and M particularly preferably represents a group selected from an unsubstituted Formula (M-1) or Formula (M-2).

In General Formula (I), $L^M$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— or two or more non-adjacent —CH$_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom; or $L^M$ may represent a group represented by $P^{LM}$—(Sp$^{LM}$-X$^{LM}$)$_{kLM}$, in which $P^{LM}$ represents a polymerizable group, and the polymerizable group is a group polymerizable by radical polymerization, radical addition polymerization, cationic polymerization, or anionic polymerization, $Sp^{LM}$ represents a spacer group or a single bond, and plural $Sp^{LM}$'s, if any, may be the same or different, $X^{LM}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and plural $X^{LM}$'s, if any, may be the same or different (however, $P^{LM}$—$(Sp^{LM}$-$X^{LM})_{kLM}$— does not include —O—O-bonds), and kLM represents an integer of 0 to 10, and plural $L^{M}$'s, if present in the compound, may be the same or different. From the viewpoint of liquid crystallinity and ease of synthesis, it is preferable that plural $L^{M}$'s, if any, may each be the same or different and each represents a fluorine atom, a chlorine atom, a pentafluorosulfuranyl group, a nitro group, a cyano group, a methylamino group, a dimethylamino group, a diethylamino group, or a linear or branched alkyl group having 1 to 20 carbon atoms in which arbitrary hydrogen atoms may be substituted with a fluorine atom and in which one —CH$_2$— or two or more non-adjacent —CH$_2$—'s may each independently be substituted with a group selected from —O—, —S—, —CO—, —COO—, —OCO—, —O—CO—O—, —CH=CH—, —CF=CF—, or —C≡C—, it is more preferable that plural $L^{M}$'s, if any, may each be the same or different and each represents a fluorine atom, a chlorine atom, a nitro group, a cyano group, or a linear or branched alkyl group having 1 to 12 carbon atoms in which arbitrary hydrogen atoms may be substituted with a fluorine atom and in which one —CH$_2$— or two or more non-adjacent —CH$_2$—'s may each independently be substituted with a group selected from —O—, —COO—, or —OCO—, it is even more preferable that plural $L^{M}$'s, if any, may each be the same or different and each represents a fluorine atom, a chlorine atom, a nitro group, a cyano group, or a linear or branched alkyl group or alkoxy group having 1 to 12 carbon atoms in which arbitrary hydrogen atoms may be substituted with a fluorine atom, and it is particularly preferable that plural $L^{M}$'s, if any, may each be the same or different and each represents a fluorine atom, a chlorine atom, a nitro group, a cyano group, a methyl group, or a methoxy group.

In General Formula (I), Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, dimethylamino group, diethylamino group, diisopropylamino group, trimethylsilyl group, dimethylsilyl group, a thioisocyano group, or a linear or branched alkyl group having 1 to 20 carbon atoms in which one —CH$_2$— or two or more non-adjacent —CH$_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom. From the viewpoint of liquid crystallinity and ease of synthesis, it is preferable that Y represents a hydrogen atom or a linear or branched alkyl group having 1 to 12 carbon atoms in which arbitrary hydrogen atoms in the group may be substituted with a fluorine atom and in which one —CH$_2$— or two or more non-adjacent —CH$_2$—'s may each independently be substituted with —O—, —COO—, or —OCO—, it is more preferable that Y represents a hydrogen atom or a linear alkyl group having 1 to 12 carbon atoms, and it is particularly preferable that Y represents a hydrogen atom.

Here, the compound represented by General Formula (I) does not include an —O—O— bond.

More specifically, the compound represented by General Formula (I) is preferably a compound represented by General Formulae (I-ia), (I-ib), and (I-ii):

[Chem. 17]

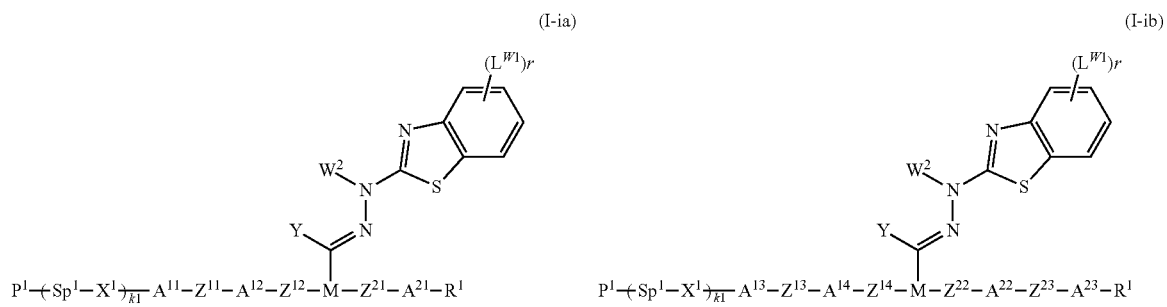

-continued

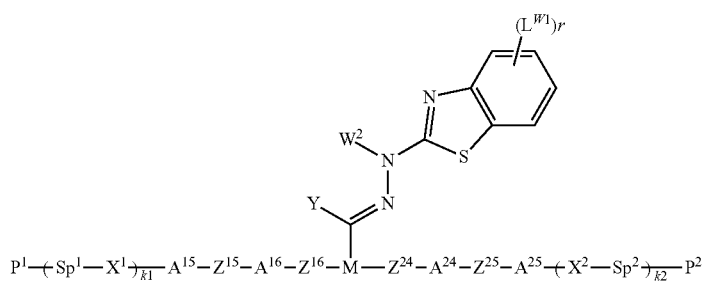
(I-ii)

(in the formulae, $P^1$, $P^2$, $Sp^1$, $Sp^2$, $X^1$, $X^2$, k1, k2, M, Y, $W^2$, $L^{W1}$, and r represent the same meanings as in General Formula (I); $R^1$ represents a hydrogen atom, a fluorine atom, a chlorine atom, or a linear or branched alkyl group having 1 to 12 carbon atoms in which one —$CH_2$— or two or more non-adjacent —$CH_2$—'s may each independently be substituted with —O—, —COO—, —OCO—, or —O—CO—O—; $A^{11}$, $A^{21}$, $A^{13}$, $A^{22}$, $A^{23}$, $A^{15}$, and $A^{25}$ each independently represent a 1,4-phenylene group or a 1,4-cyclohexylene group, these groups may be unsubstituted or substituted with one or more substituents $L^1$; $A^{12}$, $A^{14}$, $A^{16}$, and $A^{24}$ each independently represent a 1,4-cyclohexylene group, these groups may be unsubstituted or substituted with one or more substituents $L^2$; $L^1$ and $L^2$ each independently represent the same meaning as L in General Formula (I), plural $L^1$'s, if present in the compound, may be the same or different, and plural $L^2$'s, if present in the compound, may be the same or different; $Z^{11}$, $Z^{21}$, $Z^{13}$, $Z^{22}$, $Z^{23}$, $Z^{15}$, and $Z^{25}$ each independently represent —$OCH_2$—, —$CH_2O$—, —$CH_2CH_2$—, —COO—, —OCO—, —$CF_2O$—, —$OCF_2$—, or a single bond; and $Z^{12}$, $Z^{14}$, $Z^{16}$, and $Z^{24}$ each independently represent —$OCH_2$—, —$CH_2O$—, —$CH_2CH_2$—, —COO—, —OCO—, —$CF_2O$—, or —$OCF_2$—).

More specifically, the compound represented by General Formula (I) is preferably a compound represented by any one of General Formulae (I-ia-i), (I-ib-i), and (I-ii-i):

[Chem. 18]

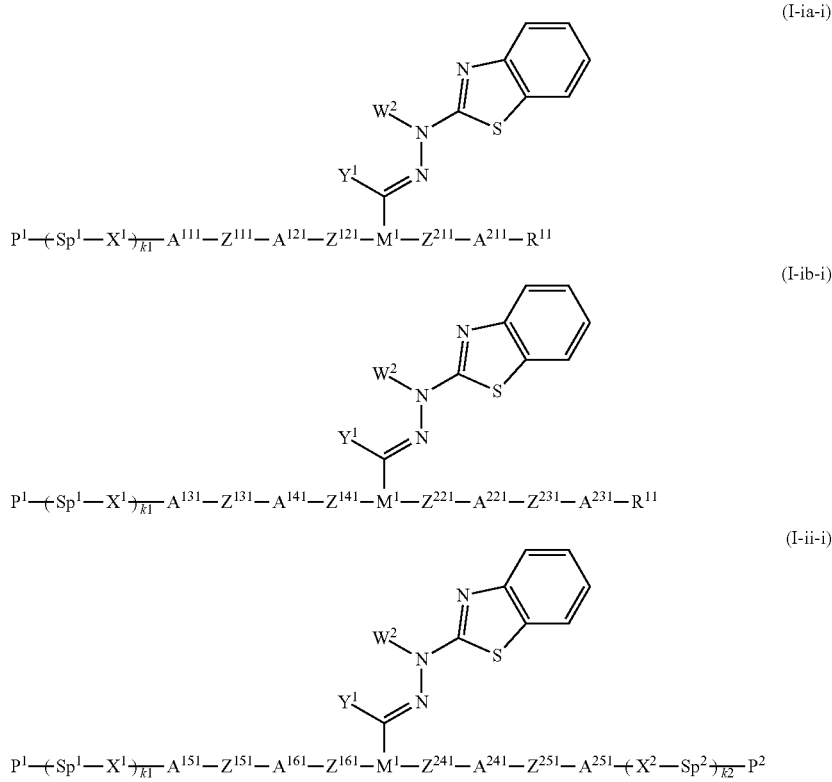

(in the formulae, $P^1$, $P^2$, $Sp^1$, $Sp^2$, $X^1$, $X^2$, k1, k2, and $W^2$ represent the same meanings as in General Formula (I), $R^{11}$ represents a linear alkyl group or linear alkoxy group having 1 to 12 carbon atoms, $A^{111}$, $A^{131}$, $A^{151}$, and $A^{251}$ represent a 1,4-phenylene group, these groups may be unsubstituted or substituted with one or more substituents $L^{11}$, $A^{121}$, $A^{141}$, $A^{221}$, $A^{231}$, $A^{161}$, and $A^{241}$ represent a 1,4-cyclohexylene group, $A^{211}$ represents a 1,4-phenylene group or a 1,4-cyclohexylene group, and the 1,4-phenylene group may be unsubstituted or may be substituted with one or more substituents $L^{11}$, $L^{11}$ represents a fluorine atom, a chlorine atom, or a linear or branched alkyl group having 1 to 20 carbon atoms in which one —$CH_2$— or two or more non-adjacent —$CH_2$—'s may each independently be substituted with —O—, —CO—, —COO—, or —OCO—, and arbitrary hydrogen atoms in the alkyl group may be substituted with a fluorine atom, plural $L^{11}$'s, if present in the compound, may be the same or different, $Z^{111}$, $Z^{121}$, $Z^{131}$, $Z^{141}$, $Z^{151}$, $Z^{161}$, $Z^{241}$, and $Z^{251}$ each independently represent —$OCH_2$—, —$CH_2O$—, —COO—, or —OCO—, $Z^{211}$, $Z^{221}$, and $Z^{231}$ each represent a single bond, $M^1$ represents a group selected from Formula (M-1-1) or Formula (M-2-1):

[Chem. 19]

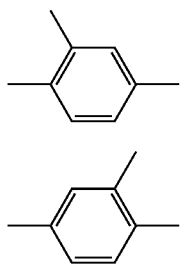

(M-1-1)

(M-2-1)

and $Y^1$ represents a hydrogen atom).

The compound represented by General Formula (I-B-a) is preferably produced by a reaction between the compound represented by General Formula (I-A) and hydrazine:

[Chem. 20]

$$W^2\text{-}LG^2 \quad\quad (I\text{-}A)$$

(in the formula, $W^2$ represents the same meaning as above, and $LG^2$ represents a group which reacts with hydrazine to thereby be desorbed).

In General Formula (I-A), $LG^2$ represents a group which reacts with hydrazine to thereby be desorbed and, from the viewpoint of ease of synthesis, cost, and reactivity, $LG^2$ preferably represents a chlorine atom, a bromine atom, an iodine atom, a methanesulfonyl group, or a p-toluenesulfonyl group, more preferably represents a chlorine atom, a bromine atom, or an iodine atom, and particularly preferably represents a chlorine atom or a bromine atom.

As the hydrazine to be used in the reaction of the compound represented by General Formula (I-A) with hydrazine, it is possible to use hydrazine, hydrazine monohydrate (hydrazine hydrate), hydrazine salt, and the like. The above may be used as is, diluted with a solvent, supported on a polymer or a solid phase, or adsorbed on a porous substance.

In the reaction of the compound represented by General Formula (I-A) with hydrazine, an alkali or a base may or may not be used. Examples of the alkali or base include those described above. From the viewpoint of ease of purification, conditions which do not use an alkali or a base are preferable.

In the reaction of the compound represented by General Formula (I-A) with hydrazine, the reaction temperature is preferably −100° C. to 200° C., and from the viewpoint of yield and reaction rate, more preferably −50° C. to 150° C., even more preferably −20° C. to 120° C., and yet more preferably 0° C. to 80° C.

In the reaction of the compound represented by General Formula (I-A) with hydrazine, examples of the types of the reaction solvent are as described above, and from the viewpoint of the solubility and yield of the compound, alcohol-based solvents are preferable, and examples thereof include isopropyl alcohol, 2-methoxyethanol, ethylene glycol, methanol, ethanol, propanol, and the like. In the case where a reaction is carried out in a two-phase system between an organic solvent and water, it is also possible to add a phase transfer catalyst. Examples of the phase transfer catalyst include the examples described above.

The amount of the reaction solvent is not particularly limited as long as it is possible to sufficiently release the reaction heat generated by the reaction, but if the amount of the solvent is excessively small, reaction heat accumulates in the reaction system and by-products are easily generated. On the other hand, if the amount of the solvent is excessively large, the concentration of the reactant decreases and the reaction rate significantly decreases. From the above viewpoint, the amount of the solvent is preferably 0.01 milliliter to 1 liter with respect to 1 gram of the compound represented by General Formula (I-A), the amount of the solvent is more preferably 0.1 milliliter to 100 milliliters with respect to 1 gram of the compound represented by General Formula (I-A), the amount of the solvent is even more preferably 1 milliliter to 20 milliliters with respect to 1 gram of the compound represented by General Formula (I-A), and the amount of the solvent is particularly preferably 2 milliliter to 10 milliliters with respect to 1 gram of the compound represented by General Formula (I-A).

The compound represented by General Formula (I) Is preferably produced by a reaction between the compound represented by General Formula (I-C) and the compound represented by General Formula (I-D):

[Chem. 21]

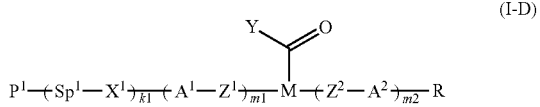

(I-D)

(in the formula, $P^1$, $Sp^1$, $X^1$, k1, R, $A^1$, $A^2$, $Z^1$, Z, m1, m2, M, and Y represent the same meanings as in General Formula (I)).

In the reaction between the compound represented by Formula (I-C) and the compound represented by General Formula (I-D), an acid is preferably added from the viewpoint of the reaction rate. As the acid, an inorganic acid or an organic acid may be used. Examples of the inorganic acid include hydrochloric acid, sulfuric acid, nitric acid, and the like. Examples of the organic acid include acetic acid, formic acid, oxalic acid, p-toluenesulfonic acid, p-toluenesulfonic acid monohydrate, p-toluenesulfonic acid pyridinium, (±)-10-camphorsulfonic acid, and the like. From the viewpoint of ease of purification, p-toluenesulfonic acid monohydrate, p-toluenesulfonic acid pyridinium, (±)-10-camphorsulfonic acid, and the like are preferable. The amount of acid to be added is preferably 0.001 equivalent to 10 equivalents with respect to the compound represented by General Formula (I-D), more preferably 0.001 equivalent to 1 equivalent, and particularly preferably 0.01 equivalent to 0.5 equivalent.

The reaction temperature is preferably −100° C. to 200° C., and from the viewpoint of yield and reaction rate, the reaction temperature is more preferably −50° C. to 150° C., even more preferably −20° C. to 120° C., yet more preferably 0° C. to 80° C., and particularly preferably from room temperature to 50° C.

As a reaction solvent, it is preferable to use alcohol or ether, and more preferable to use a mixed solvent of alcohol and ether. More specifically, examples thereof include those examples described above.

In addition, it is possible to carry out purification as necessary after the reaction. Examples of purification methods include chromatography, filtration, recrystallization, distillation, sublimation, reprecipitation, adsorption, centrifugation, liquid separation treatment, dispersion washing, and the like. In the case of using a refining agent, examples of refining agents include silica gel, alumina, activated carbon, activated clay, celite, zeolite, mesoporous silica, carbon nanotube, carbon nanohorn, "Bincho" charcoal, charcoal, graphene, ion-exchanged resins, acid clay, silicon dioxide, diatomaceous earth, Pearlite, cellulose, organic polymers, porous gels, and the like.

The compound represented by General Formula (I) preferably represents a compound represented by Formula (I-ia-i-1) to Formula (I-ii-i-2).

[Chem. 22]

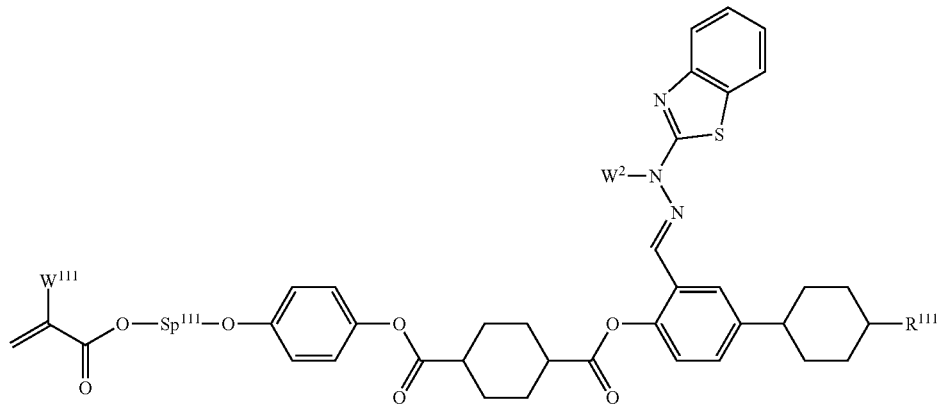

(I-ia-i-1)

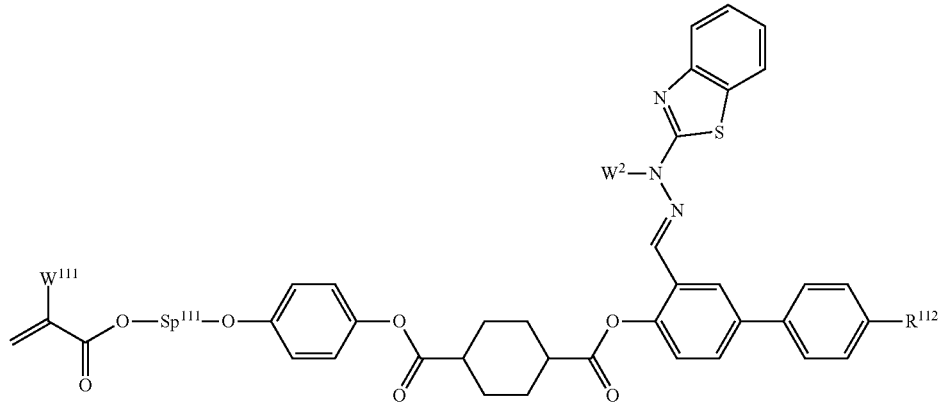

(I-ia-i-2)

(I-ia-i-3)
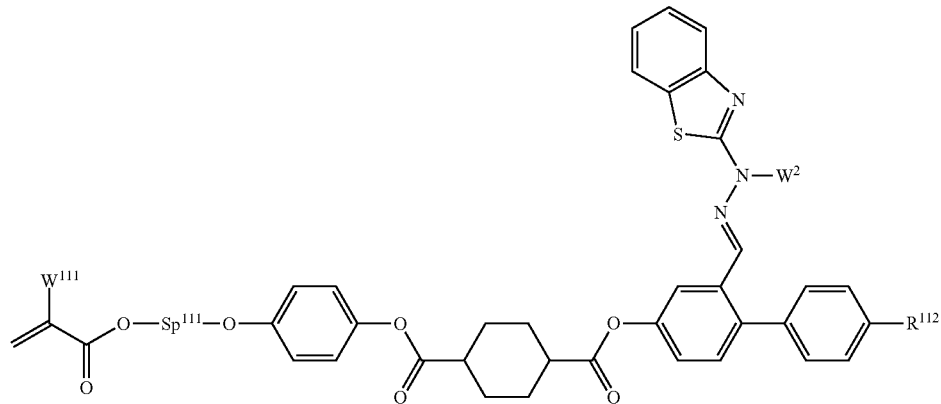
[Chem. 23]
(I-ia-i-4)
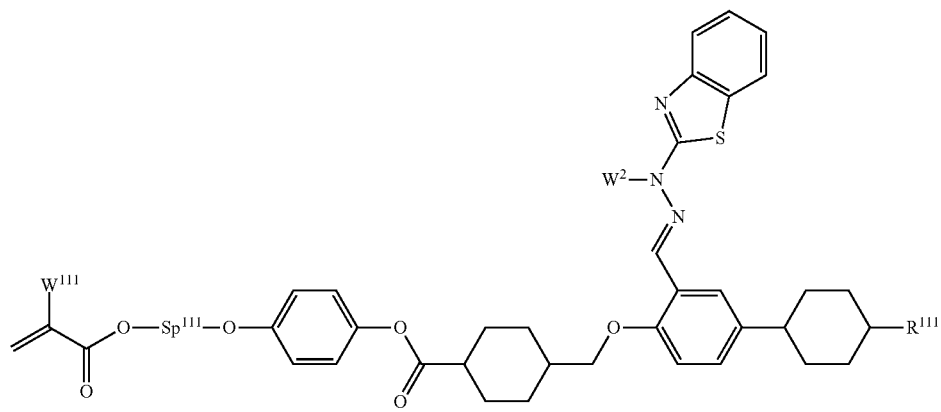
(I-ia-i-5)
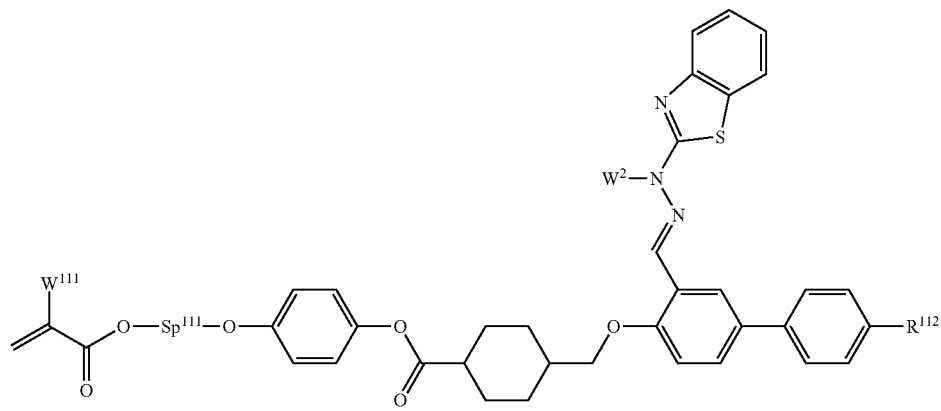

(I-ia-i-6)
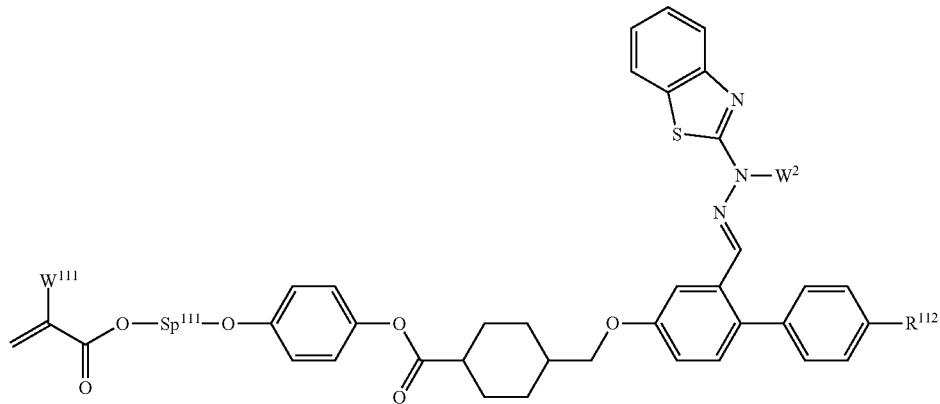
[Chem. 24]
(I-ib-i-1)
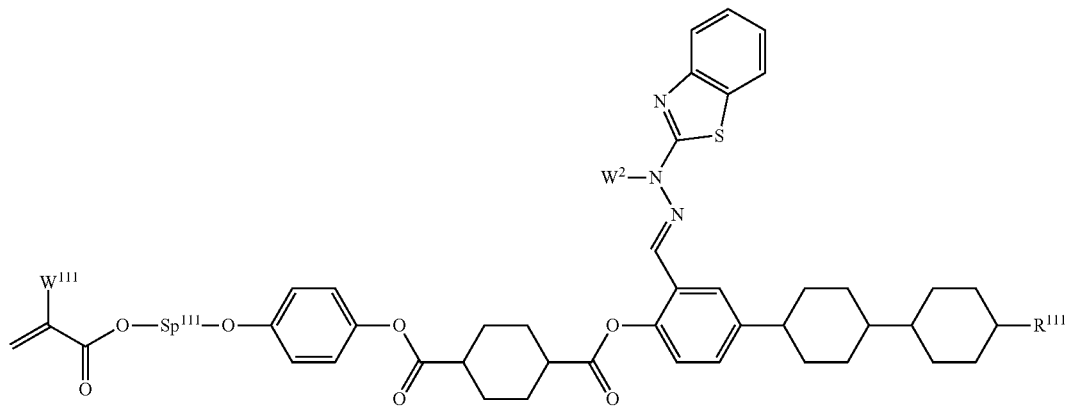
(I-ib-i-2)
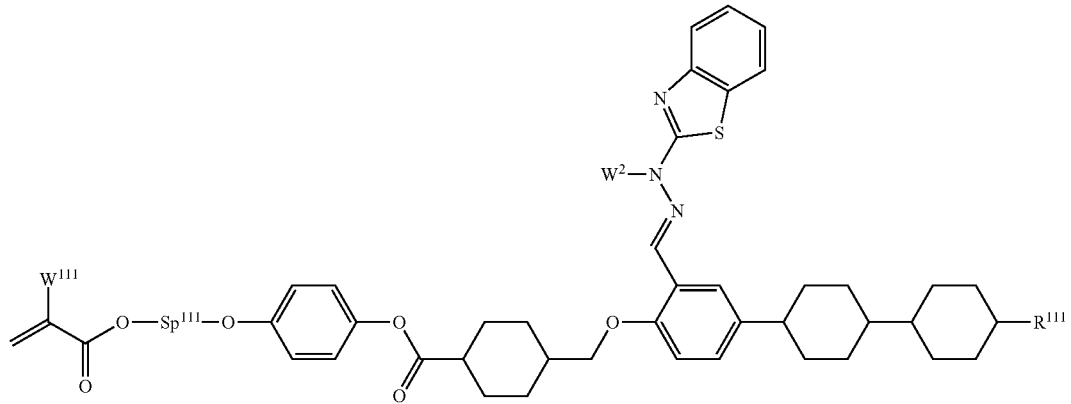

[Chem. 25]

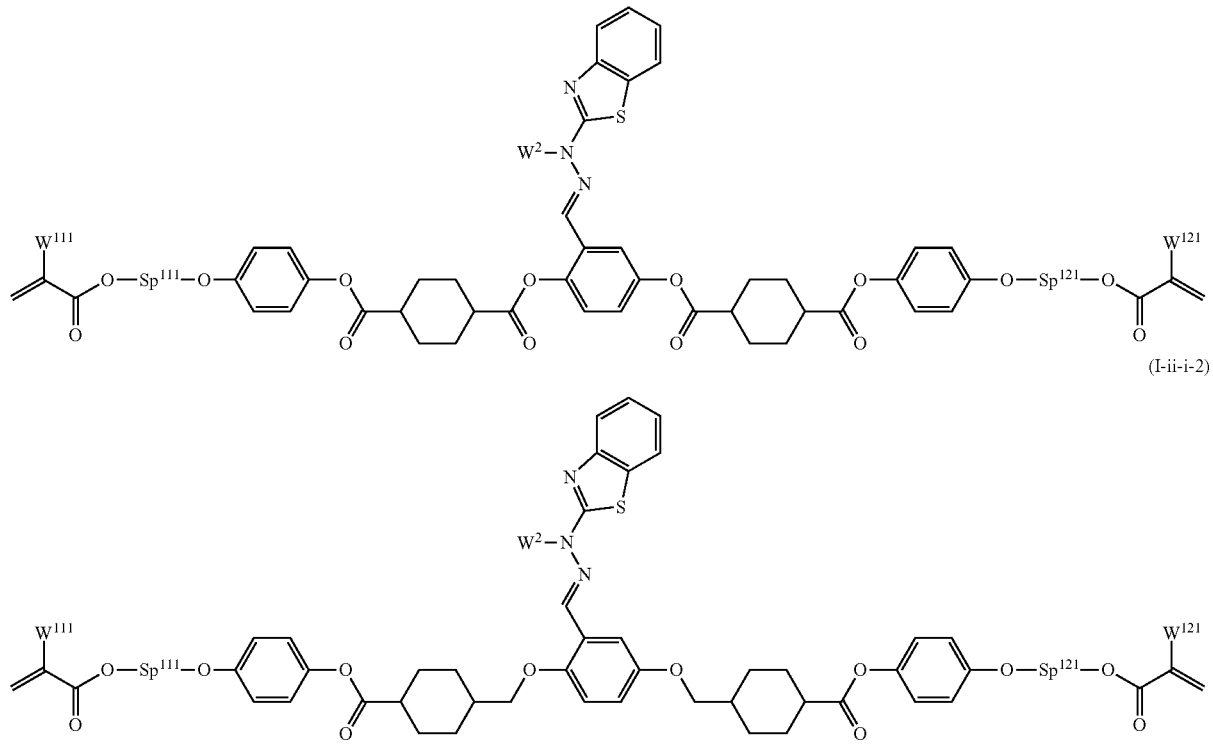

(I-ii-i-1)

(I-ii-i-2)

(In the formulae, $W^{111}$ and $W^{121}$ represent a hydrogen atom or a methyl group, $Sp^{111}$ and $Sp^{121}$ represent an alkylene group having 2 to 8 carbon atoms, $R^{111}$ represents a linear alkyl group having 1 to 8 carbon atoms, $R^{112}$ represents a linear alkyl group or linear alkoxy group having 1 to 8 carbon atoms, and $W^2$ represents the same meaning as in Formula (I).)

The compound represented by General Formula (I) more preferably represents a compound represented by any one of Formula (I-ia-i-1-1) to Formula (I-ii-i-2-2).

[Chem. 26]

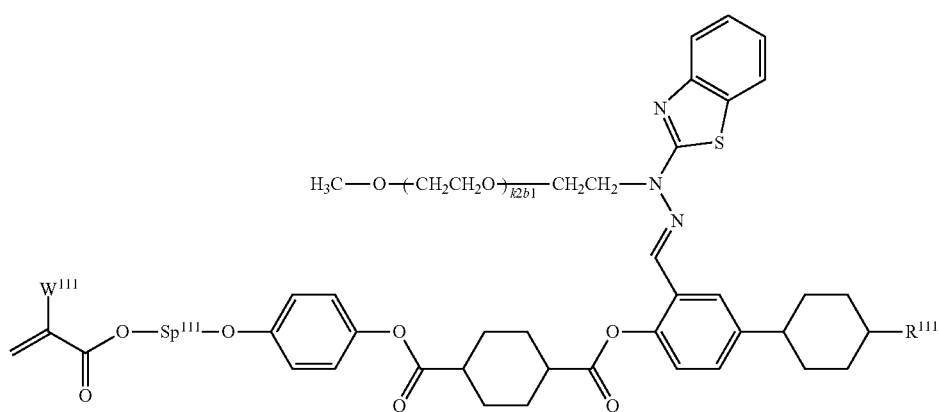

(I-ia-i-1-1)

-continued
(I-ia-i-4-1)
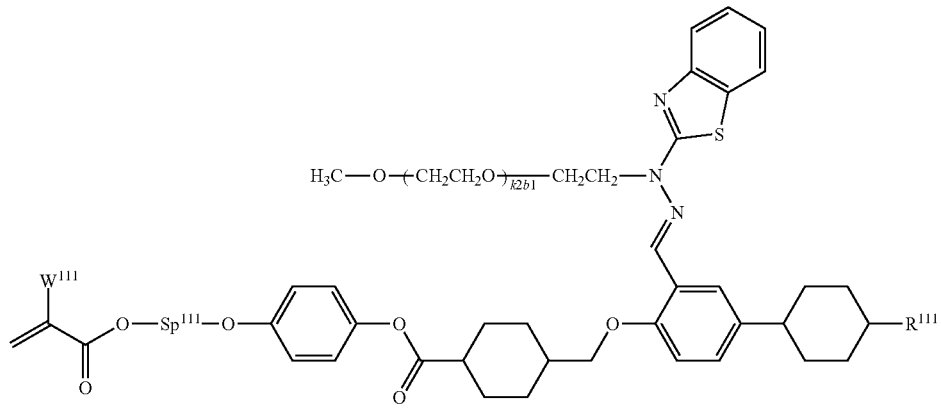
(I-ia-i-6-1)
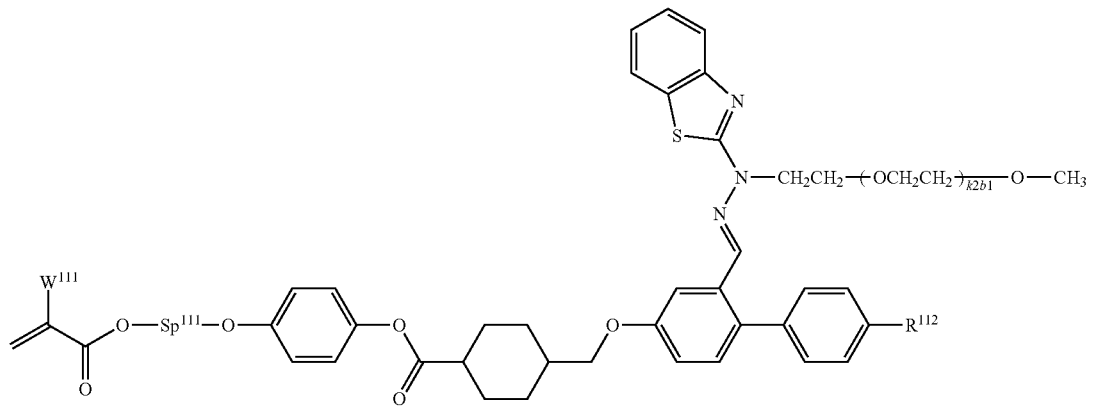
[Chem. 27]
(I-ii-i-1-1)
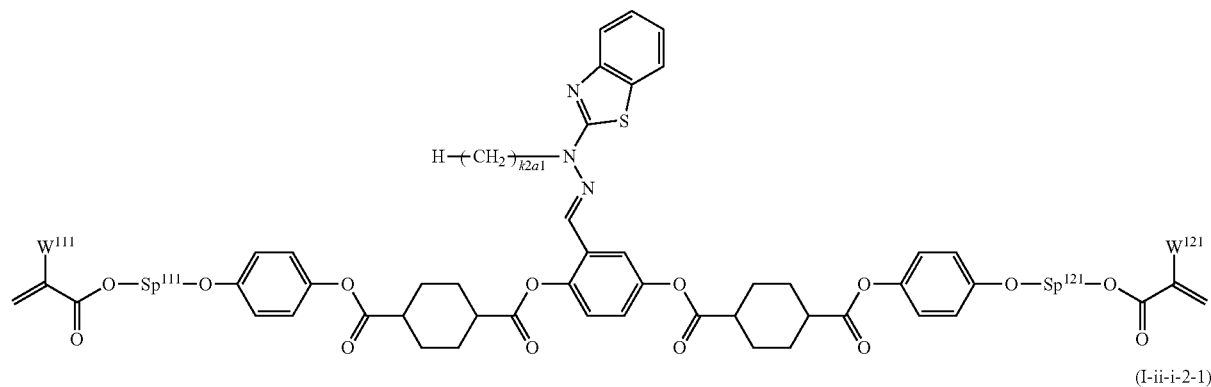
(I-ii-i-2-1)
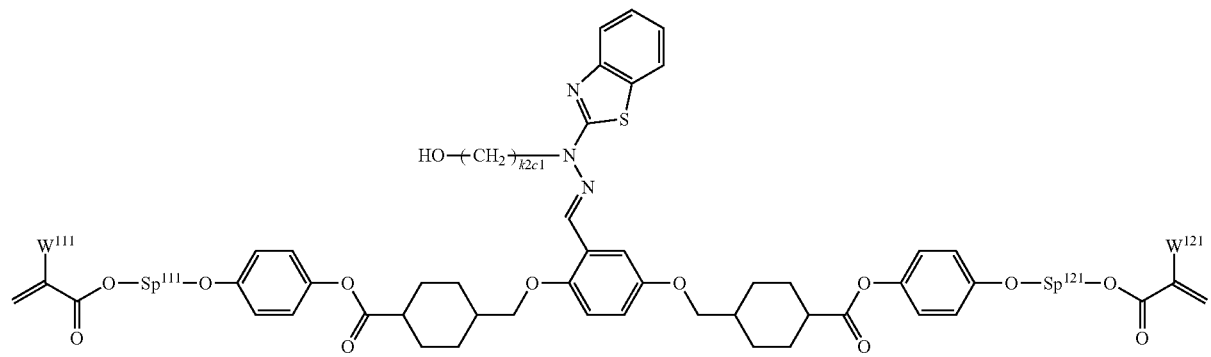

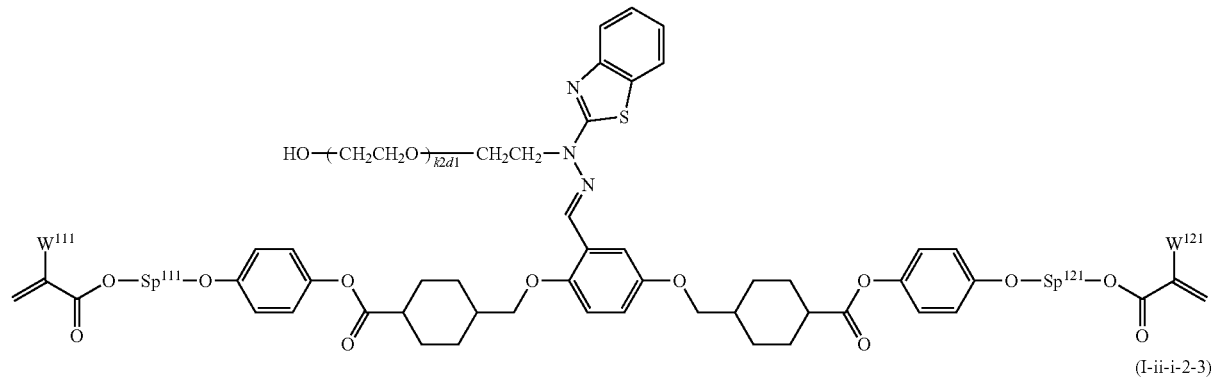

(I-ii-i-2-2)

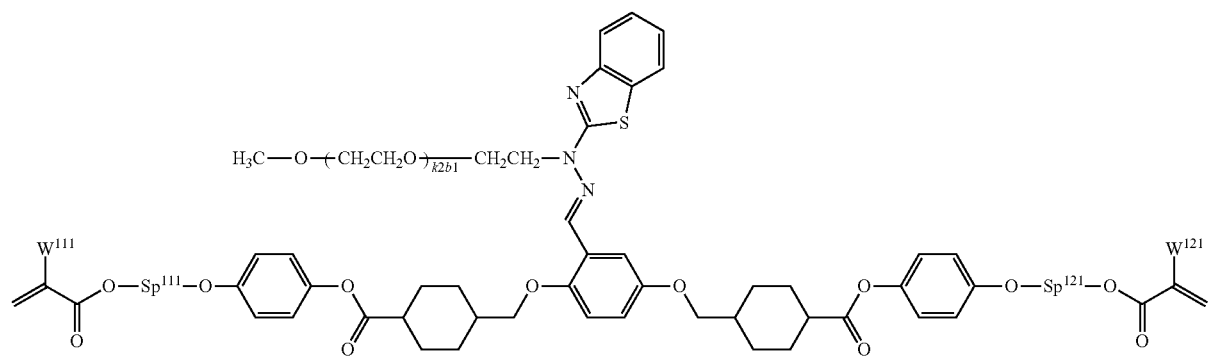

(I-ii-i-2-3)

(In the formulae, $W^{111}$ and $W^{121}$ represent a hydrogen atom or a methyl group, $Sp^{111}$ and $Sp^{121}$ represent an alkylene group having 2 to 8 carbon atoms, $R^{111}$ represents a linear alkyl group having 1 to 8 carbon atoms, $R^{112}$ represents a linear alkyl group or a linear alkoxy group having 1 to 8 carbon atoms, K2a1 represents an integer of 2 to 10, k2b1 represents 1 or 2, k2c1 represents an integer of 3 to 8, and k2d1 represents 1 or 2.)

Using the compound represented by General Formula (I) as an intermediate, it is possible to produce the compound represented by General Formula (II). The polymerizable compound (II) preferably represents a compound represented by Formula (II-ii-i-2-1) or Formula (II-ii-i-2-2):

[Chem. 28]

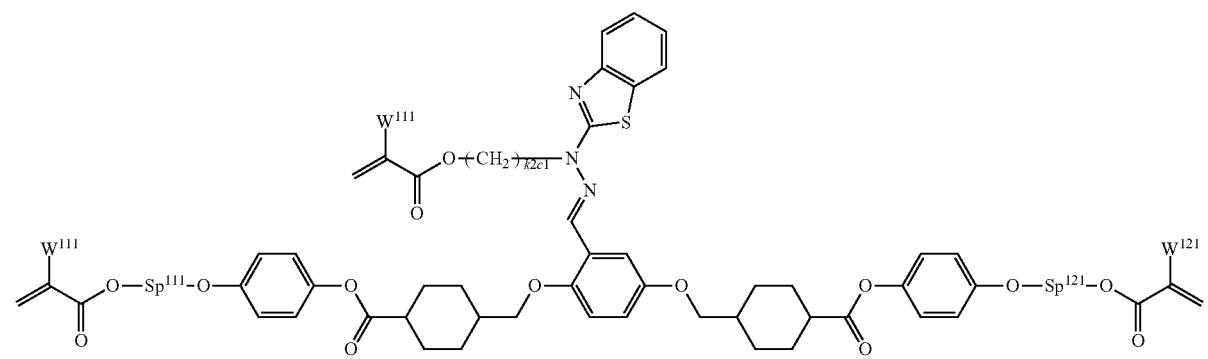

(II-ii-i-2-1)

(II-ii-i-2-2)

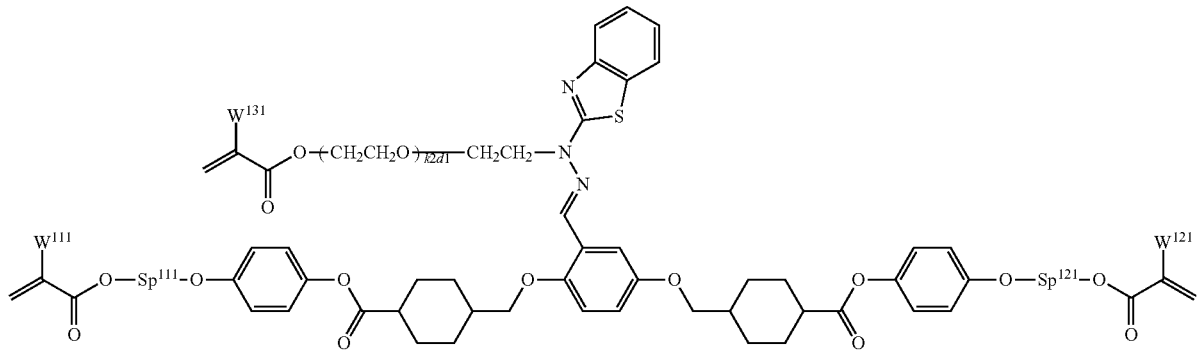

(in the formulae, $W^{111}$, $W^{121}$, and $W^{131}$ represent a hydrogen atom or a methyl group, $Sp^{111}$ and $Sp^{121}$ represent an alkylene group having 2 to 8 carbon atoms, k2c1 represents an integer of 3 to 8, and k2d1 represents 1 or 2).

EXAMPLES

Further description will be given below of the present invention with reference to examples, but the present invention is not limited to these examples. In addition, "%" in the compositions of the following Examples and Comparative Examples means "% by mass". When handling substances which are unstable to oxygen and/or moisture in each step, it is preferable to carry out operations in an inert gas such as nitrogen gas or argon gas.

(GC Analysis Conditions)
Column: Agilent Technologies, J & W Column DB-1HT, 15 m×0.25 mm×0.10 μm
Temperature program: 100° C. (1 min)–(20° C./min)–250° C.–(10° C./min)–380° C.–(7° C./min)–400° C. (2.64 min)
Inlet temperature: 350° C.
Detector temperature: 400° C.

(UPLC Analysis Condition)
Column: Waters ACQUITY UPLC BEH $C_{18}$, 2.1×100 mm, 1.7 μm
Elution solvent: acetonitrile/water (90:10)
Flow rate: 0.5 mL/min
Detector: UV, 210 nm
Column oven: 40° C.

(Example 1) Production of Compound Represented by Formula (C-1)

[Chem. 29]

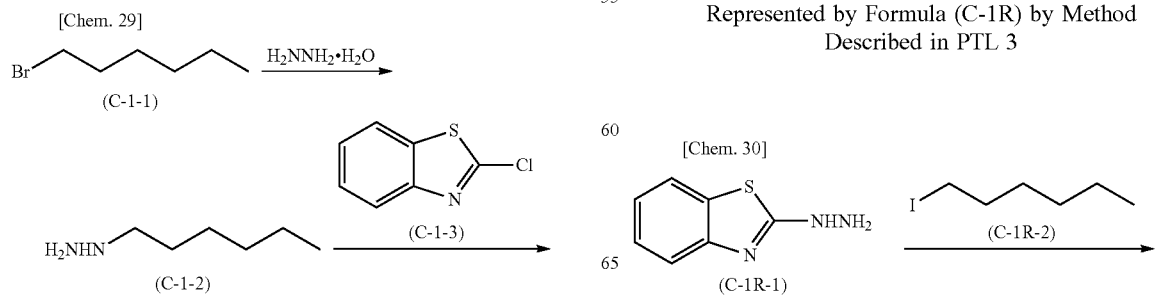

Under a nitrogen atmosphere, 45.49 g of hydrazine monohydrate and 227 mL of ethanol were added to a reaction container, and the mixture was stirred at 80° C. A solution in which 15.00 g of the compound represented by Formula (C-1-1) was dissolved in 30 mL of ethanol was added dropwise thereto and the mixture was heated and stirred at 80° C. for 4 hours. Water was added and extraction was performed with dichloromethane. After washing the organic layer with a saline solution, by drying over sodium sulfate and distilling off the solvent, 7.12 g of a compound represented by Formula (C-1-2) was obtained.

Under a nitrogen atmosphere, 8.00 g of the compound represented by Formula (C-1-3), 6.20 g of triethylamine, and 40 mL of 1,2-dimethoxyethane were added to the reaction container. 7.12 g of the compound represented by Formula (C-1-2) was added dropwise thereto and then heating and stirring were carried out at 60° C. for 3 hours. The reaction solution was poured into a mixed solution of 500 mL of water and 100 mL of methanol, and the precipitated solid was filtered. After the solid was washed with water, washing was carried out with hexane to obtain 5.13 g of the compound represented by Formula (C-1).

(Comparative Example 1) Production of Compound Represented by Formula (C-1R) by Method Described in PTL 3

[Chem. 30]

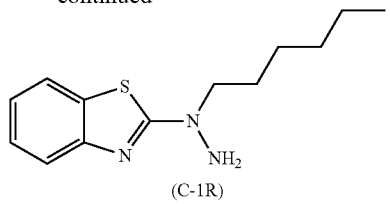

(C-1R)

Under a nitrogen atmosphere, 2.00 g of the compound represented by Formula (C-1R-1), 20 mL of N,N-dimethylformamide, 8.36 g of potassium carbonate, 3.08 g of the compound represented by Formula (C-1R-2) were added to a reaction container, and the mixture was stirred at 50° C. for 7 hours. After cooling, the resultant was poured into 200 mL of water and extracted with 300 mL of ethyl acetate. After drying over sodium sulfate, the solvent was distilled off. Purification was performed by column chromatography (silica gel) to obtain 2.10 g of a compound represented by Formula (C-1R).

(Example 2) Production of Compound Represented by Formula (C-2)

[Chem. 31]

Under a nitrogen atmosphere, 5.0 g of the compound represented by Formula (C-2-1), 4.6 g of diisopropylethylamine, and 30 mL of dichloromethane were added to a reaction container. After 3.1 g of the compound represented by Formula (C-2-2) was added dropwise thereto, heating and stirring were carried out. After a liquid separation treatment was performed, purification was carried out by column chromatography (alumina) to obtain 2.0 g of the compound represented by Formula (C-2).

(Comparative Example 2) Production of Compound Represented by Formula (C-2R) by Method Described in PTL 3

[Chem. 32]

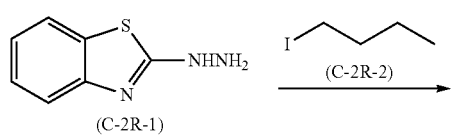

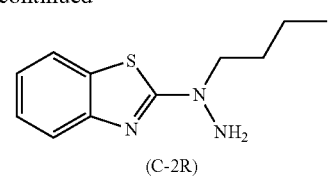

(C-2R)

Under a nitrogen atmosphere, 2.00 g of a compound represented by Formula (C-2R-1), 20 mL of N,N-dimethylformamide, 8.36 g of potassium carbonate, and 2.67 g of a compound represented by Formula (C-3R-2) were added to a reaction container, and the mixture was stirred at 50° C. for 7 hours. After cooling, the resultant was poured into 200 mL of water and extracted with 300 mL of ethyl acetate. After drying over sodium sulfate, the solvent was distilled off. Purification was performed by column chromatography (silica gel) to obtain 2.34 g of a compound represented by Formula (C-2R).

(Example 3) Production of Compound Represented by Formula (C-3)

[Chem. 33]

Under a nitrogen atmosphere, 7.1 g of the compound represented by Formula (C-3-2), 3.9 g of pyridine, and 20 mL of 1,2-dimethoxyethane were added to a reaction container. After 5.5 g of the compound represented by Formula (C-3-1) and 15 mL of 1,2-dimethoxyethane were mixed and added dropwise thereto, heating and stirring were carried out. After performing a liquid separation treatment, purification was performed by column chromatography (alumina) to obtain 4.2 g of a compound represented by Formula (C-3).

(Comparative Example 3) Production of Compound Represented by Formula (C-3R) by Method Described in PTL 3

[Chem. 34]

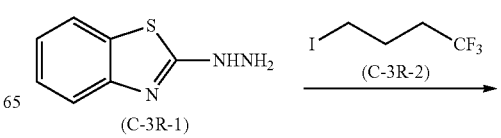

-continued

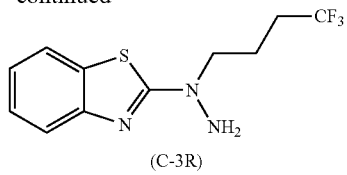
(C-3R)

Under a nitrogen atmosphere, 1.45 g of the compound represented by Formula (C-3R-1), 20 mL of N,N-dimethylformamide, 3.63 g of potassium carbonate, and 2.50 g of a compound represented by Formula (C-3R-2) were added to a reaction container, and the mixture was stirred at 80° C. for 8 hours. After cooling, the resultant was poured into 200 mL of water and extracted with 300 mL of ethyl acetate. After drying over sodium sulfate, the solvent was distilled off. Purification was performed by column chromatography (silica gel) to obtain 0.96 g of a compound represented by Formula (C-3R).

(Example 4) Production of Compound Represented by Formula (C-4)

[Chem. 35]

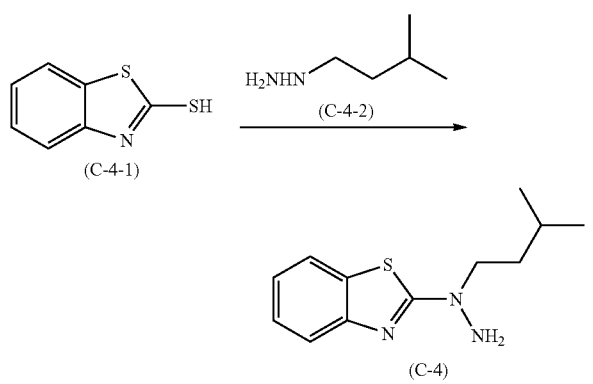

Under a nitrogen atmosphere, 5.0 g of a compound represented by Formula (C-4-1), 6.1 g of triethylamine, and 20 mL of 1,2-dimethoxyethane were added to a reaction container. After 4.6 g of the compound represented by Formula (C-4-2) and 15 mL of 1,2-dimethoxyethane were mixed and added dropwise thereto, heating and stirring were carried out. After performing a liquid separation treatment, drying was carried out to obtain 5.6 g of the compound represented by Formula (C-4).

(Comparative Example 4) Production of Compound Represented by Formula (C-4R) by Method Described in PTL 3

[Chem. 36]

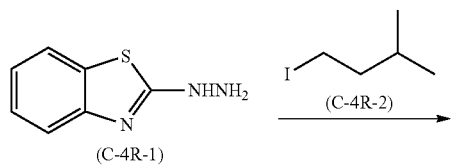

-continued

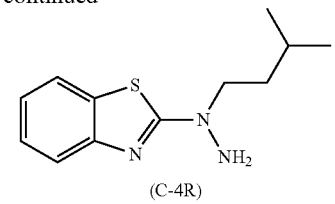
(C-4R)

Under a nitrogen atmosphere, 3.00 g of the compound represented by Formula (C-4R-1) and 20 mL of tetrahydrofuran were added to a reaction container. 11.4 mL of hexamethyldisilazane lithium (26% tetrahydrofuran solution) was added dropwise thereto at 0° C. and the mixture was stirred for 30 minutes. 2.9 mL of the compound represented by Formula (C-4R-2) was added thereto and the mixture was stirred at 25° C. for 6 hours. The resultant was poured into 100 mL of water and extracted with 150 mL of ethyl acetate. After drying over sodium sulfate, the solvent was distilled off. Purification was performed by column chromatography (silica gel) to obtain 2.07 g of a compound represented by Formula (C-4R).

(Example 5) Production of Compound Represented by Formula (C-5)

[Chem. 37]

Under a nitrogen atmosphere, 16.6 g of hydrazine monohydrate and 50 mL of ethanol were added to a reaction container, and the mixture was stirred at 80° C. A solution in which 15.0 g of the compound represented by Formula (C-5-1) was dissolved in 30 mL of ethanol was added dropwise thereto and the mixture was heated and stirred at 80° C. for 4 hours. Water was added and extraction was performed with dichloromethane. After the organic layer was washed with a saline solution, the resultant was dried over sodium sulfate and the solvent was distilled off to obtain 6.9 g of a compound represented by Formula (C-5-2).

Under a nitrogen atmosphere, 5.00 g of the compound represented by Formula (C-5-3), 3.6 g of triethylamine, and 60 mL of 1,2-dimethoxyethane were added to the reaction container. After 4.6 g of the compound represented by Formula (C-5-2) was added dropwise thereto, heating and stirring were carried out at 60° C. for 3 hours. The reaction solution was poured into a mixed solution of 200 mL of water and 50 mL of methanol, and the precipitated solid was filtered. After the solid was washed with water, the resultant was washed with hexane to obtain 4.7 g of a compound represented by Formula (C-5).

(Comparative Example 5) Production of Compound Represented by Formula (C-5R) by Method Described in PTL 3

[Chem. 38]

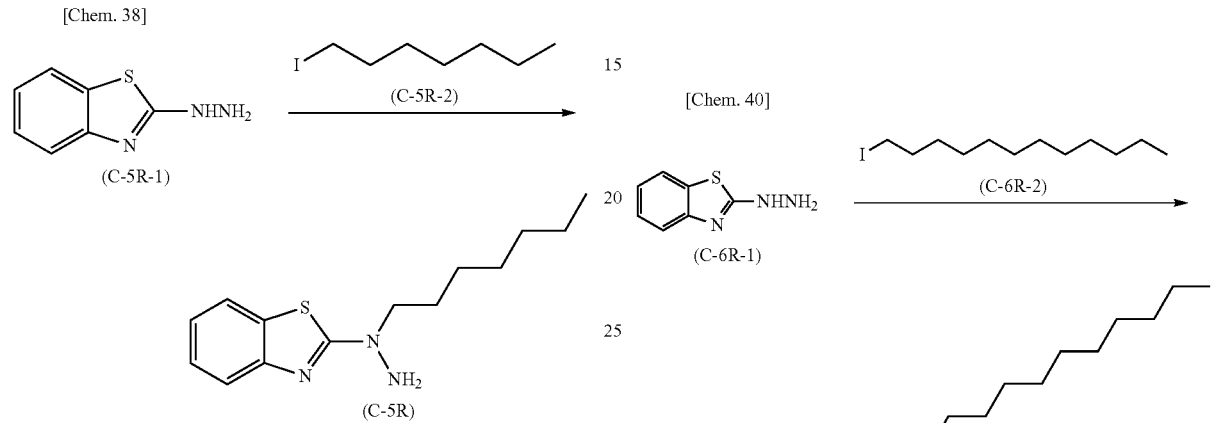

Under a nitrogen atmosphere, 2.00 g of the compound represented by Formula (C-5R-1), 30 mL of N,N-dimethylformamide, and 7.9 g of cesium carbonate were added to the reaction container. At 0° C., 3.3 mL of the compound represented by Formula (C-5R-2) was added thereto and the mixture was stirred at 25° C. for 3 hours. The resultant was poured into 200 mL of water and extracted with 200 mL of ethyl acetate. After drying over sodium sulfate, the solvent was distilled off. Purification was performed by column chromatography (silica gel) to obtain 1.8 g of a compound represented by Formula (C-5R).

(Example 6) Production of Compound Represented by Formula (C-6)

[Chem. 39]

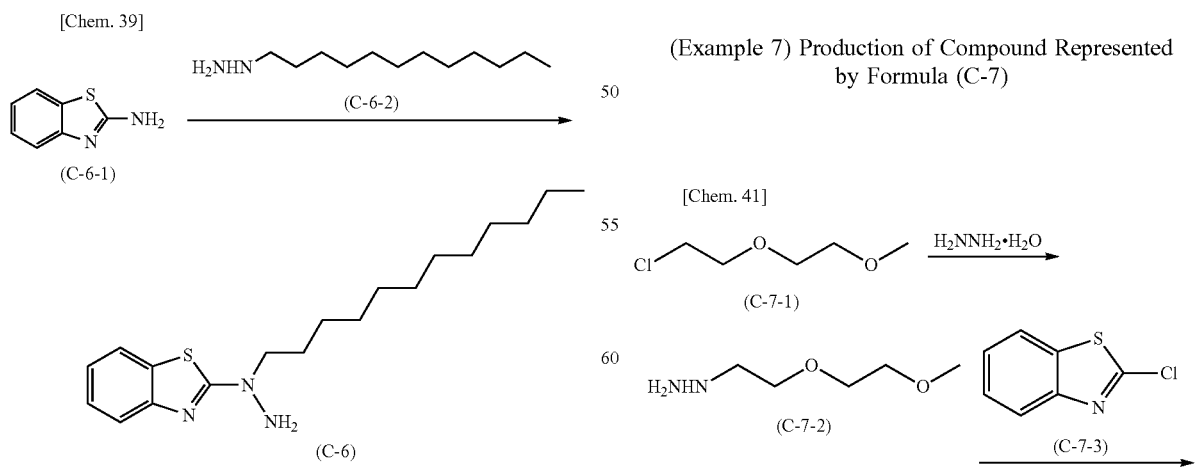

Under a nitrogen atmosphere, 5.0 g of the compound represented by Formula (C-6-1), 5.1 g of 1,8-diazabicyclo[5.4.0]-7-undecene, and 30 mL of 1,2-dimethoxyethane were added to the reaction container. After 6.7 g of the compound represented by Formula (C-6-2) was added dropwise thereto, heating and stirring were carried out. After performing a liquid separation treatment, purification was performed by column chromatography (alumina) to obtain 2.7 g of a compound represented by Formula (C-6).

(Comparative Example 6) Production of Compound Represented by Formula (C-6R) by Method Described in PTL 1

[Chem. 40]

Under a nitrogen atmosphere, 3.00 g of the compound represented by Formula (C-6R-1), 45 mL of N,N-dimethylformamide, 11.9 g of cesium carbonate, 6.5 g of the compound represented by Formula (C-6R-2) were added to a reaction container, and the mixture was stirred at 25° C. for 20 hours. The resultant was poured into 200 mL of water and extracted with 300 mL of ethyl acetate. After drying over sodium sulfate, the solvent was distilled off. Purification was performed by column chromatography (silica gel) to obtain 2.9 g of a compound represented by Formula (C-6R).

(Example 7) Production of Compound Represented by Formula (C-7)

[Chem. 41]

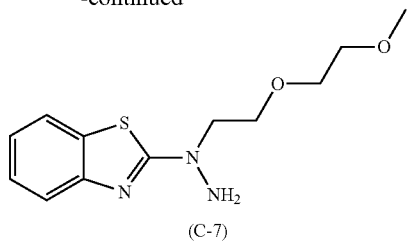

(C-7)

50 mL of hydrazine monohydrate and 150 mL of ethanol were added to the reaction container. 10.0 g of the compound represented by Formula (C-7-1) was added dropwise thereto and the mixture was heated and stirred. After the normal post-treatment was performed, distillation was carried out under reduced pressure to obtain 5.8 g of a compound represented by Formula (C-7-2).

7.3 g of the compound represented by Formula (C-7-3), 6.6 g of triethylamine, and 30 mL of 1,2-dimethoxyethane were added to the reaction container. After 5.8 g of the compound represented by Formula (C-7-2) and 20 mL of 1,2-dimethoxyethane were mixed and added dropwise thereto, heating and stirring were carried out. After a liquid separation treatment was performed, purification was performed by recrystallization to obtain 6.9 g of a compound represented by Formula (C-7).

$^1$H NMR (CDCl$_3$) δ 3.36 (s, 3H), 3.50 (t, 2H), 3.62 (t, 2H), 3.89 (t, 2H), 4.02 (t, 2H), 4.73 (s, 2H), 7.05 (t, 1H), 7.26 (t, 1H), 7.49 (d, 1H), 7.61 (d, 1H) ppm.

GCMS: m/z 267

(Example 8) Production of Compound Represented by Formula (C-8)

[Chem. 42]

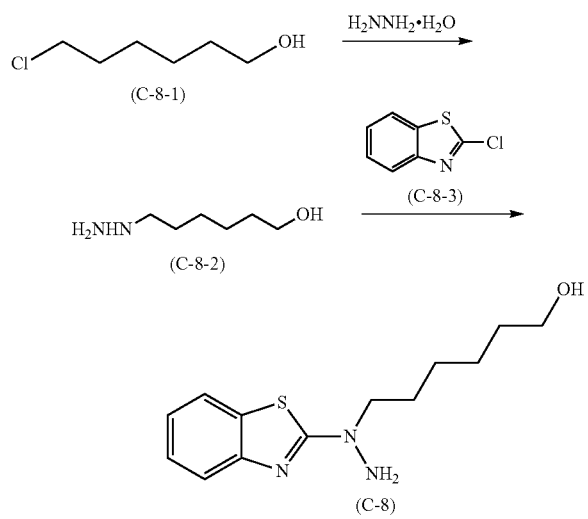

50 mL of hydrazine monohydrate and 120 mL of 2-propanol were added to the reaction container. 10.0 g of the compound represented by Formula (C-8-1) was added dropwise thereto and the mixture was heated and stirred. After the normal post-treatment was performed, distillation was performed under reduced pressure to obtain 6.8 g of the compound represented by Formula (C-8-2).

8.7 g of the compound represented by Formula (C-8-3), 7.8 g of triethylamine, and 30 mL of 1,2-dimethoxyethane were added to the reaction container. After 6.8 g of the compound represented by Formula (C-8-2) was added dropwise thereto, heating and stirring were carried out. After performing a liquid separation treatment, purification was performed by recrystallization to obtain 8.2 g of a compound represented by Formula (C-8).

GCMS: m/z 265

(Example 9) Production of Compound Represented by Formula (C-9)

[Chem. 43]

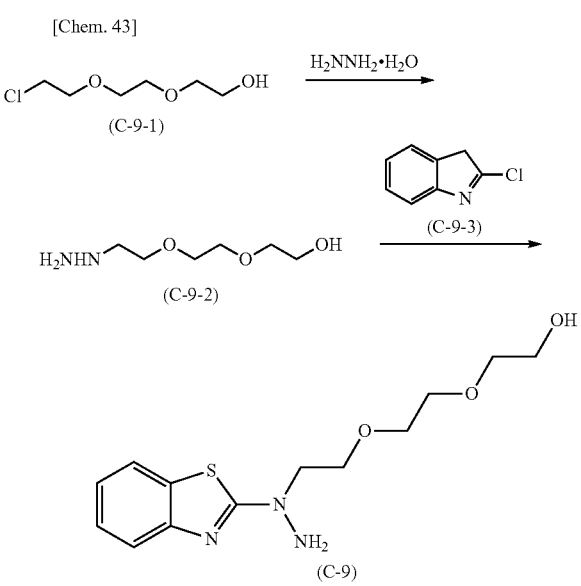

50 mL of hydrazine monohydrate and 130 mL of 1-propanol were added to the reaction container. 10.0 g of the compound represented by Formula (C-9-1) was added dropwise thereto and the mixture was heated and stirred. After the normal post-treatment was performed, distillation was performed under reduced pressure to obtain 5.9 g of a compound represented by Formula (C-9-2).

6.7 g of the compound represented by Formula (C-9-3), 7.8 g of triethylamine, and 30 mL of 1,2-dimethoxyethane were added to the reaction container. After 6.8 g of the compound represented by Formula (C-9-2) was added dropwise thereto, heating and stirring were carried out. After a liquid separation treatment was performed, purification was performed by recrystallization to obtain 4.5 g of a compound represented by Formula (C-9).

$^1$H NMR (CDCl$_3$) δ 3.56 (t, 2H), 3.60-3.66 (m, 4H), 3.73 (t, 2H), 3.90 (t, 2H), 4.00 (t, 2H), 4.82 (s, 2H), 7.06 (t, 1H), 7.27 (t, 1H), 7.51 (d, 1H), 7.60 (d, 1H) ppm GCMS: m/z 297

(Example 10) Production of Compound Represented by Formula (C-10)

[Chem. 44]

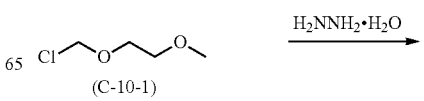

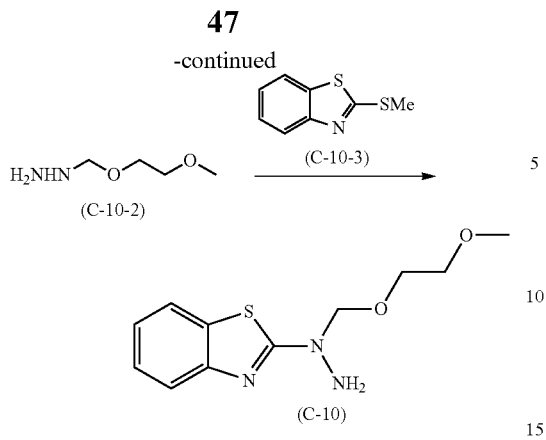

(C-10-2)  (C-10-3) → (C-10)

Under a nitrogen atmosphere, 48.2 g of hydrazine monohydrate and 200 mL of ethanol were added to the reaction container, and the mixture was stirred at 80° C. 15.0 g of the compound represented by Formula (C-10-1) was added dropwise thereto and the mixture was heated and stirred at 80° C. for 4 hours. The solvent was distilled off to obtain a mixture containing the compound represented by Formula (C-10-2).

Under a nitrogen atmosphere, 17.5 g of the compound represented by Formula (C-10-3), 11.7 g of triethylamine, and 50 mL of 1,2-dimethoxyethane were added to the reaction container. After adding a mixture containing the compound represented by Formula (C-10-2), the mixture was heated and stirred at 60° C. for 3 hours. The reaction solution was poured into 500 mL of water and extracted with 300 mL of dichloromethane. After washing with a saline solution and drying over sodium sulfate, the solvent was distilled off. Water was added for crystallization and filtration was carried out. After washing with water, the resultant was washed with hexane to obtain 9.6 g of a compound represented by Formula (C-10).

GCMS: m/z 253

Compounds represented by Formula (C-11) to Formula (C-22) were produced by the same method as described above.

[Chem. 45]

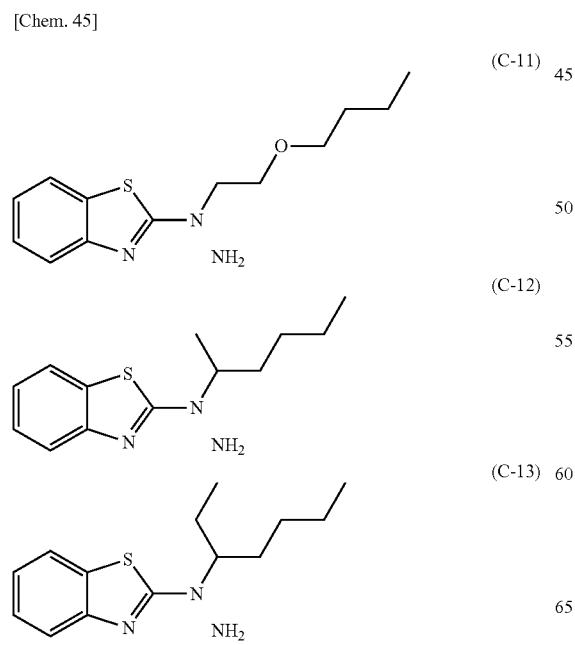

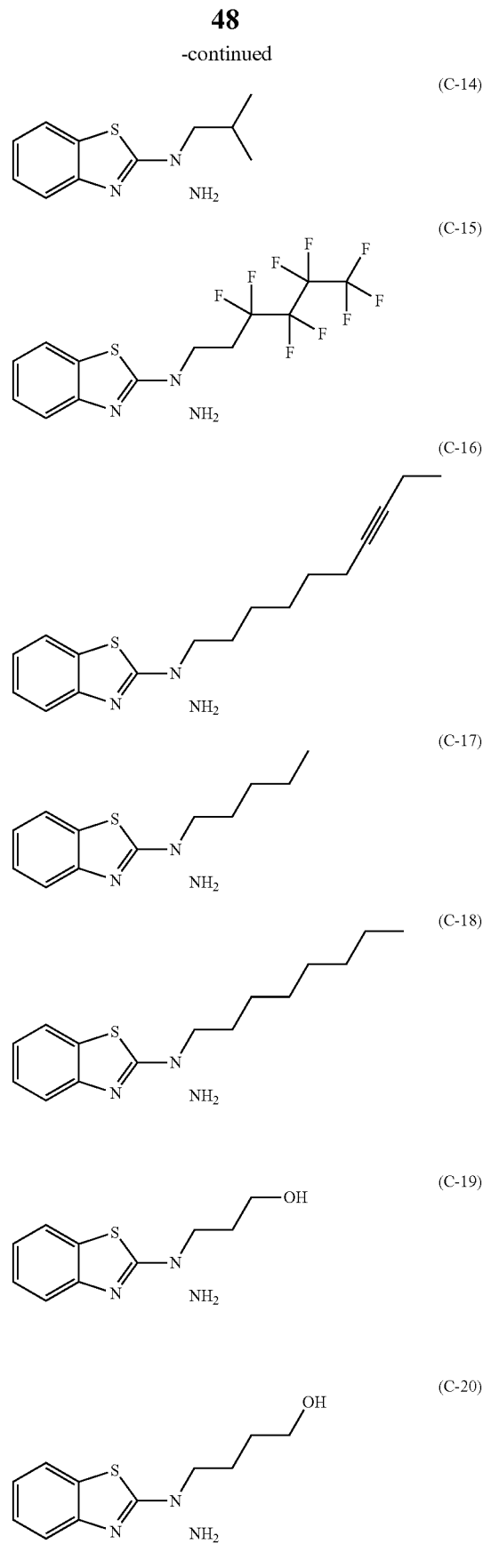

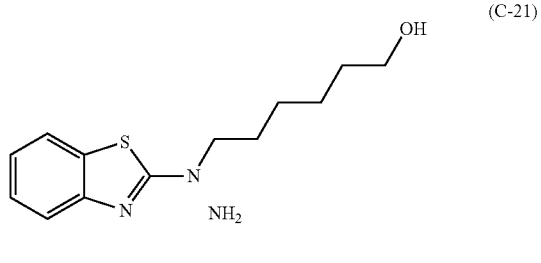

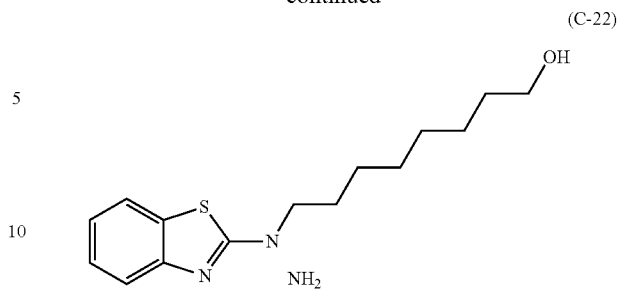

(Example 11) Production of Compound Represented by Formula (I-1)

[Chem. 46]

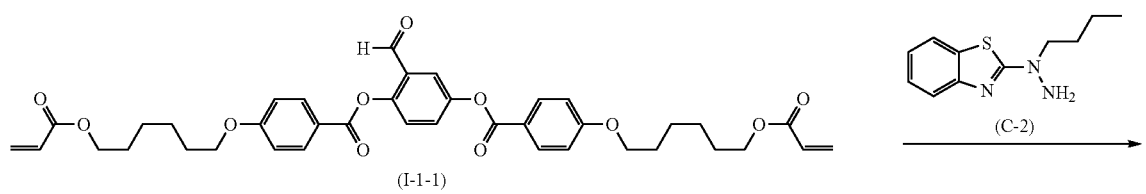

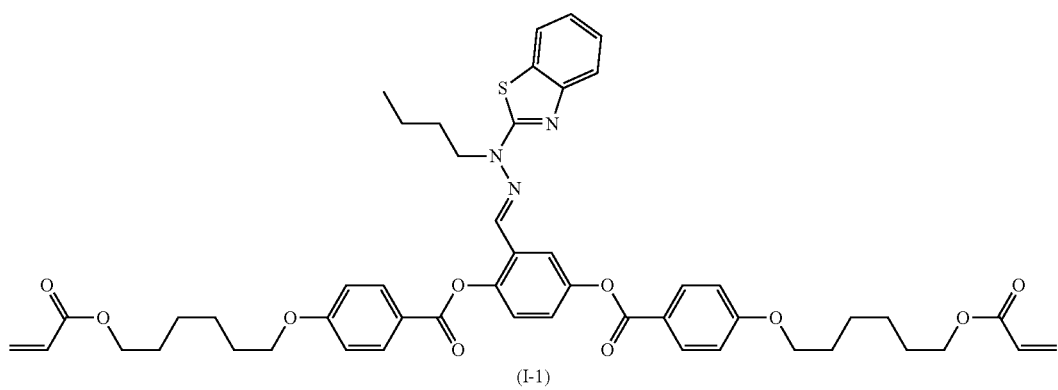

The compound represented by Formula (I-1-1) was produced by the method described in WO2012/147904A1. 3.00 g of the compound represented by Formula (I-1-1), 0.97 g of the compound represented by Formula (C-2) produced in Example 2, 0.10 g of p-toluenesulfonic acid monohydrate, 20 mL of tetrahydrofuran, and 10 mL of 2-propanol were added to a reaction container, and the mixture was heated and stirred at 50° C. The resultant was diluted with dichloromethane and washed with a saline solution. Purification was performed by column chromatography (silica gel) and recrystallization to obtain 2.33 g of a compound represented by Formula (I-1).

(Comparative Example 7) Production of Compound Represented by Formula (I-1R)

[Chem. 47]

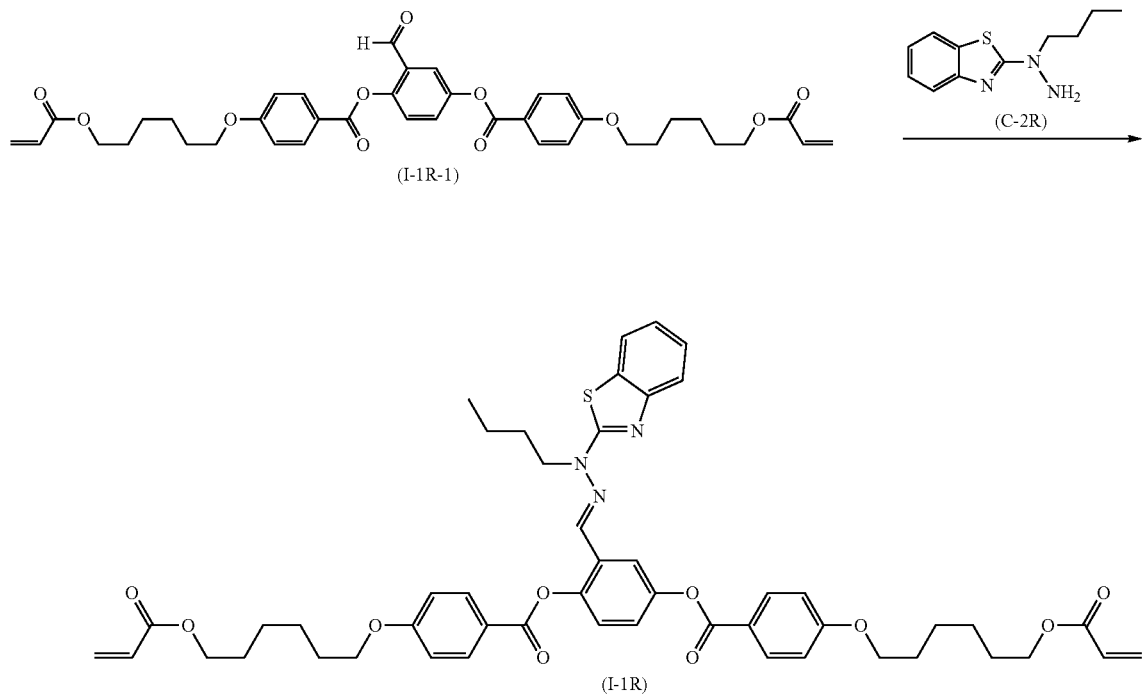

(I-1R)

By the same method as in Example 11, a compound represented by Formula (I-1R) was produced using the compound represented by Formula (C-2R) produced by the same method as in Comparative Example 2.

According to the same method as described above, using each of the compound represented by Formula (C-1) produced in Example 1, the compound represented by Formula (C-3) produced in Example 3, the compound represented by Formula (C-10) produced in Example 10, and the compound represented by Formula (C-4) produced in Example 4, the compounds represented by Formula (I-2) to Formula (I-5) were produced.

[Chem. 48]

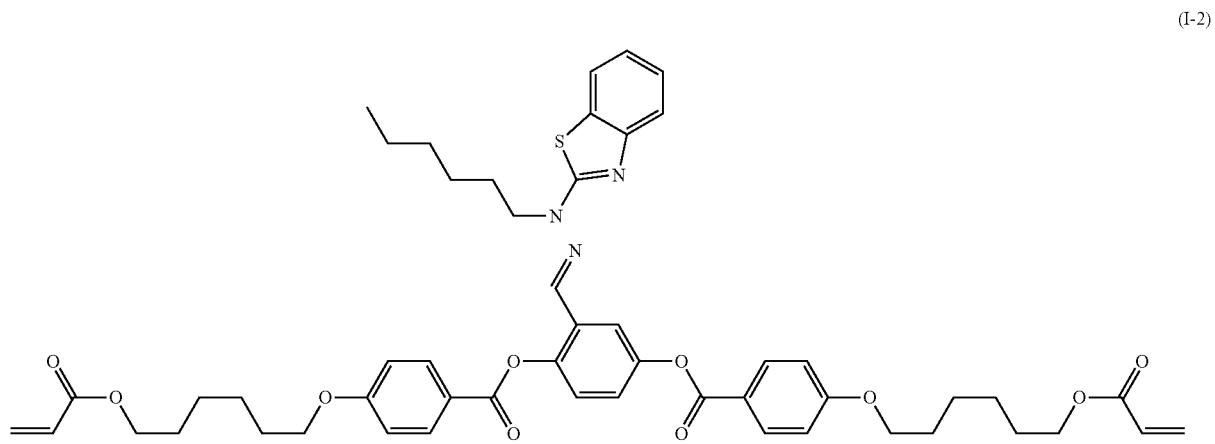

(I-2)

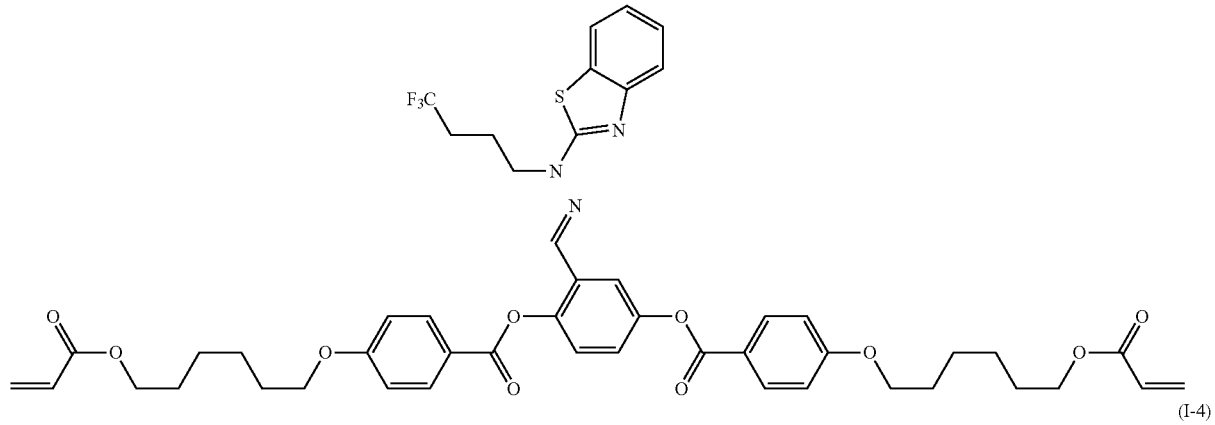

(I-3)

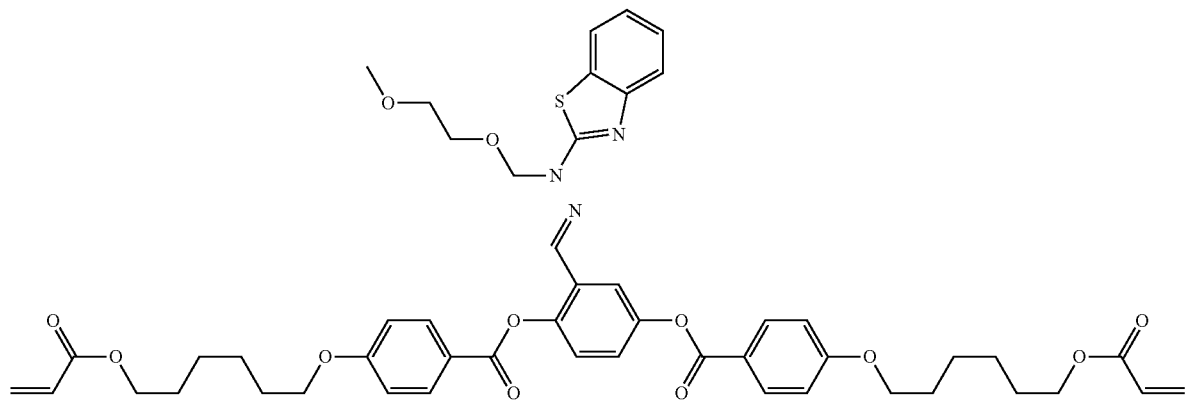

(I-4)

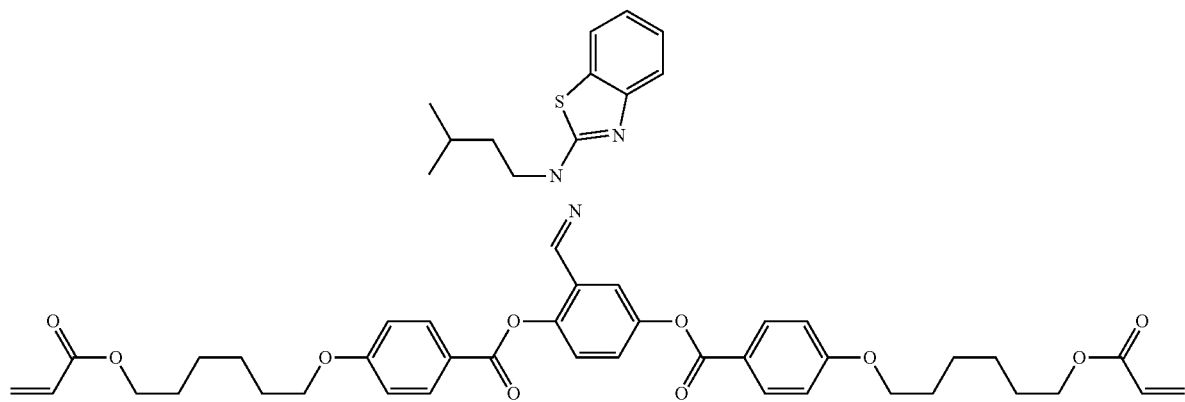

(I-5)

According to the same method as described above, using each of the compound represented by Formula (C-1R) produced in Comparative Example 1, the compound represented by Formula (C-3R) produced in Comparative Example 3, the compound represented by Formula (C-10R) produced in Comparative Example 10, and the compound represented by Formula (C-4R) produced in Comparative Example 4, the compounds represented by Formula (I-2R) to Formula (I-5R) were produced.

[Chem. 49]
(I-2R)
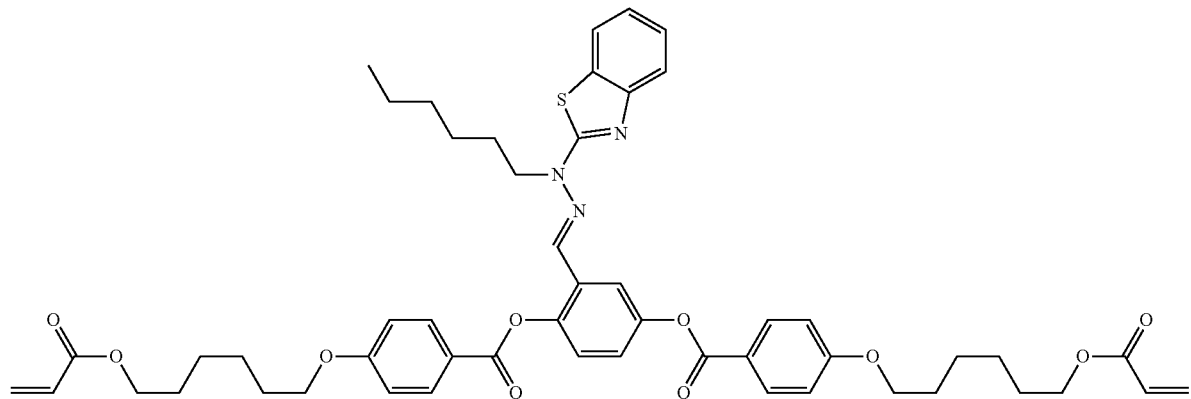
(I-3R)
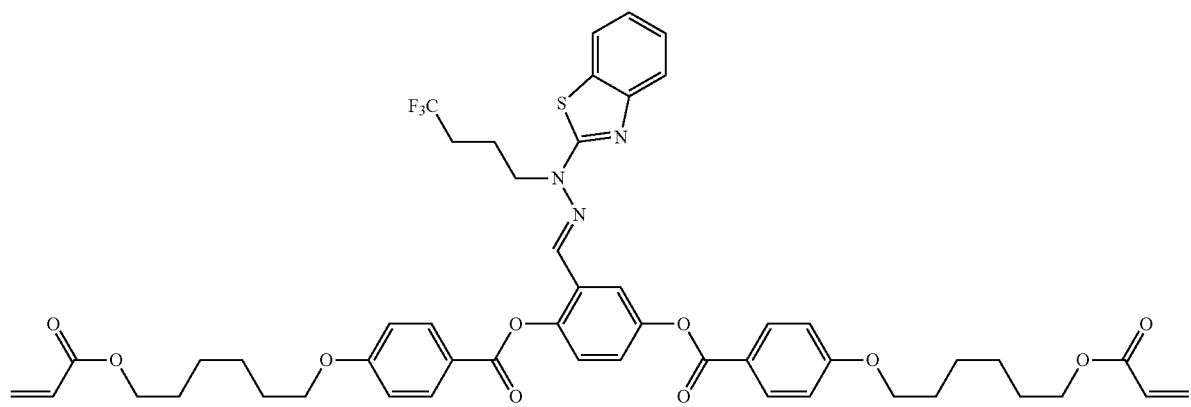
(I-4R)
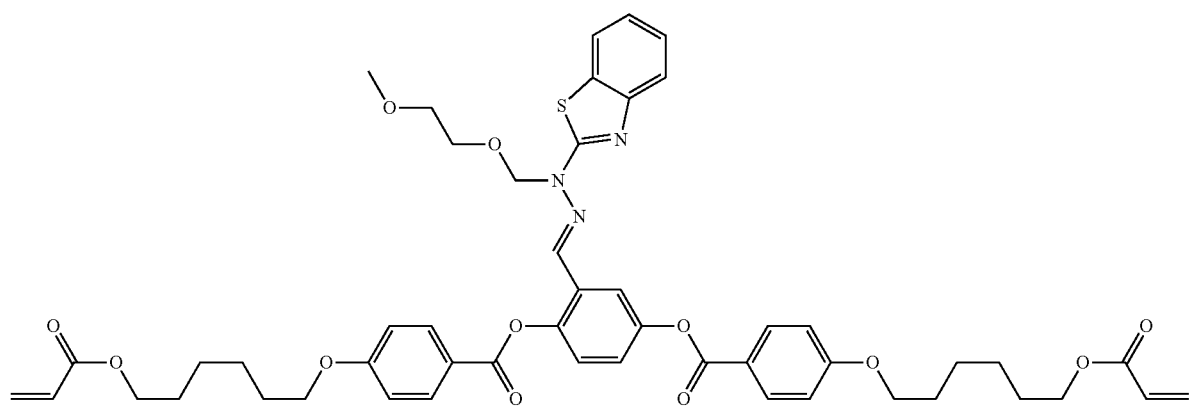

(I-5R)
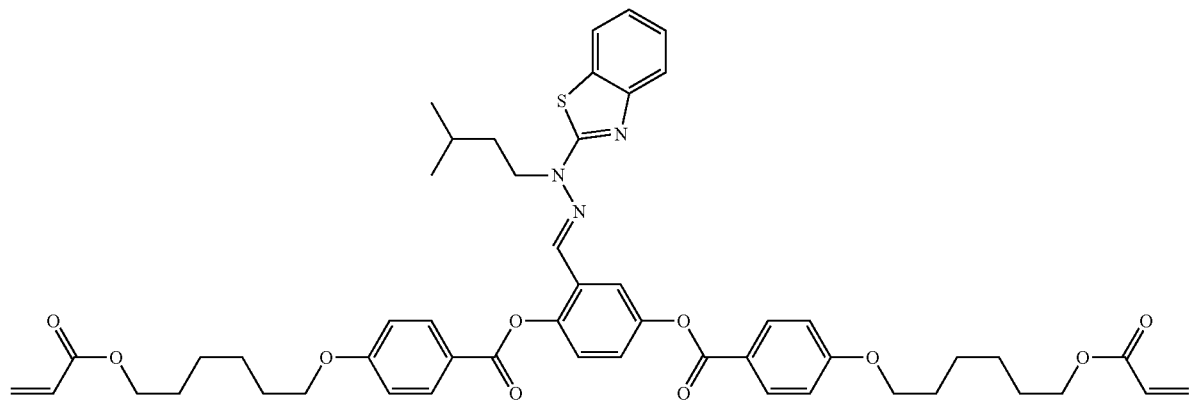
20
(Example 12) Production of Compound Represented by Formula (I-6)

[Chem. 50]
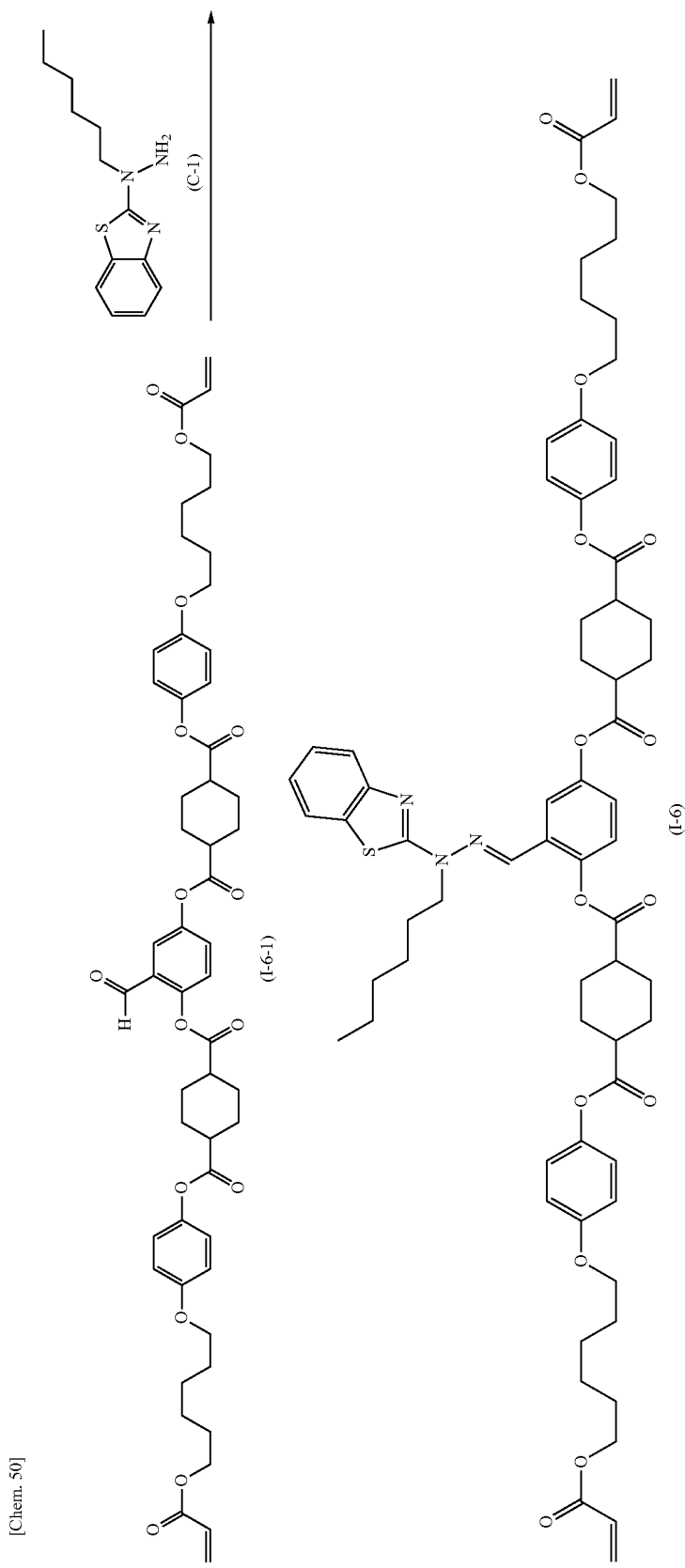

The compound represented by Formula (I-6-1) was produced by the method described in WO2014/010325A1. 3.0 g of the compound represented by Formula (I-6-1), 0.8 g of the compound represented by Formula (C-1) produced by the method described in Example 1, 0.5 g of (±)-10-camphorsulfonic acid, 30 mL of tetrahydrofuran, and 15 mL of ethanol, were added to a reaction container purged with nitrogen, and the mixture was heated and stirred at 50° C. After distilling off the solvent, methanol was added thereto and the precipitated solid was filtered. Purification was performed by column chromatography (silica gel) and recrystallization (dichloromethane/methanol) to obtain 2.6 g of a compound represented by Formula (I-6).

(Comparative Example 8) Production of Compound Represented by Formula (I-6R)

[Chem. 51]
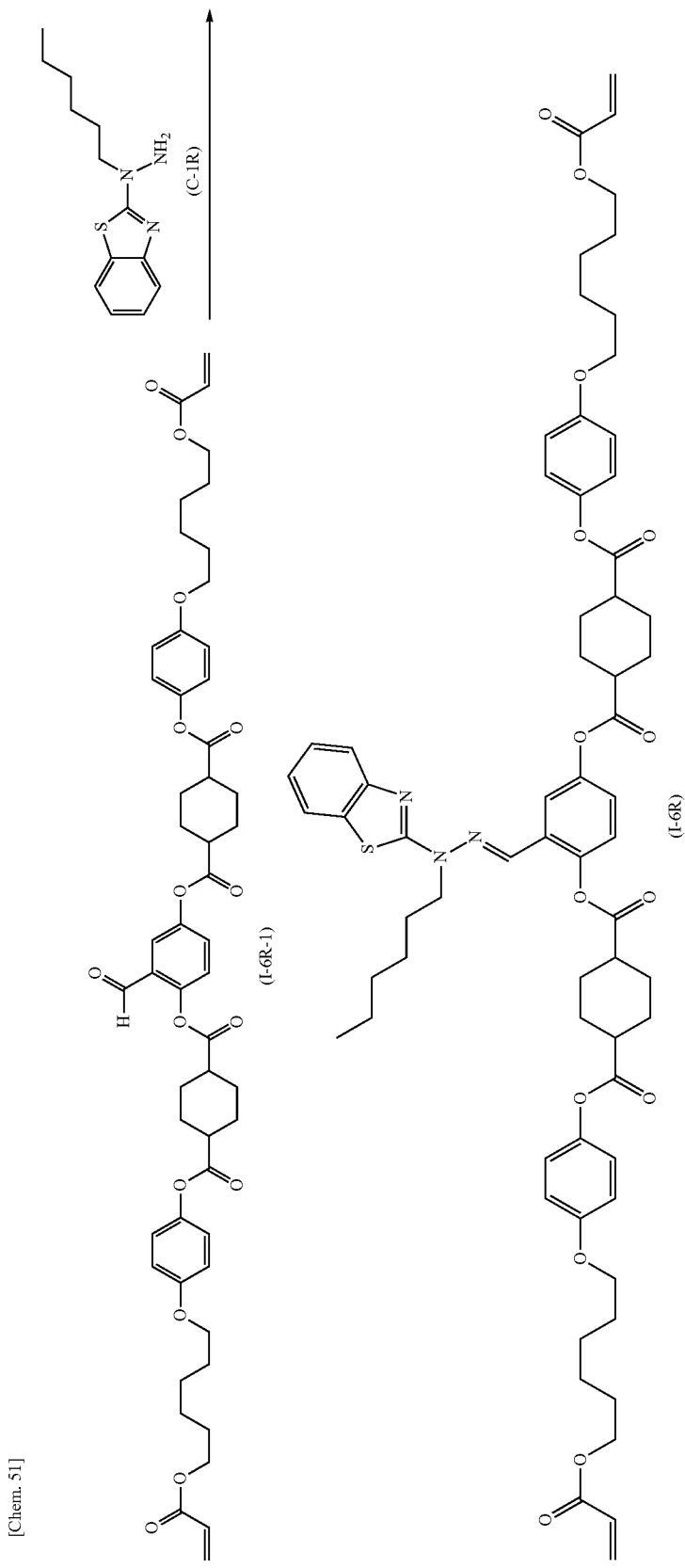

Using the same method as in Example 12, the compound represented by Formula (I-6R) was produced using the compound represented by Formula (C-1R) produced by the same method as in Comparative Example 1.

According to the same method as described above, using each of the compound represented by Formula (C-5) produced by the method described in Example 5, the compound represented by Formula (C-6) produced by the method described in Example 6, the compound represented by Formula (C-10) produced by the method described in Example 10, and the compound represented by Formula (C-3) produced by the method described in Example 3, the compounds represented by Formula (I-7) to Formula (I-10) were produced.

[Chem. 52]

(I-7)

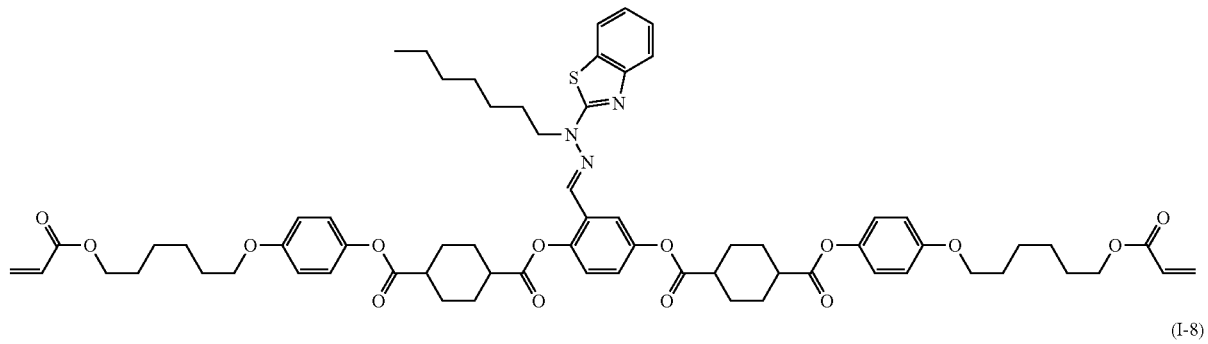

(I-8)

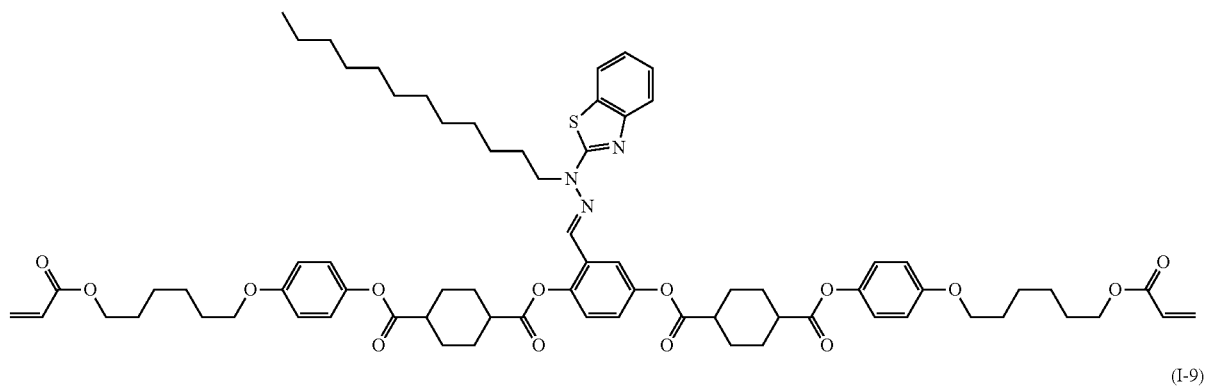

(I-9)

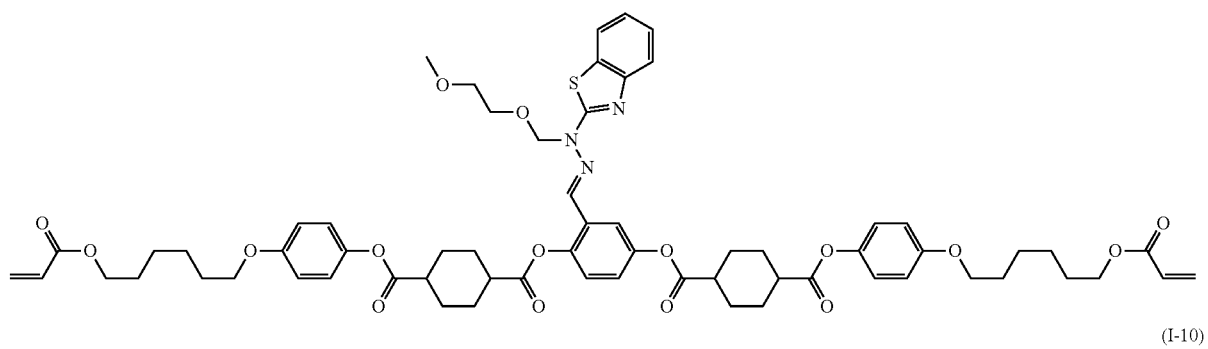

(I-10)

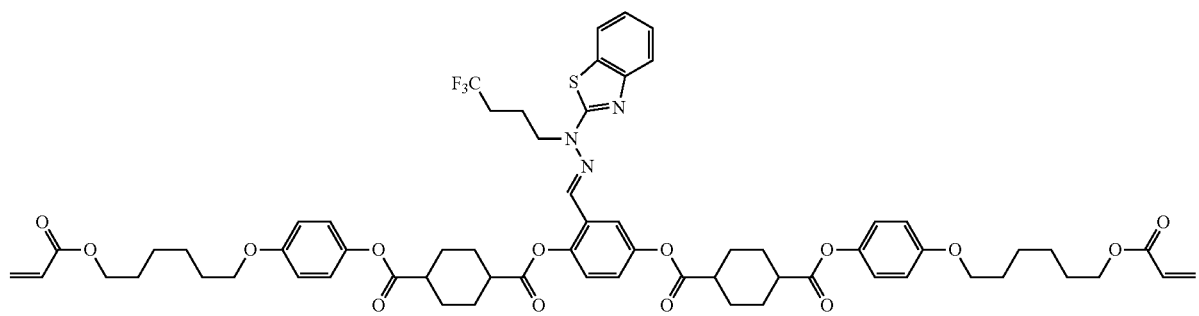

According to the same method as described above, using each of the compound represented by Formula (C-5R) produced by the method described in Comparative Example 5, the compound represented by Formula (C-6R) produced by the method described in Comparative Example 6, and the compound represented by Formula (C-3R) produced by the method described in Comparative Example 3, the compounds represented by Formula (I-7R), Formula (I-8R), and Formula (I-10R) were produced.

[Chem. 53]

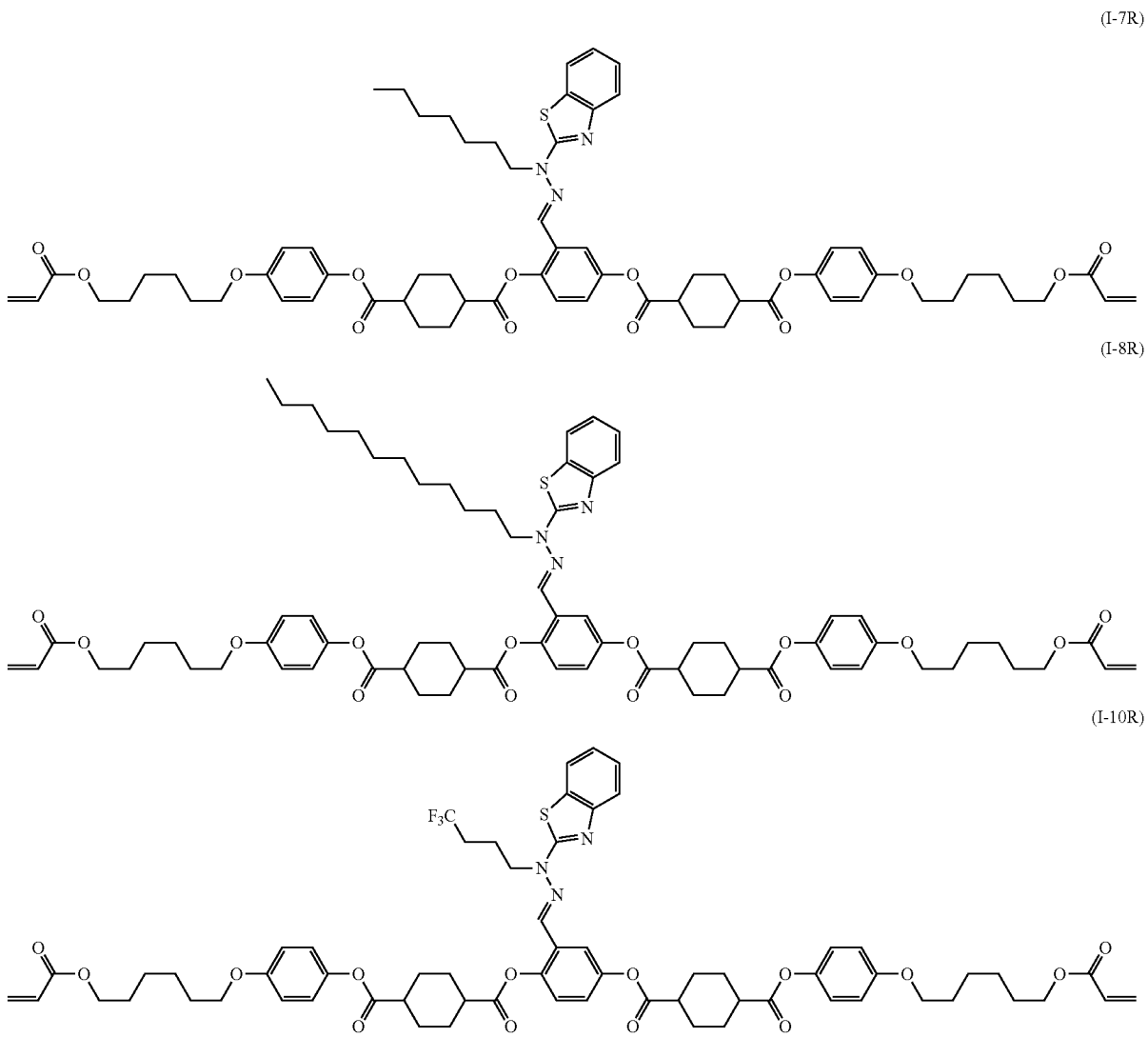

(I-7R)

(I-8R)

(I-10R)

(Example 13) Production of Compound Represented by Formula (I-11)

[Chem. 54]

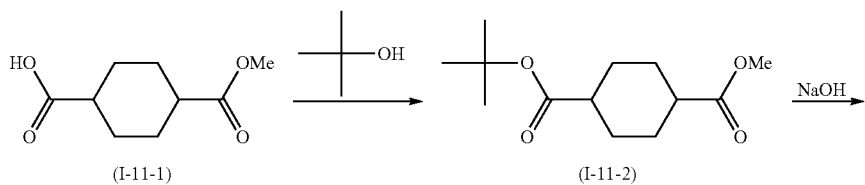

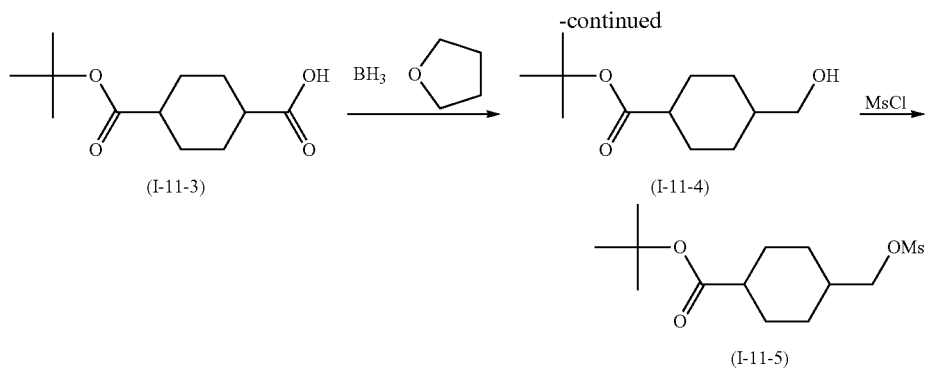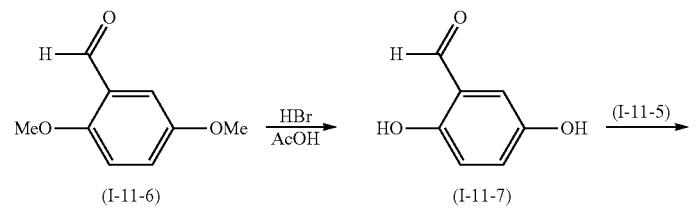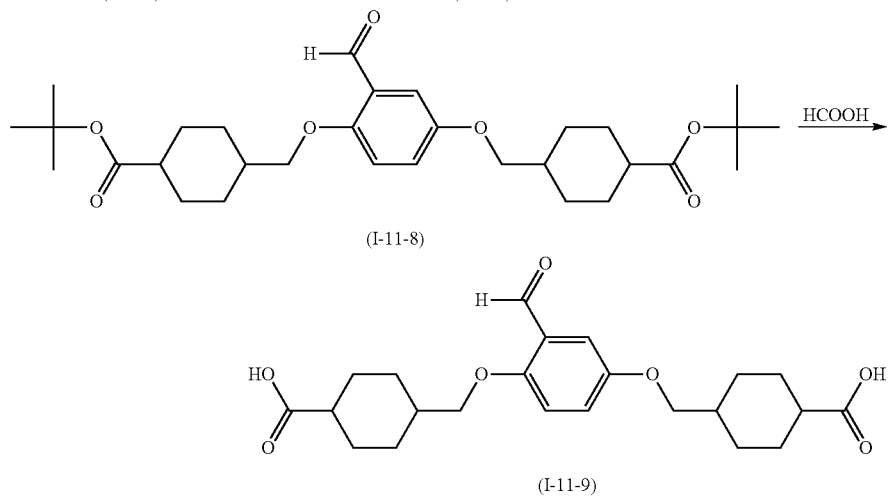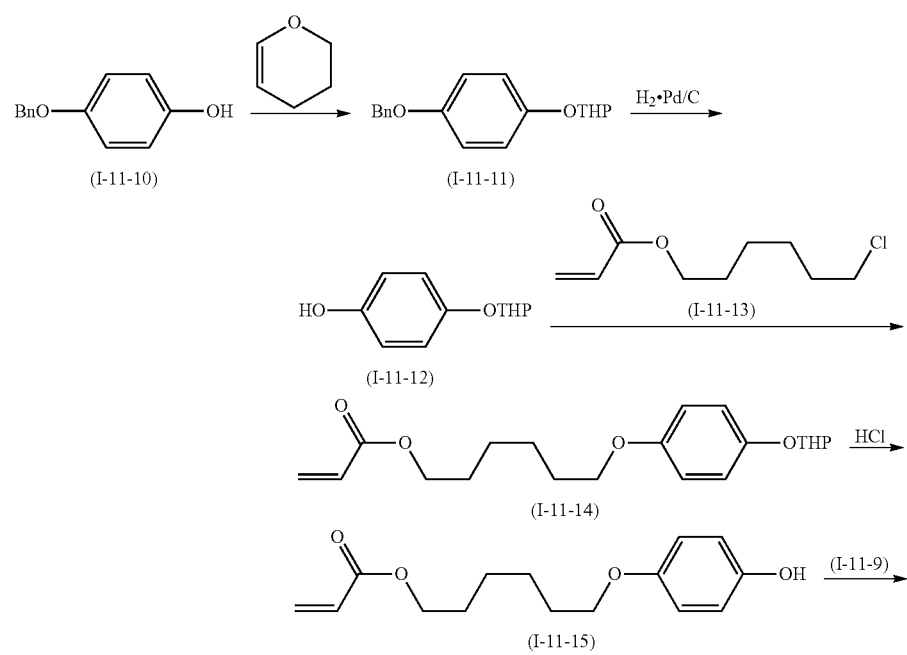

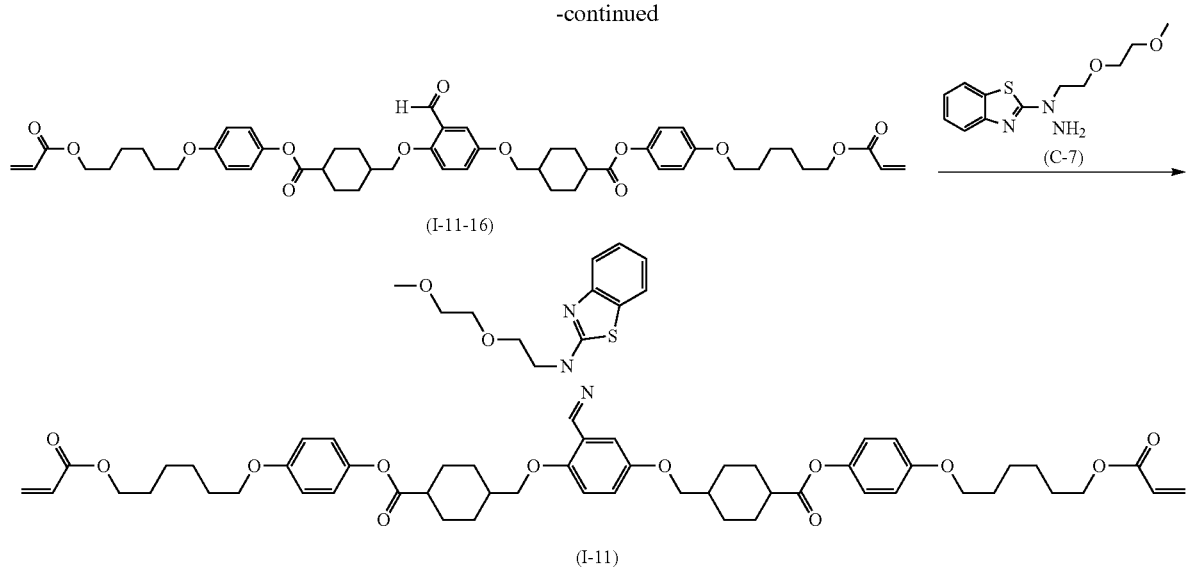

Under a nitrogen atmosphere, 20.0 g of the compound represented by Formula (I-11-1), 9.6 g of tert-butyl alcohol, 0.7 g of 4-dimethylaminopyridine, and 160 mL of dichloromethane were added to a reaction container. 16.3 g of diisopropylcarbodiimide was added dropwise thereto while cooling with ice, and the mixture was stirred at room temperature for 8 hours. The precipitate was removed by filtration and washed with 5% hydrochloric acid and a saline solution. Purification was performed by column chromatography (silica gel, dichloromethane/hexane) to obtain 24.7 g of a compound represented by Formula (I-11-2).

24.7 g of the compound represented by Formula (I-11-2), 200 mL of methanol, and 33 mL of 25% sodium hydroxide aqueous solution were added to the reaction container, and the mixture was stirred at room temperature for 8 hours. After neutralization with 5% hydrochloric acid, the mixture was extracted with ethyl acetate and dried over sodium sulfate to obtain 22.1 g of a compound represented by Formula (I-11-3).

Under a nitrogen atmosphere, 20.0 g of the compound represented by Formula (I-11-3) and 120 mL of tetrahydrofuran were added to the reaction container. 105 mL of a borane-tetrahydrofuran complex (1 mol/L) was added dropwise thereto while cooling with ice, and the mixture was stirred for 2 hours. After adding 100 mL of 5% hydrochloric acid dropwise thereto, a liquid phase separation treatment was performed with 200 mL of ethyl acetate. After drying over sodium sulfate, the solvent was distilled off to obtain 16.9 g of a compound represented by Formula (I-11-4).

Under a nitrogen atmosphere, 16.9 g of the compound represented by Formula (I-11-4), 7.5 g of pyridine, and 100 mL of dichloromethane were added to the reaction container. 10.8 g of methanesulfonyl chloride was added dropwise thereto while cooling with ice, and the mixture was stirred at room temperature for 24 hours. After being poured into 5% hydrochloric acid, a liquid separation treatment was carried out. Purification was performed by column chromatography (silica gel) to obtain 20.7 g of a compound represented by Formula (I-11-5).

Under a nitrogen atmosphere, 20.0 g of a compound represented by Formula (I-11-6), 60 mL of 48% hydrobromic acid, and 60 mL of acetic acid were added to a reaction container, and the mixture was heated under reflux for 6 hours. After cooling, a liquid separation treatment was carried out with 200 mL of ethyl acetate. Purification was performed by column chromatography (alumina) to obtain 14.6 g of a compound represented by Formula (I-11-7).

Under a nitrogen atmosphere, 1.0 g of the compound represented by Formula (I-11-7), 4.2 g of the compound represented by Formula (I-11-5), 3.8 g of potassium phosphate, 20 mL of N,N-dimethylformamide were added to a reaction container, and the mixture was heated and stirred at 90° C. for 8 hours. After the reaction solution was poured into 100 mL of water, the precipitated solid was filtered and washed with water. Purification was performed by column chromatography (silica gel, dichloromethane) and recrystallization (dichloromethane/methanol) to obtain 3.1 g of a compound represented by Formula (I-11-8).

Under a nitrogen atmosphere, 3.1 g of a compound represented by Formula (I-11-8), 30 mL of dichloromethane, and 30 mL of formic acid were added to a reaction container, and the mixture was heated and stirred at 40° C. for 8 hours. After distilling off the solvent, 30 mL of diisopropyl ether was added thereto and stirred, and the precipitate was filtered. The obtained solid was washed with diisopropyl ether to obtain 2.2 g of a compound represented by Formula (I-11-9).

10.0 g of the compound represented by Formula (I-11-10), 0.7 g of pyridinium p-toluenesulfonate, and 100 mL of dichloromethane were added to the reaction container. 4.6 g of 3,4-dihydro-2H-pyran was added dropwise thereto while cooling with ice, and the mixture was stirred at room temperature for 7 hours. After washing with a 5% sodium bicarbonate aqueous solution and a saline solution, purification was performed by column chromatography (alumina) to obtain 13.5 g of a compound represented by Formula (I-11-11).

13.5 g of a compound represented by Formula (I-11-11), 0.1 g of 5% palladium carbon, 50 mL of tetrahydrofuran, and 50 mL of ethanol were added to a pressure-resistant container. The mixture was heated and stirred at 50° C. for 8 hours under a hydrogen pressure of 0.5 MPa. After filtration of the catalyst, the solvent was distilled off to obtain 8.8 g of a compound represented by Formula (I-11-12).

15.0 g of the compound represented by Formula (I-11-12), 17.7 g of the compound represented by Formula (I-11-13), 16.0 g of potassium carbonate, and 90 mL of N,N-dimethylformamide were added to the reaction container, and the mixture was heated and stirred at 90° C. for 20 hours. Dichloromethane (150 mL) was added thereto and a liquid separation treatment was performed. Purification was performed by column chromatography (silica gel) to obtain 24.2 g of a compound represented by Formula (I-11-14).

24.2 g of the compound represented by Formula (I-11-14), 80 mL of tetrahydrofuran, and 80 mL of methanol were added to the reaction container. 1 mL of concentrated hydrochloric acid was added thereto and the mixture was stirred at room temperature for 10 hours. After distilling off the solvent, the mixture was subjected to a liquid separation treatment with 150 mL of ethyl acetate. Purification was performed by column chromatography (alumina) and recrystallization (ethyl acetate/hexane) to obtain 17.4 g of a compound represented by Formula (I-11-15).

Under a nitrogen atmosphere, 1.9 g of the compound represented by Formula (I-11-9), 2.4 g of the compound represented by Formula (I-11-15), 0.06 g of N,N-dimethylaminopyridine, and 20 mL of dichloromethane were added to the reaction container. 2.2 g of 1-ethyl-3-(3-dimethylaminopropyl) carbodiimide hydrochloride was added while cooling with ice, and the mixture was stirred at room temperature for 8 hours. The reaction solution was washed with 5% hydrochloric acid and a saline solution. Purification was performed by column chromatography (silica gel) and recrystallization (dichloromethane/methanol) to obtain 3.3 g of a compound represented by Formula (I-11-16).

3.3 g of the compound represented by Formula (I-11-16), 1.0 g of the compound represented by Formula (C-7) produced by the method described in Example 7, 0.5 g of (±)-10-camphorsulfonic acid, 30 mL of tetrahydrofuran, and 15 mL of ethanol were added to a reaction container purged with nitrogen and the mixture was heated and stirred at 50° C. for 8 hours. After distilling off the solvent, methanol was added to cause crystallization and filtration was carried out. Purification was performed by column chromatography (silica gel) and recrystallization (dichloromethane/methanol) to obtain 2.9 g of a compound represented by Formula (I-11).

Transition temperature (temperature rise 5° C./min): C, 85 N, 128 I $^1$H NMR (CDCl$_3$) δ 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

(Example 14) Production of Compound Represented by Formula (I-12)

[Chem. 56]

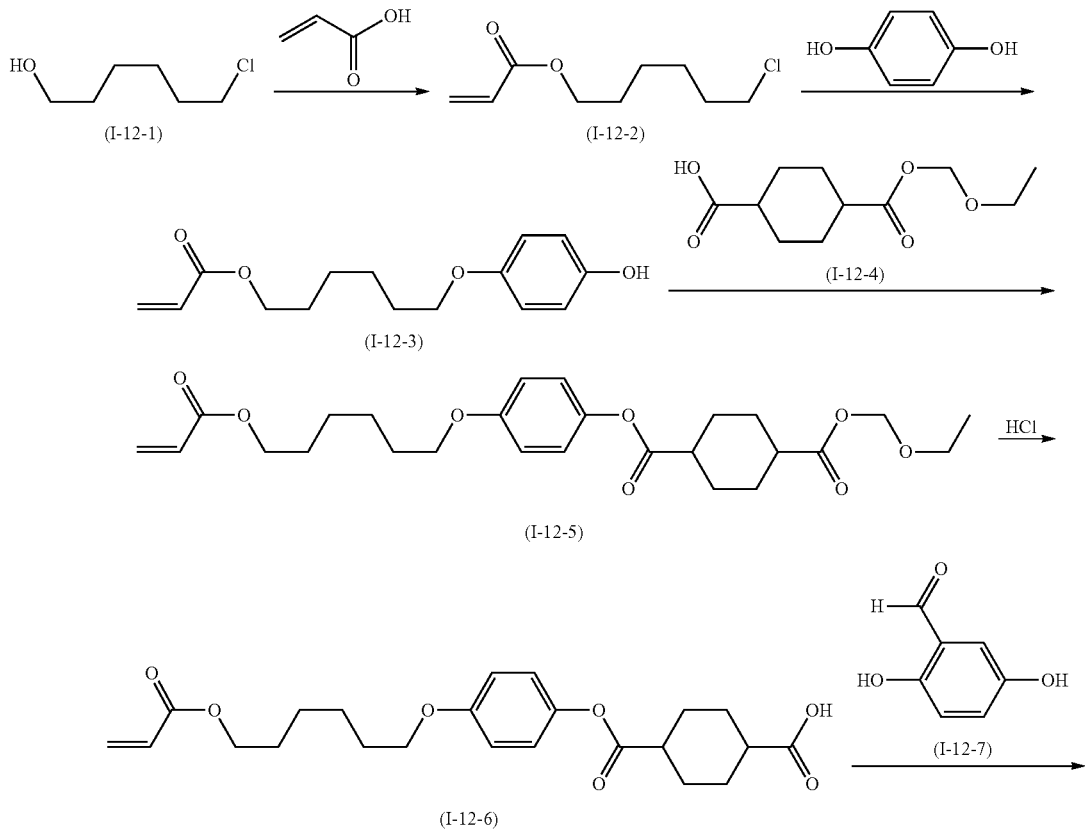

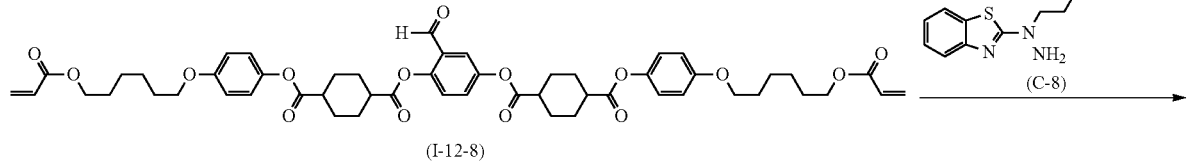

(I-12-8)

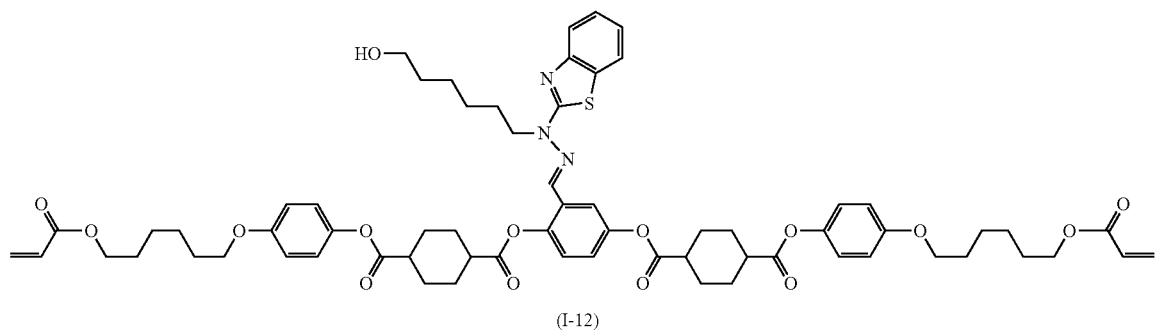

(I-12)

20.0 g of the compound represented by Formula (I-12-1), 15.8 g of acrylic acid, 2.8 g of p-toluenesulfonic acid monohydrate, and 150 mL of toluene were added to a reaction container equipped with a Dean-Stark apparatus and heated under reflux for 8 hours while dehydrating. After cooling, the resultant was washed with a 5% sodium bicarbonate aqueous solution and a saline solution. Purification was performed by column chromatography (silica gel) to obtain 25.1 g of a compound represented by Formula (I-12-2).

10.0 g of the compound represented by Formula (I-12-2), 28.9 g of hydroquinone, 18.1 g of potassium carbonate, and 80 mL of acetone were added to the reaction container, and the mixture was heated under reflux for 6 hours. After cooling, the solid was filtered and the solvent was distilled off. 150 mL of ethyl acetate was added thereto, and the mixture was washed with 5% hydrochloric acid and a saline solution. Purification was performed by column chromatography (silica gel) and recrystallization (ethyl acetate/hexane) to obtain 9.7 g of a compound represented by Formula (I-12-3).

The compound represented by Formula (I-12-4) was produced by the method described in WO2011/068138A1. Under a nitrogen atmosphere, 5.0 g of the compound represented by Formula (I-12-3), 4.4 g of the compound represented by Formula (I-12-4), 0.2 g of N,N-dimethylaminopyridine, and 40 mL of dichloromethane were added to a reaction container. 2.9 g of diisopropylcarbodiimide was added dropwise thereto while cooling with ice and stirred. After the precipitate was filtered, the filtrate was washed with 5% hydrochloric acid and a saline solution. Purification was performed by column chromatography (alumina) and recrystallization (dichloromethane/methanol) to obtain 7.2 g of a compound represented by Formula (I-12-5).

7.2 g of the compound represented by Formula (I-12-5), 30 mL of tetrahydrofuran, 30 mL of methanol, and 1 mL of concentrated hydrochloric acid were added to the reaction container, and the mixture was stirred at room temperature for 7 hours. The resultant was diluted with 150 mL of ethyl acetate and washed with a saline solution. Purification was performed by column chromatography (alumina) and dispersion washing (hexane) to obtain 6.0 g of a compound represented by Formula (I-12-6).

Under a nitrogen atmosphere, 4.0 g of the compound represented by Formula (I-12-6), 0.7 g of the compound represented by Formula (I-12-7), 0.1 g of N,N-dimethylaminopyridine, and 40 mL of dichloromethane were added to a reaction container. 1.5 g of diisopropylcarbodiimide was added dropwise thereto while cooling with ice, and the mixture was stirred at room temperature for 8 hours. After filtration of the solid, the filtrate was washed with a 5% hydrochloric acid and a saline solution. Purification was performed by column chromatography (silica gel) and recrystallization (dichloromethane/methanol) to obtain 3.3 g of a compound represented by Formula (I-12-8).

Under a nitrogen atmosphere, 3.3 g of the compound represented by Formula (I-12-8), 0.9 g of the compound represented by Formula (C-8) produced by the method described in Example 8, 0.5 g of (±)-10-camphorsulfonic acid, 30 mL of tetrahydrofuran, and 15 mL of ethanol were added to a reaction container, and the mixture was heated and stirred at 50° C. After distilling off the solvent, methanol was added thereto, and crystallization and filtration were carried out. Purification was performed by column chromatography (silica gel) and recrystallization (dichloromethane/methanol) to obtain 2.3 g of a compound represented by Formula (I-12).

LCMS: 1186 [M+1]

(Example 15) Production of Compound Represented by Formula (I-13)

[Chem. 57]

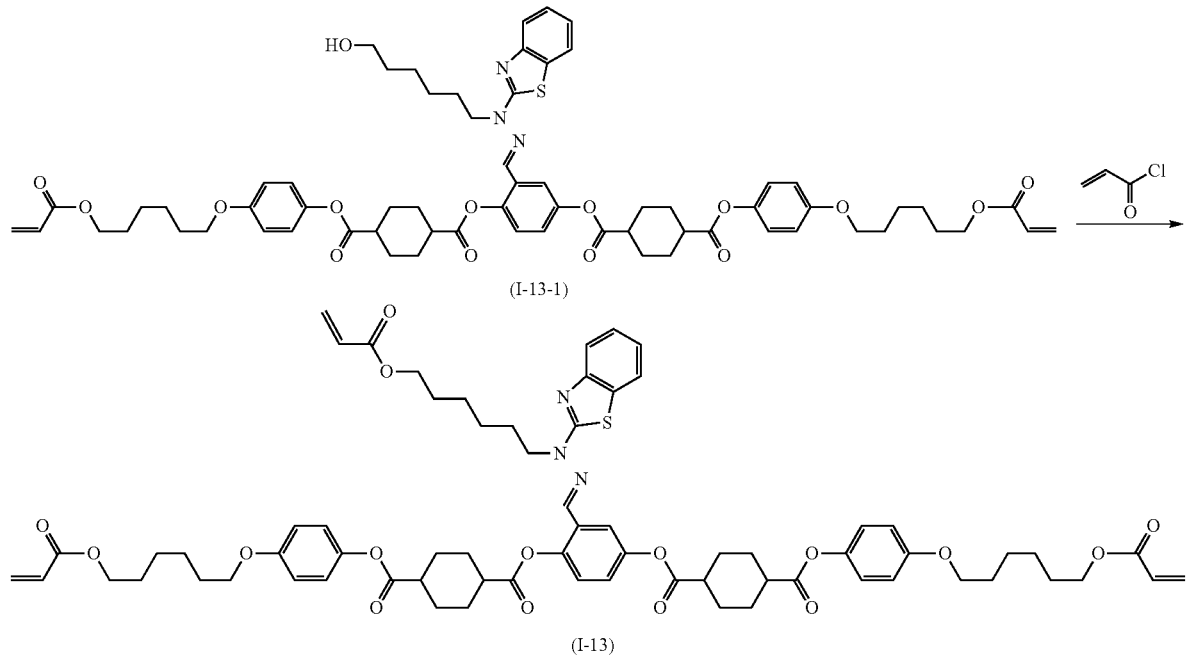

(I-13-1)

(I-13)

Under a nitrogen atmosphere, 3.0 g of the compound represented by Formula (I-13-1), 0.5 g of diisopropylethylamine, and 30 mL of dichloromethane were added to the reaction container. 0.3 g of acryloyl chloride was added dropwise thereto while cooling with ice, and the mixture was stirred at room temperature for 5 hours. After washing with 1% hydrochloric acid and a saline solution, purification was performed by column chromatography (silica gel) and recrystallization (dichloromethane/methanol) to obtain 2.2 g of a compound represented by Formula (I-13).

$^1$H NMR (CDCl$_3$) δ 1.24 (m, 4H), 1.48-1.93 (m, 30H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1212 [M+1]

(Example 16) Preparation of Compound Represented by Formula (I-14)

[Chem. 58]
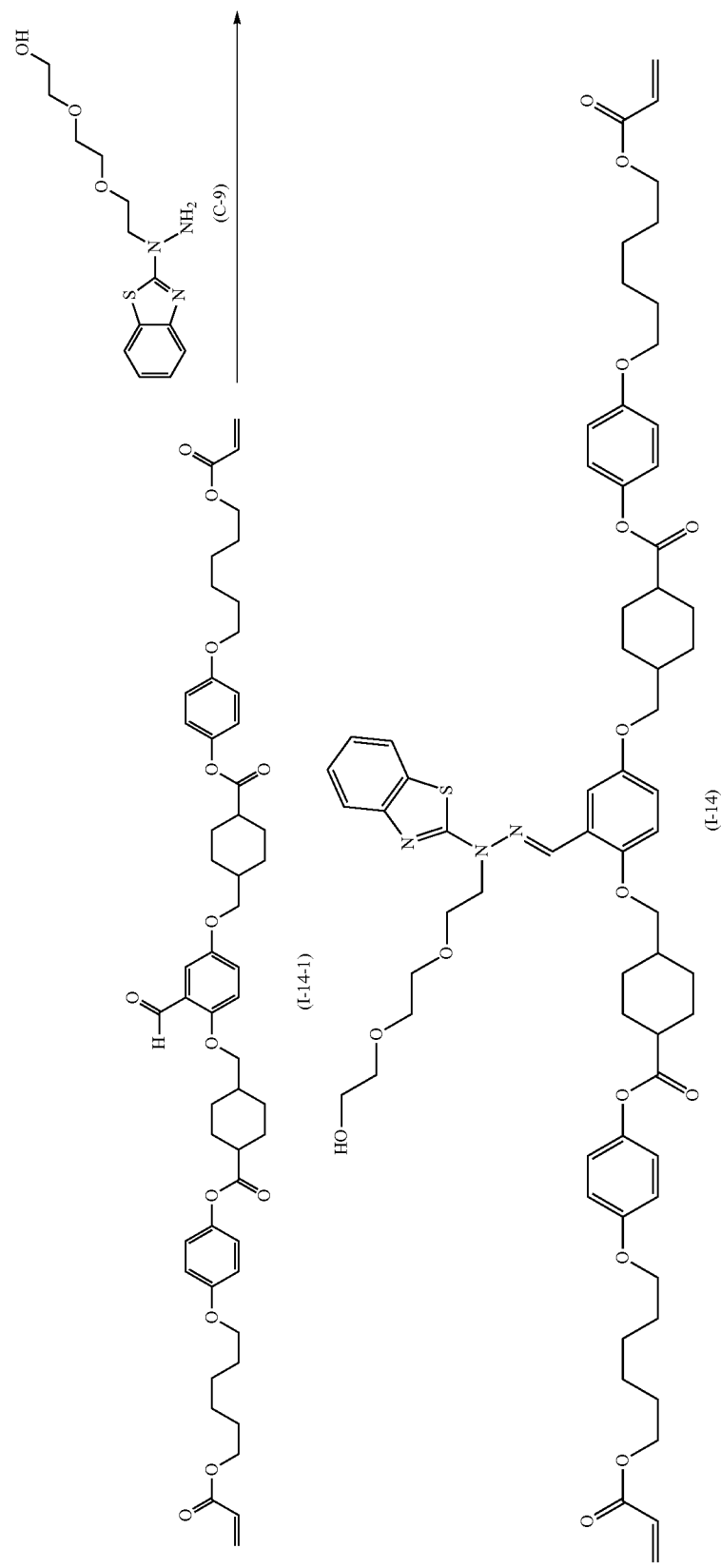

Under a nitrogen atmosphere, 3.0 g of the compound represented by Formula (I-14-1), 1.0 g of the compound represented by Formula (C-9) produced by the method described in Example 9, 0.5 g of (±)-10-camphorsulfonic acid, 30 mL of tetrahydrofuran, and 15 mL of ethanol were added to a reaction container, and the mixture was heated and stirred at 50° C. After distilling off the solvent, methanol was added to cause crystallization and filtration was carried out. Purification was performed by column chromatography (silica gel) and recrystallization (dichloromethane/methanol) to obtain 2.7 g of a compound represented by Formula (I-14).

$^1$H NMR (CDCl$_3$) δ 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.56 (t, 2H), 3.60-3.66 (m, 4H), 3.73 (t, 2H), 3.74 (d, 2H), 3.85 (d, 2H), 3.90 (t, 2H), 3.94 (td, 4H), 4.00 (t, 2H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

LCMS: 1190 [M+1]

(Example 17) Production of Compound Represented by Formula (I-15)

[Chem. 59]
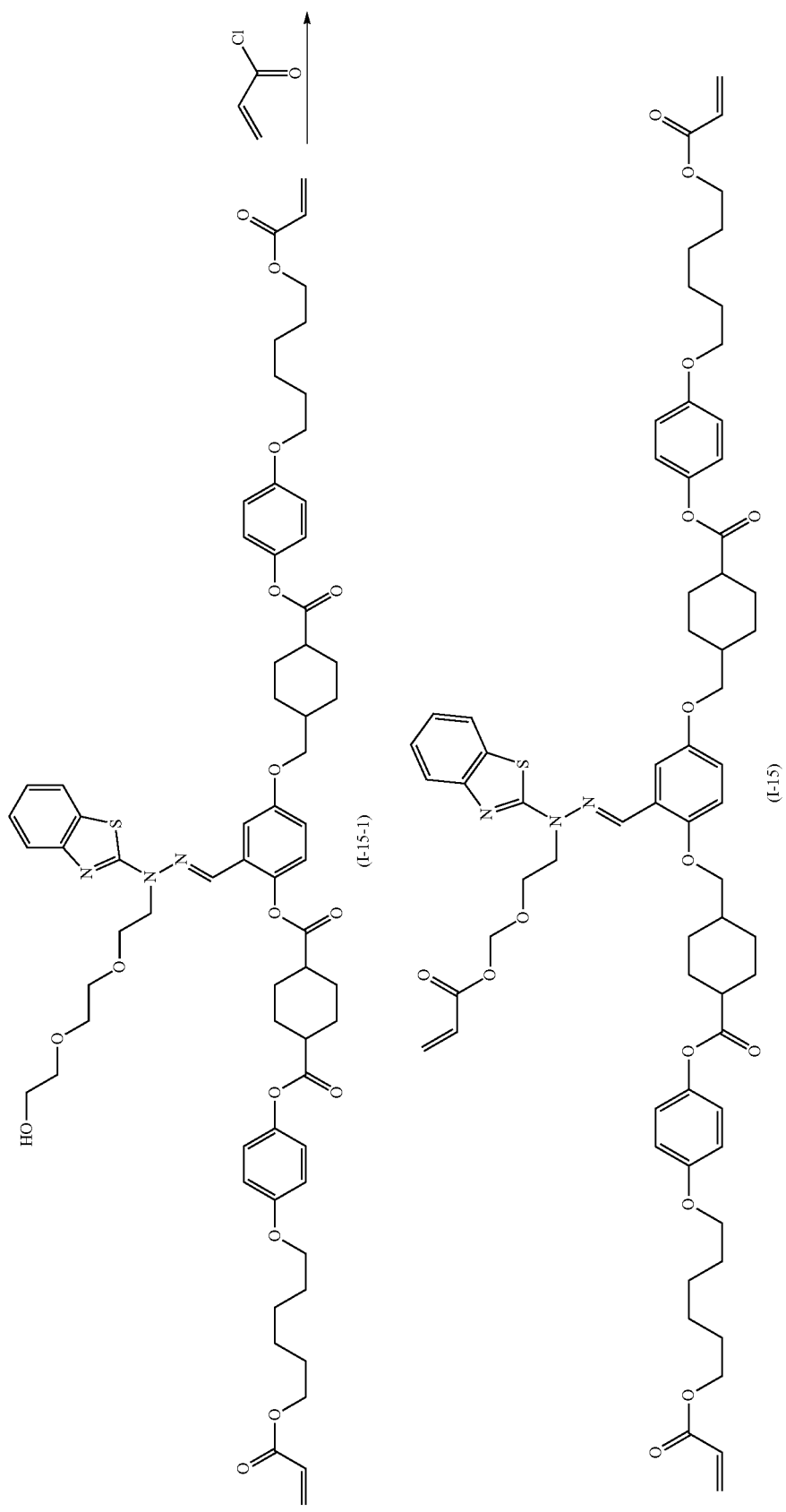

Under a nitrogen atmosphere, 3.0 g of the compound represented by Formula (I-15-1), 0.5 g of diisopropylethylamine, and 30 mL of dichloromethane were added to a reaction container. 0.3 g of acryloyl chloride was added dropwise thereto while cooling with ice, and the mixture was stirred at room temperature for 5 hours. After washing with 1% hydrochloric acid and a saline solution, purification was performed by column chromatography (silica gel) and recrystallization (dichloromethane/methanol) to obtain 2.6 g of a compound represented by Formula (I-15).

Transition temperature (heating rate 5° C./min) C, 71 N, 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

(Example 18) Production of Compound Represented by Formula (I-16)

[Chem. 60]

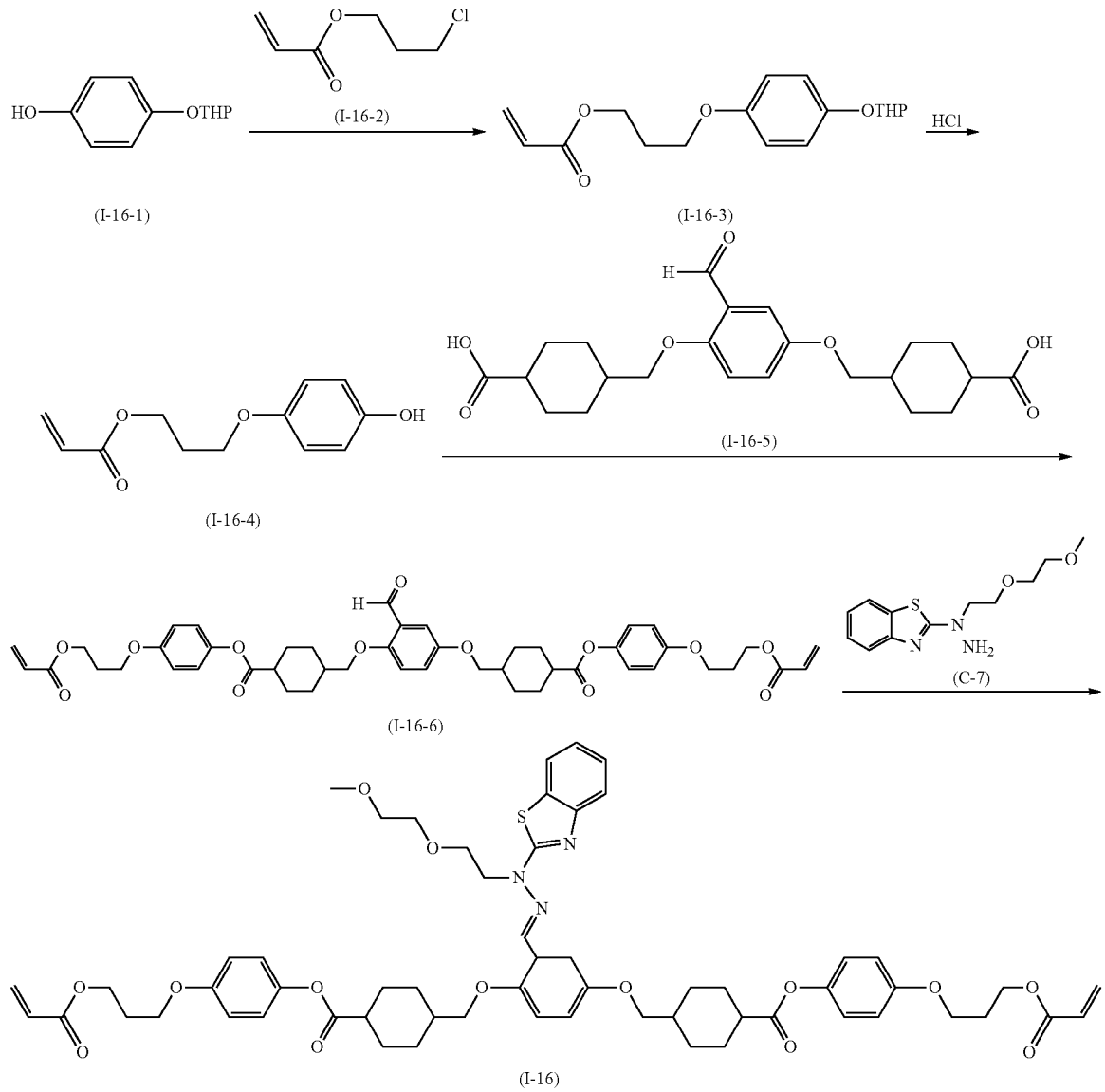

Using the same method as in Example 13 except that the compound represented by Formula (I-11-13) was substituted with the compound represented by Formula (I-16-2), the compound represented by Formula (I-16) was produced using the compound represented by Formula (C-7) produced by the method described in Example 7.

Transition temperature (temperature rise 5° C./min): C, 89-95 N, 145 I $^1$H NMR (CDCl$_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36

(t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm.

(Example 19) Production of Compound Represented by Formula (I-17)

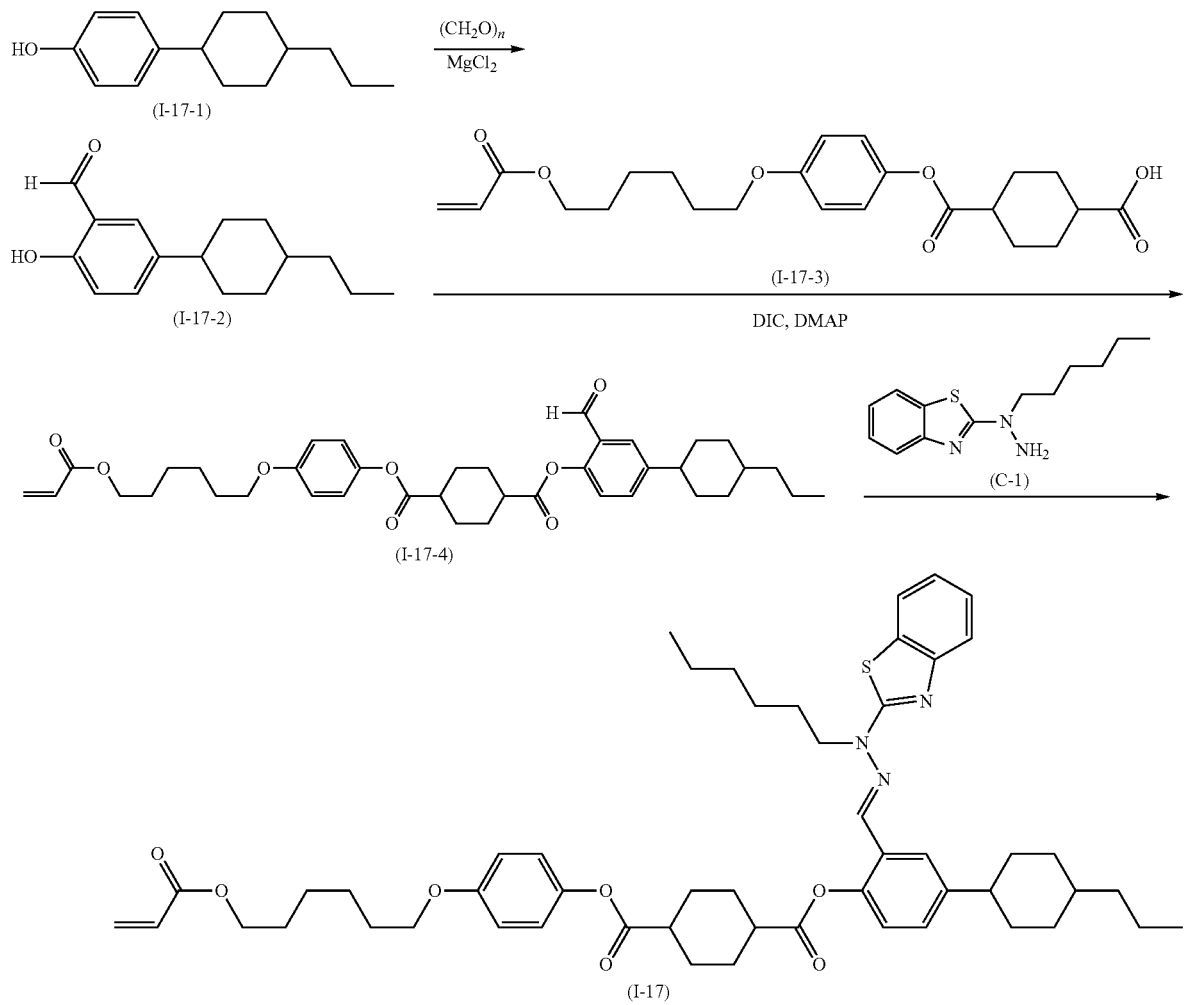

5.00 g of the compound represented by Formula (I-17-1), 3.27 g of magnesium chloride, 2.06 g of paraformaldehyde, 20 mL of triethylamine, and 80 mL of acetonitrile were added to a reaction container. Paraformaldehyde was appropriately added while stirring at 60° C. The resultant was diluted with ethyl acetate and washed with hydrochloric acid and a saline solution. Purification was performed by column chromatography (silica gel, hexane/ethyl acetate) to obtain 5.36 g of a compound represented by Formula (I-17-2).

Under a nitrogen atmosphere, 2.0 g of the compound represented by Formula (I-17-2), 3.4 g of the compound represented by Formula (I-17-3), 0.4 g of N,N-dimethylaminopyridine, and 30 mL of dichloromethane were added to a reaction container. 1.3 g of diisopropylcarbodiimide was added dropwise thereto while cooling with ice and the mixture was stirred at room temperature. After the precipitate was filtered, the filtrate was washed with a 5% hydrochloric acid, water and a saline solution. Purification was performed by column chromatography (silica gel, dichloromethane) and recrystallization (dichloromethane/methanol) to obtain 3.7 g of a compound represented by Formula (I-17-4).

1.0 g of the compound represented by Formula (C-1) produced by the method described in Example 1, 2.6 g of the compound represented by Formula (I-17-4), 0.6 g of (±)-10-camphorsulfonic acid, 20 mL of tetrahydrofuran, and 10 mL of ethanol were added to a reaction container. After heating and stirring at 50° C., the solvent was distilled off and dispersed and washed with methanol. Purification was performed by column chromatography (silica gel) and recrystallization (dichloromethane/methanol) to obtain 2.5 g of a compound represented by Formula (I-17).

Transition temperature (temperature rise 5° C./min): C, 117-122 N, 146 I $^1$H NMR (CDCl$_3$) δ 0.91 (m, 6H), 1.10 (q, 2H), 1.23-1.56 (m, 18H), 1.68-1.81 (m, 9H), 1.94 (t, 4H), 2.32 (m, 4H), 2.56-2.70 (m, 3H), 3.94 (t, 2H), 4.18 (t, 2H), 4.29 (t, 2H), 5.82 (d, 1H), 6.13 (dd, 1H), 6.40 (dd, 1H), 6.89 (d, 2H), 6.99 (m, 3H), 7.16 (t, 1H), 7.23 (dd, 1H), 7.34 (t, 1H), 7.66-7.72 (m, 3H), 7.90 (d, 1H) ppm.

MS (m/z): 878 [M++1]

(Example 20) Production of Compound Represented by Formula (I-18)

[Chem. 62]

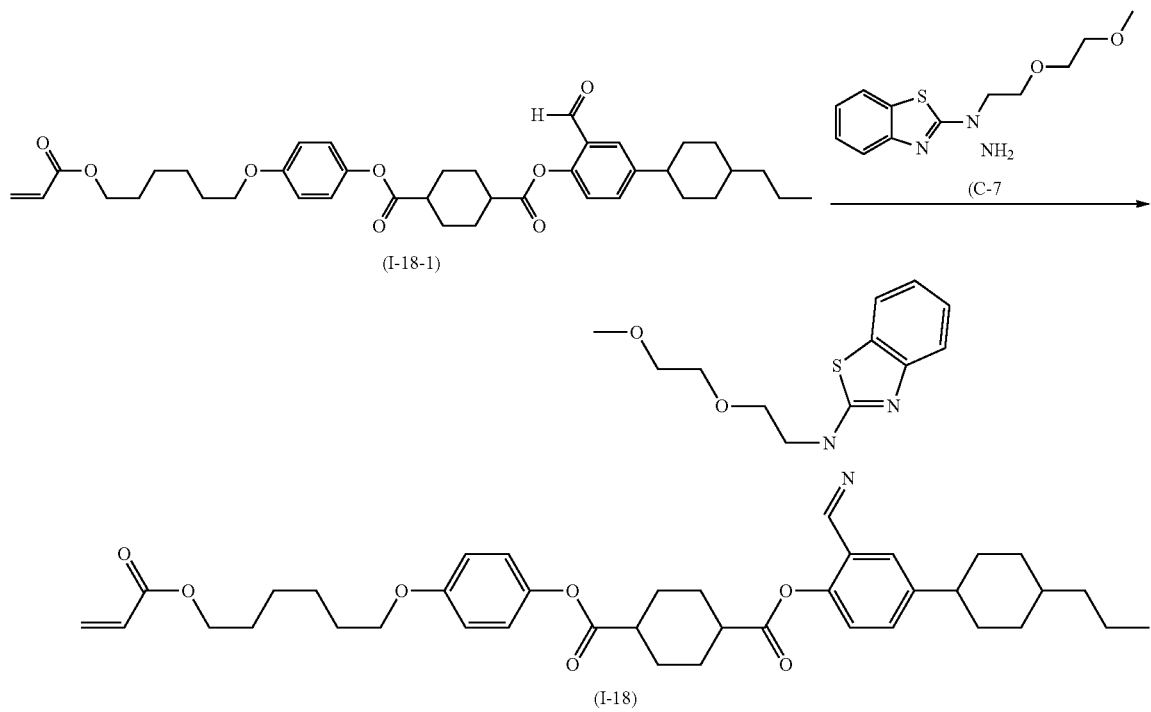

2.5 g of the compound represented by Formula (I-18-1), 1.0 g of the compound represented by Formula (C-7) produced by the method described in Example 7, 0.5 g of (±)-10-camphorsulfonic acid, 10 mL of tetrahydrofuran, and 10 mL of ethanol were added to a reaction container. After heating and stirring at 50° C., the solvent was distilled off, and the resultant was dispersed and washed with methanol. Purification was performed by column chromatography (silica gel) and recrystallization to obtain 2.0 g of a compound represented by Formula (I-18).

Transition temperature (temperature rise 5° C./min): C, 106 N, 125 I $^1$H NMR (CDCl$_3$) δ 0.92 (t, 3H), 1.05-1.83 (m, 22H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

(Example 21) Production of Compound Represented by Formula (I-19)

[Chem. 63]

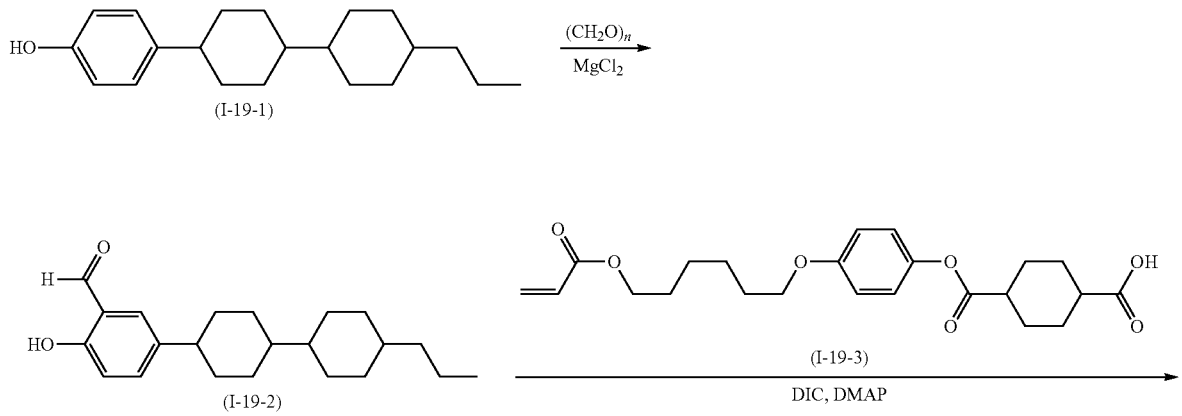

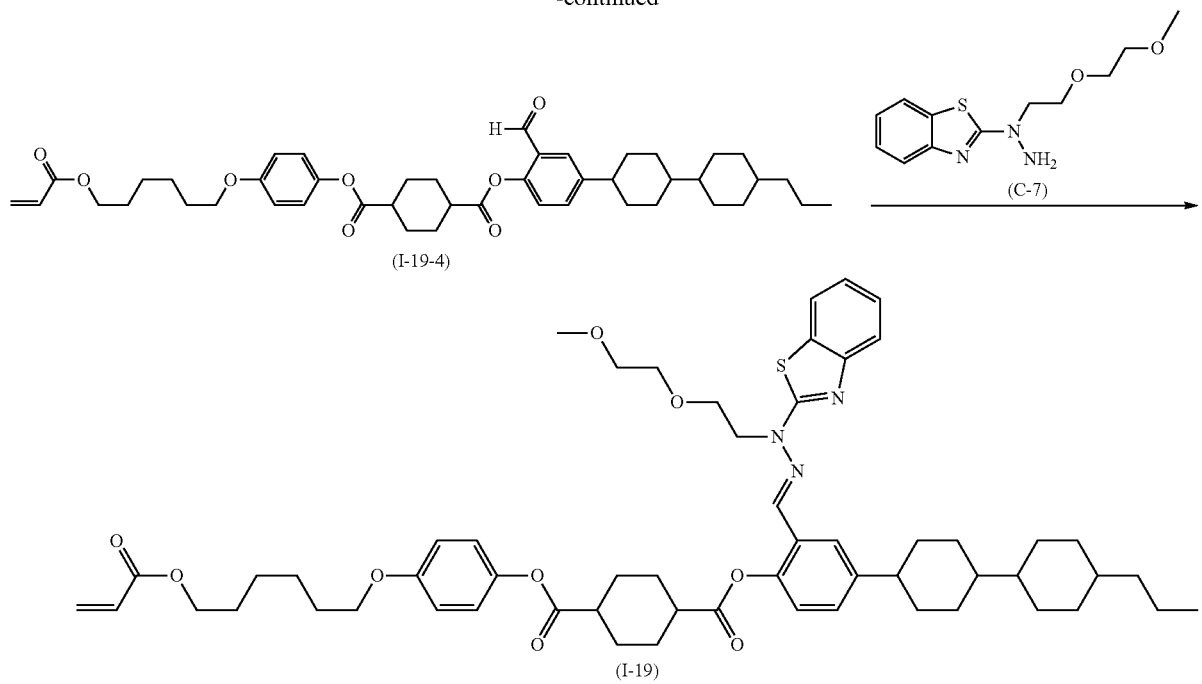

The compound represented by Formula (I-19) was produced using the same method in Example 19 except that the compound represented by Formula (I-17-1) was replaced with the compound represented by Formula (I-19-1), and the compound represented by Formula (C-1) was replaced with the compound represented by Formula (C-7) produced by the method described in Example 7.

$^1$H NMR (CDCl$_3$) δ 0.92 (t, 3H), 1.05-1.83 (m, 32H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

MS (m/z): 978 [M$^+$+1]

(Example 22) Production of Compound Represented by Formula (I-20)

[Chem. 64]

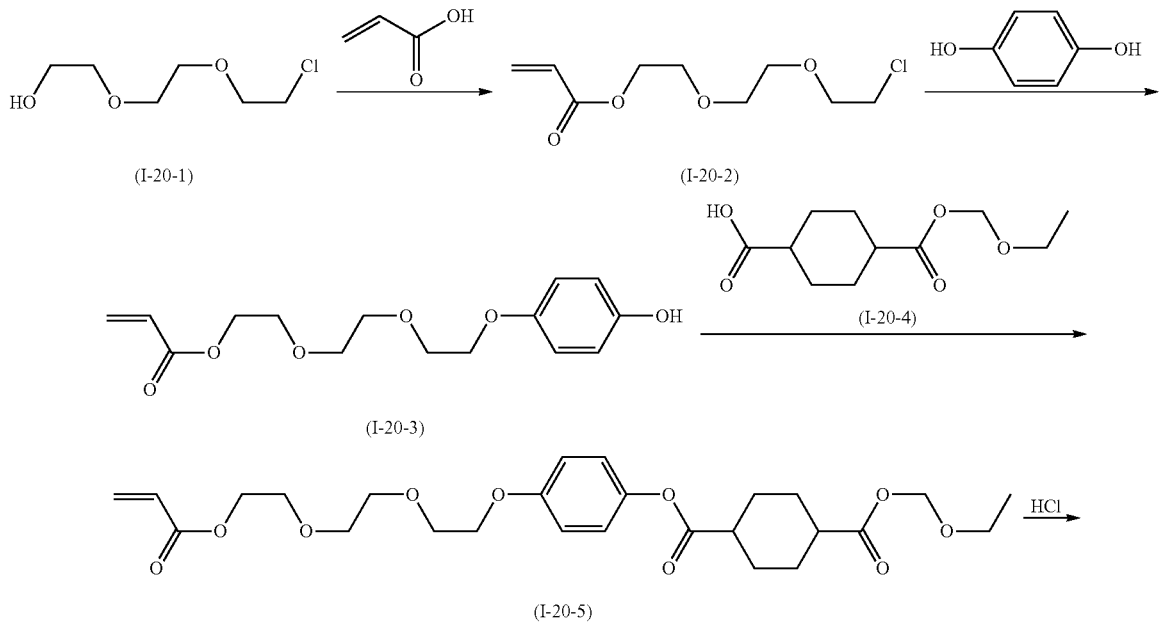

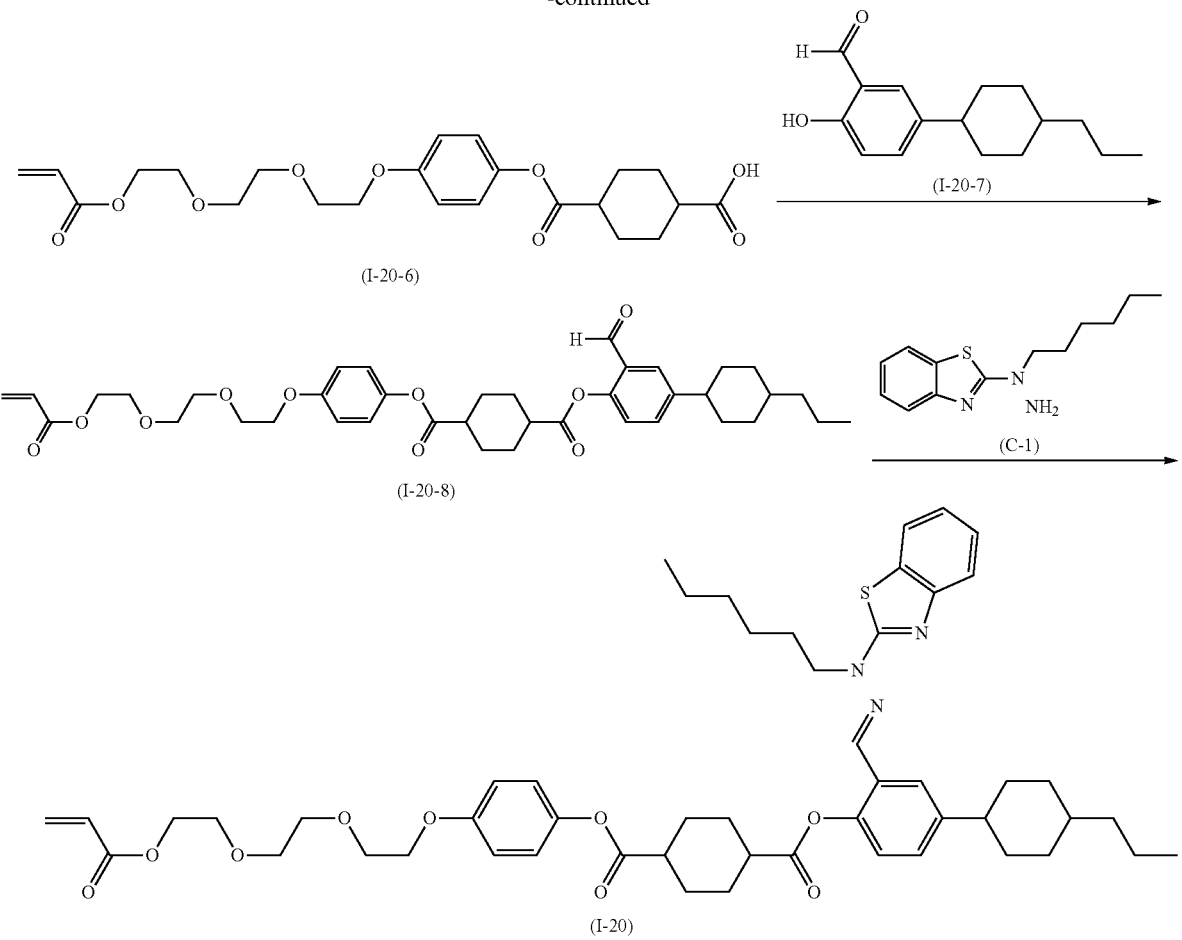

The compound represented by Formula (I-20-6) was produced by the same method as in Example 14 except that the compound represented by Formula (I-12-1) was replaced with the compound represented by Formula (I-20-1).

A compound represented by Formula (I-20) was produced using the compound represented by Formula (C-1) produced by the method described in Example 1 using the same method as in Example 19 except that the compound represented by Formula (I-17-4) was replaced with the compound represented by Formula (I-20-8).

Transition temperature (temperature rise 5° C./min): C, 131 I $^1$H NMR (CDCl$_3$) δ0.88-0.94 (m, 6H), 1.10 (m, 2H), 1.22-1.52 (m, 13H), 1.72 (m, 6H), 1.94 (t, 4H), 2.32 (m, 4H), 2.53-2.62 (m, 3H), 3.69-3.77 (m, 6H), 3.86 (t, 2H), 4.12 (t, 2H), 4.27-4.34 (m, 4H), 5.83 (dd, 1H), 6.16 (dd, 1H), 6.43 (dd, 1H), 6.91 (d, 2H), 6.97-7.02 (m, 3H), 7.16 (t, 1H), 7.23 (dd, 1H), 7.33 (t, 1H), 6.66-7.72 (m, 3H), 7.90 (d, 1H) ppm.
LCMS: 910 [M+1]

(Example 23) Production of Compound Represented by Formula (I-21)

[Chem. 65]

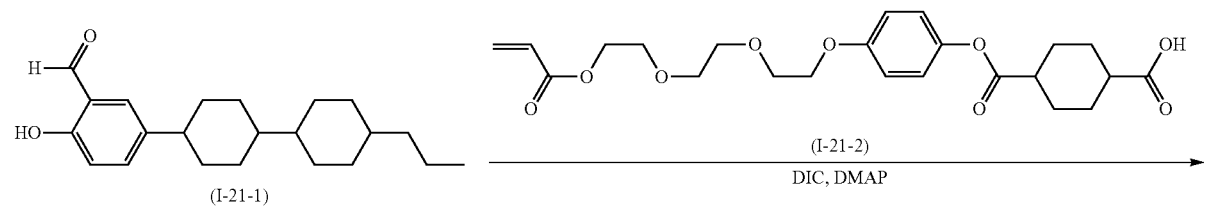

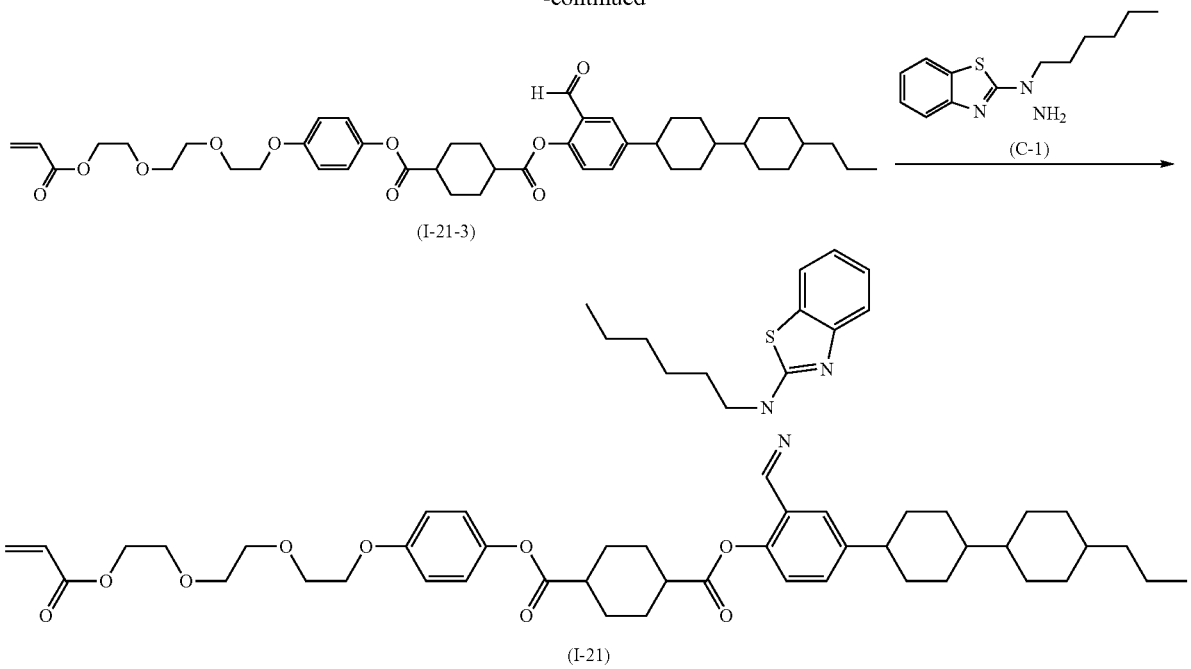

The compound represented by Formula (I-21) was produced using the compound represented by Formula (C-1) produced by the method described in Example 1 using the same method as in Example 22 except that the compound represented by Formula (I-20-7) was replaced with the compound represented by Formula (I-21-1).

Transition temperature (temperature rise 5° C./min): C, 90 S 218 N, 265 I $^1$H NMR (CDCl$_3$) δ 0.88 (m, 6H), 1.01-1.19 (m, 8H), 1.32-1.45 (m, 6H), 1.71-1.76 (m, 6H), 1.88-1.99 (m, 3H), 2.17 (m, 12H), 2.31 (m, 4H), 2.53 (m, 2H), 2.67 (m, 1H), 3.70-3.76 (m, 6H), 3.85 (t, 2H), 4.11 (t, 2H), 4.31 (m, 4H), 5.82 (d, 2H), 6.15 (q, 2H), 6.43 (d, 2H), 6.92 (m, 5H), 7.14-7.26 (m, 2H), 7.33 (t,

[Chem. 66]

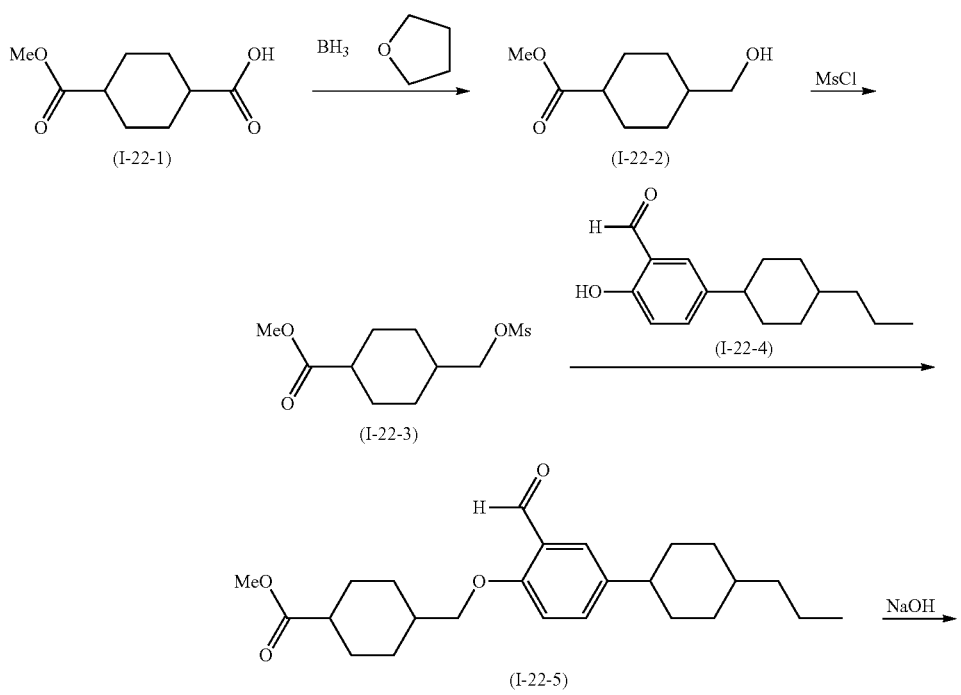

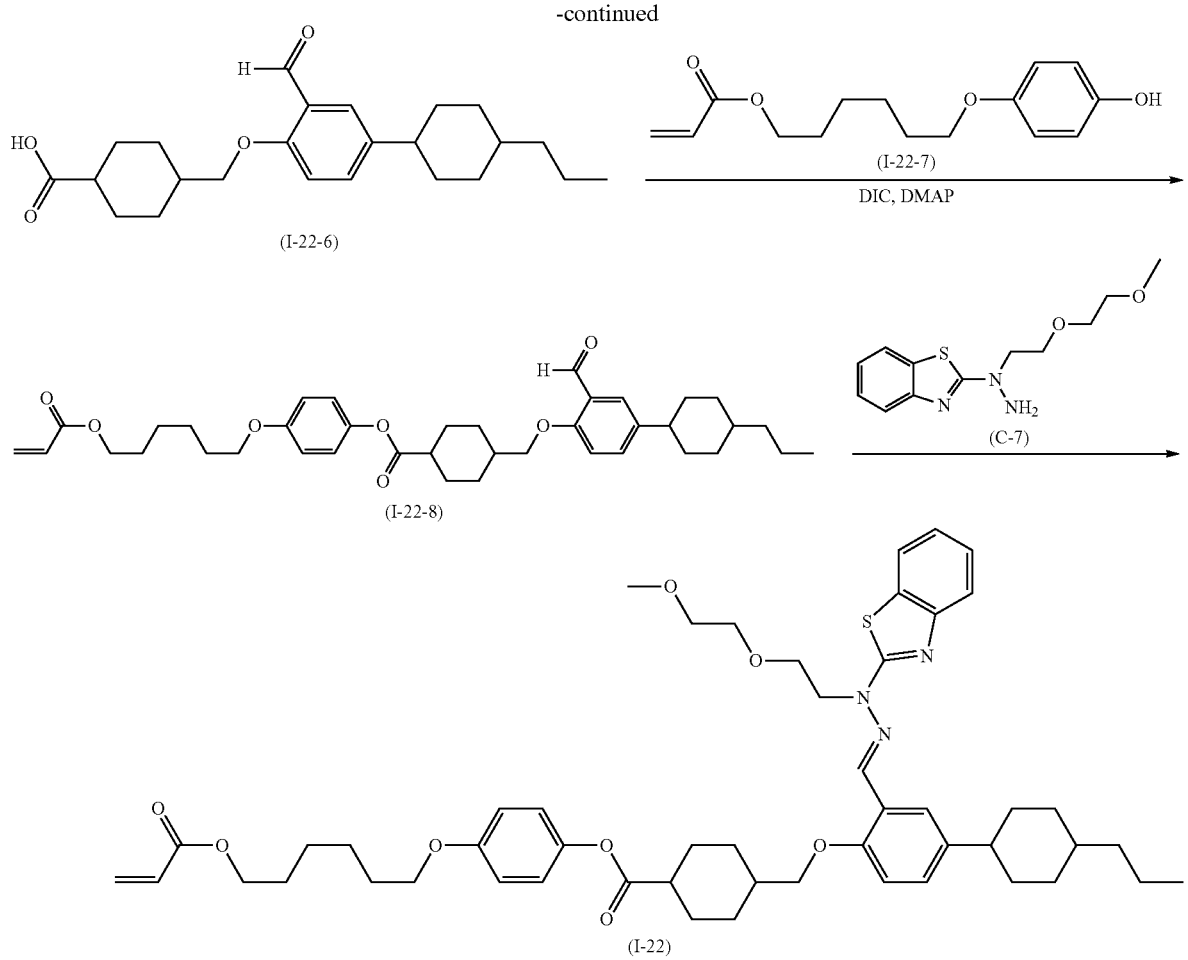

Under a nitrogen atmosphere, 20.0 g of the compound represented by Formula (I-22-1) and 120 mL of tetrahydrofuran were added to a reaction container. 143 mL of borane-tetrahydrofuran complex (0.9 mol/L) was added dropwise thereto while cooling with ice and the mixture was stirred for 2 hours. After being poured into 200 mL of 5% hydrochloric acid, the resultant was subjected to a liquid separation treatment with 200 mL of ethyl acetate. After drying over sodium sulfate, the solvent was distilled off to obtain 17.6 g of a compound represented by Formula (I-22-2).

Under a nitrogen atmosphere, 17.6 g of a compound represented by Formula (I-22-2), 12.1 g of pyridine, and 100 mL of dichloromethane were added to a reaction container. 12.9 g of methanesulfonyl chloride was added dropwise thereto while cooling with ice, and the mixture was stirred at room temperature for 8 hours. After being poured into 5% hydrochloric acid, the resultant was subjected to a liquid separation treatment. Purification was performed by column chromatography (silica gel) to obtain 23.0 g of a compound represented by Formula (I-22-3).

4.0 g of the compound represented by Formula (I-22-3), 3.9 g of the compound represented by Formula (I-22-4), 3.5 g of potassium carbonate, and 30 mL of N, N-dimethylformamide were added to a reaction container, and the mixture was heated and stirred at 90° C. for 12 hours. The resultant was diluted with dichloromethane and washed with water and a saline solution. Purification was performed by column chromatography (silica gel) and recrystallization to obtain 5.1 g of a compound represented by Formula (I-22-5).

5.1 g of the compound represented by Formula (I-22-5), 30 mL of tetrahydrofuran, 30 mL of methanol, and 10 mL of 25% sodium hydroxide aqueous solution were added to the reaction container, and the mixture was stirred at 60° C. Hydrochloric acid was added thereto and the solvent was distilled off. The resultant was washed with water and dried to obtain 4.9 g of a compound represented by Formula (I-22-6).

Under a nitrogen atmosphere, 4.9 g of the compound represented by Formula (I-22-6), 3.4 g of the compound represented by Formula (I-22-7), 0.1 g of N,N-dimethylaminopyridine, and 40 mL of dichloromethane were added to a reaction container. 1.6 g of diisopropylcarbodiimide was added dropwise thereto while cooling with ice and stirred. Purification was performed by column chromatography (silica gel) and recrystallization to obtain 5.7 g of a compound represented by Formula (I-22-8).

2.5 g of the compound represented by Formula (I-22-8), 1.1 g of the compound represented by Formula (C-7) produced by the method described in Example 7, 0.5 g of (±)-10-camphorsulfonic acid, 10 mL of tetrahydrofuran, and 10 mL of ethanol were added to the reaction container. After heating and stirring at 50° C., the solvent was distilled off and dispersed and washed with methanol. Purification was performed by column chromatography (silica gel) and recrystallization to obtain 2.1 g of a compound represented by Formula (I-22).

Transition temperature (temperature rise 5° C./min, temperature drop 5° C./min): C, 101-105 (N, 82) I
$^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.
(Example 25) Preparation of a Compound Represented by Formula (I-23)
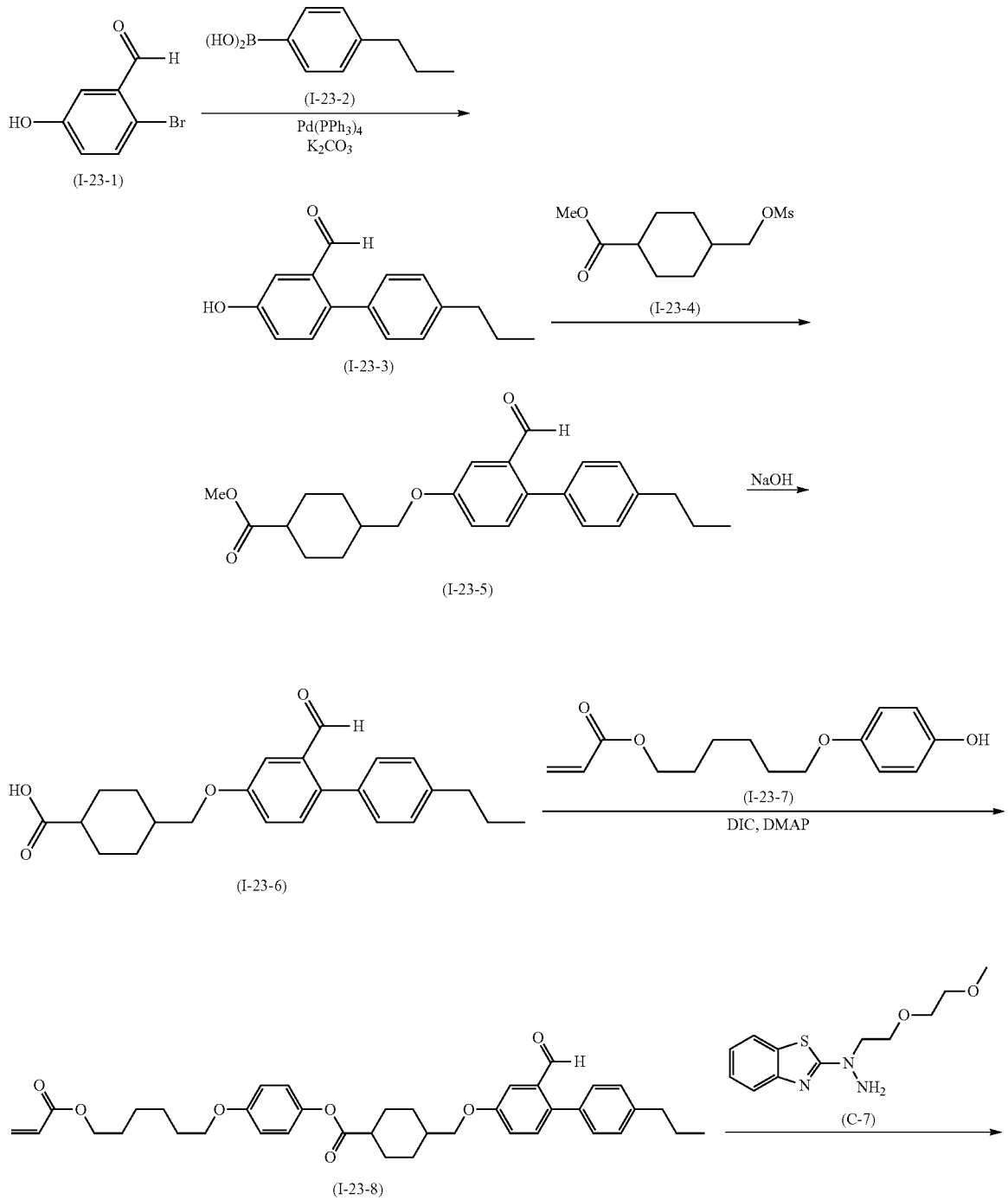

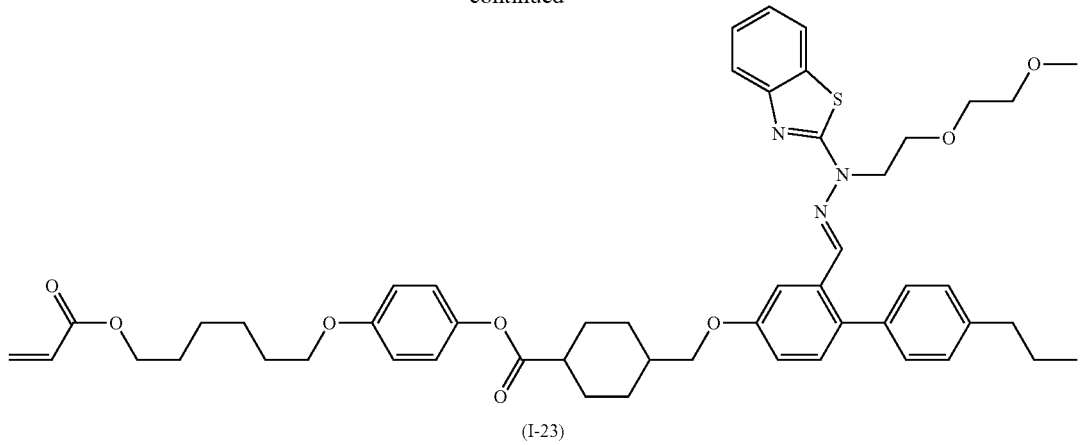

(I-23)

5.0 g of the compound represented by Formula (I-23-1), 4.1 g of the compound represented by Formula (I-23-2), 5.2 g of potassium carbonate, and 50 mL of ethanol were added to the reaction container. After substituting nitrogen in the reaction container, 0.3 g of tetrakis (triphenylphosphine) palladium (0) was added thereto and the mixture was heated under reflux. After diluting with ethyl acetate and washing with a 5% hydrochloric acid and a saline solution, purification was performed by column chromatography (silica gel, ethyl acetate) to obtain 4.8 g of a compound represented by Formula (I-23-3).

4.0 g of the compound represented by Formula (I-23-3), 4.2 g of the compound represented by Formula (I-23-4), 3.5 g of potassium carbonate, and 30 mL of N, N-dimethylformamide were added to a reaction container and the mixture was heated and stirred at 90° C. for 12 hours. The resultant was diluted with dichloromethane and washed with water and a saline solution. Purification was performed by column chromatography (silica gel, dichloromethane) and recrystallization (dichloromethane/methanol) to obtain 4.6 g of a compound represented by Formula (I-23-5).

4.6 g of the compound represented by Formula (I-23-5), 30 mL of tetrahydrofuran, 30 mL of methanol, and 10 mL of a 25% sodium hydroxide aqueous solution were added to the reaction container, and the mixture was stirred at 60° C. Hydrochloric acid was added thereto and the solvent was distilled off. The resultant was washed with water and dried to obtain 4.4 g of a compound represented by Formula (I-23-6).

Under a nitrogen atmosphere, 4.4 g of the compound represented by Formula (I-23-6), 3.1 g of the compound represented by Formula (I-23-7), 0.1 g of N,N-dimethylaminopyridine, and 40 mL of dichloromethane were added to a reaction container. 1.8 g of diisopropylcarbodiimide was added dropwise thereto while cooling with ice and stirred. Purification was performed by column chromatography (silica gel, dichloromethane) and recrystallization (dichloromethane/methanol) to obtain 5.1 g of a compound represented by Formula (I-23-8).

2.5 g of the compound represented by Formula (I-23-8), 1.1 g of the compound represented by Formula (C-7) produced by the method described in Example 7, 0.5 g of (±)-10-camphorsulfonic acid, 10 mL of tetrahydrofuran, and 10 mL of ethanol were added to the reaction container. After heating and stirring at 50° C., the solvent was distilled off and dispersed and washed with methanol. Purification was performed by column chromatography (silica gel, dichloromethane) and recrystallization (dichloromethane/methanol) to obtain 1.8 g of a compound represented by Formula (I-23).

Transition temperature (temperature rise 5° C./min): C, 67-100 I $^1$H NMR (CDCl$_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, LH), 7.91 (s, 1H) ppm.

(Examples 26 to 48 and Comparative Examples 9 to 17) Film Production

In order to produce a film, a liquid crystal composition formed of 50% of compound (X-1) described in WO2012/002140A1, 10% of compound (X-2) described in JP 2002-542219 A, and 40% of compound (X-3) described in JP 2005-015473 A was used as a host liquid crystal (X).

[Chem. 68]

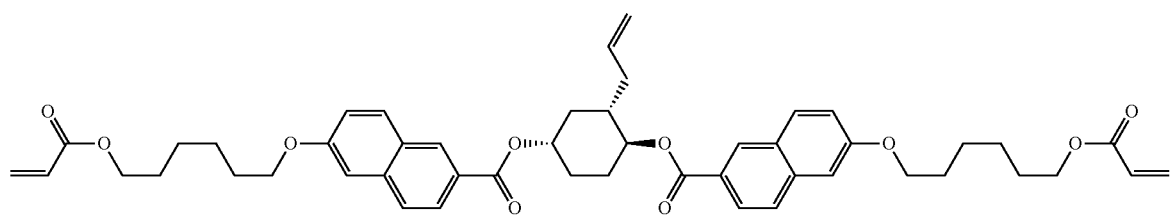

(X-1)

-continued

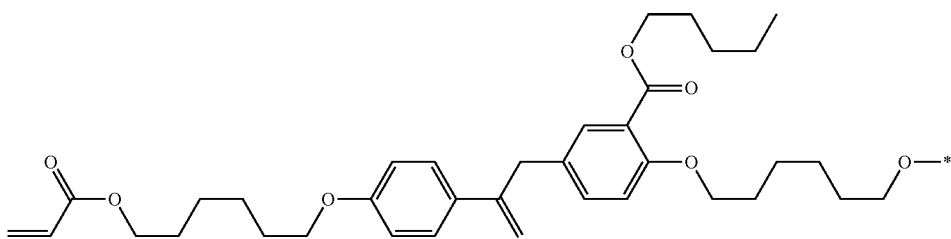
(X-2)

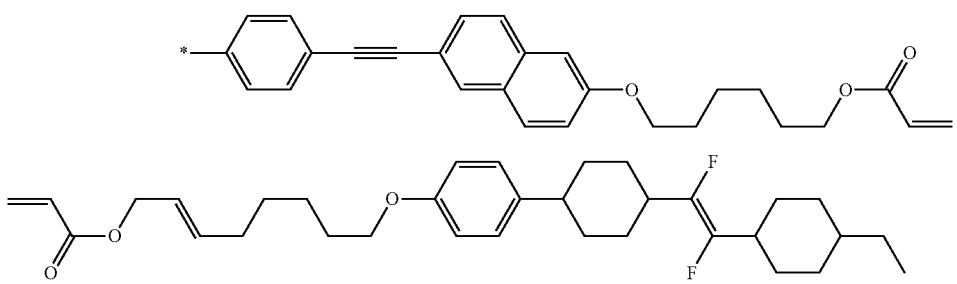
(X-3)

The polyimide solution for an alignment film was coated on a glass substrate having a thickness of 0.7 mm by a spin coating method, dried at 100° C. for 10 minutes, and then baked at 200° C. for 60 minutes to obtain a coating film. The obtained coating film was subjected to a rubbing treatment. The rubbing treatment was performed using a commercially available rubbing apparatus.

1% of the photopolymerization initiator Irgacure 907 (produced by BASF), 0.1% of 4-methoxyphenol, and 80% of chloroform were added to each of the compositions prepared by adding 30% of the compound to be evaluated to the host liquid crystal (X), thereby preparing a coating solution. The thus-prepared coating solution was coated on a rubbed glass substrate by a spin coating method. The resultant was dried at 80° C. for 1 minute and further at 120° C. for 1 minute. Thereafter, using a high-pressure mercury lamp, the resultant was irradiated with ultraviolet rays for 25 seconds at an intensity of 40 mW/cm² to produce a film to be evaluated.

Each prepared film was irradiated with light of 100 J at 50 mW/cm² at 25° C. using a xenon lamp irradiation tester (Suntest XLS produced by Atlas). Discoloration and change in aligning property were evaluated for each obtained film, respectively. The evaluation results are shown in the table below.

<Discoloration>

The yellowness indices (YI) of the film before light irradiation and after light irradiation were each measured to determine the yellowing index (ΔYI). For the yellowness index, the absorption spectrum of the polymer was measured by a JASCO UV/VIS Spectrophotometer V-560, and the yellowness index (YI) was calculated by the attached color diagnostic program. The calculation formula is:

$$YI=100(1.28X-1.06Z)/Y$$

(where YI represents the yellowness index, and X, Y, and Z represent tristimulus values in the XYZ colorimetric system (JIS K 7373)).

Incidentally, the yellowing index (ΔYI) means the difference between the yellowness index before light irradiation and the yellowness index after light irradiation.

<Change in Aligning Property>

The aligning property was evaluated by polarizing microscope observation as follows.

A: defects are not observed at all.
B: defects are very slight.
C: a few defects are seen.
D: quite a few defects are seen.
E: many defects are seen.

TABLE 1

| Film | Evaluation Compound used | ΔYI | Aligning Property |
| --- | --- | --- | --- |
| Example 26 | Compound (I-1) of the Present Invention | 0.8 | C |
| Example 27 | Compound (I-2) of the Present Invention | 0.8 | C |
| Example 28 | Compound (I-3) of the Present Invention | 0.9 | C |
| Example 29 | Compound (I-4) of the Present Invention | 0.8 | C |
| Example 30 | Compound (I-5) of the Present Invention | 0.8 | C |
| Example 31 | Compound (I-6) of the Present Invention | 0.3 | A |
| Example 32 | Compound (I-7) of the Present Invention | 0.4 | B |
| Example 33 | Compound (I-8) of the Present Invention | 0.5 | B |
| Example 34 | Compound (I-9) of the Present Invention | 0.4 | B |
| Example 35 | Compound (I-10) of the Present Invention | 0.6 | C |
| Example 36 | Compound (I-11) of the Present Invention | 0.2 | A |
| Example 37 | Compound (I-12) of the Present Invention | 0.4 | B |
| Example 38 | Compound (I-13) of the Present Invention | 0.5 | B |
| Example 39 | Compound (I-14) of the Present Invention | 0.2 | A |

TABLE 1-continued

| Film | Evaluation Compound used | ΔYI | Aligning Property |
|---|---|---|---|
| Example 40 | Compound (I-15) of the Present Invention | 0.3 | A |

TABLE 2

| Film | Evaluation Compound used | ΔYI | Aligning Property |
|---|---|---|---|
| Example 41 | Compound (I-16) of the Present Invention | 0.2 | A |
| Example 42 | Compound (I-17) of the Present Invention | 0.5 | B |
| Example 43 | Compound (I-18) of the Present Invention | 0.3 | A |
| Example 44 | Compound (I-19) of the Present Invention | 0.3 | A |
| Example 45 | Compound (I-20) of the Present Invention | 0.8 | C |
| Example 46 | Compound (I-21) of the Present Invention | 0.7 | C |
| Example 47 | Compound (I-22) of the Present Invention | 0.5 | B |
| Example 48 | Compound (I-23) of the Present Invention | 0.5 | B |

TABLE 3

| Film | Evaluation Compound used | ΔYI | Aligning Property |
|---|---|---|---|
| Comparative Example 9 | Comparative compound (I-1R) | 1.3 | E |
| Comparative Example 10 | Comparative compound (I-2R) | 1.4 | E |
| Comparative Example 11 | Comparative compound (I-3R) | 1.3 | E |
| Comparative Example 12 | Comparative compound (I-4R) | 1.3 | E |
| Comparative Example 13 | Comparative compound (I-5R) | 1.4 | E |
| Comparative Example 14 | Comparative compound (I-6R) | 0.8 | C |
| Comparative Example 15 | Comparative compound (I-7R) | 1.0 | D |
| Comparative Example 16 | Comparative compound (I-8R) | 1.1 | D |
| Comparative Example 17 | Comparative compound (I-10R) | 1.0 | E |

From the table, in comparison with the films containing the compounds produced by the production method of Comparative Example, it is understood that discoloration and change in aligning property did not easily occur in the films containing the compounds produced by the production method of the present invention of Example 26 to Example 48 even after irradiation with ultraviolet light for a long time. In the case where 2-hydrazinobenzothiazole having a substituent such as an alkyl group on the nitrogen atom, which is an intermediate, is produced by the production method of the Comparative Examples, the color of the reaction solution during the reaction was discolored from brown to deep blue in the step of N-alkylation reaction, and accordingly, by-products having a largely conjugated system appear to be generated. It appears that such by-products are left unremoved in a trace amount in subsequent steps or lead to impurities having a higher molecular weight, and are mixed in the target polymerizable compound, whereby discoloration and aligning property are impaired. On the other hand, in the production method of the present invention, since the color of the reaction solution during the reaction was colorless to pale yellow, the formation of by-products as described above was suppressed, and it is considered that the adverse effect was small in the case of producing the polymerizable compound using the obtained intermediate and then preparing a film.

From the above results, the compound produced by the production method of the present invention is useful as a constituent member of the polymerizable composition. In addition, an optically anisotropic body using a composition containing the compound of the present invention is useful for applications such as optical films.

The invention claimed is:

1. A method for producing a polymerizable compound comprising:

a step of reacting a compound represented by General Formula (I-B-a):

$$W^2-NH-NH_2 \quad \text{(I-B-a)}$$

wherein $W^2$ represents a linear or branched alkyl group having 2 to 20 carbon atoms in which one —$CH_2$— or two or more non-adjacent —$CH_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, with a compound represented by General Formula (I-B-b):

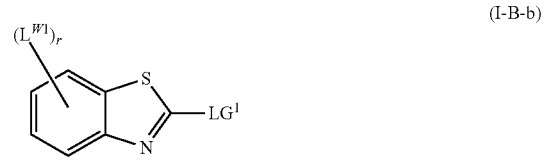

(I-B-b)

wherein r represents an integer of 0 to 4, $L^{W1}$ represents a fluorine atom, a chlorine atom, a bromine atom, an iodine atom, a pentafluorosulfuranyl group, a nitro group, a cyano group, a dimethylamino group, a diethylamino group, a diisopropylamino group, or a linear or branched alkyl group having 1 to 20 carbon atoms in which one —$CH_2$— or two or more non-adjacent —$CH_2$—'s may each independently be substituted with —O—, —S—, —CH=CH—, —CF=CF—, or —C≡C—, and arbitrary hydrogen atoms in the alkyl group may be substituted with a fluorine atom, plural $L^{W1}$'s, if any, may be the same or different, and $LG^1$ represents a fluorine atom, a chlorine atom, a bromine atom, an iodine atom, a methoxy group, a methylsulfanyl group, a hydroxyl group, a mercapto group, an amino group, a methylamino group, a dimethylamino group, a hydrazinyl group, or a benzothiazol-2-yl disulfanyl group to thereby obtain a compound represented by General Formula (I-C):

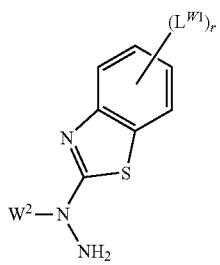
(I-C)

wherein $W^2$, r, and $L^{W1}$ represent the same meanings as defined above, the compound represented by General Formula (I-B-a) is produced by a reaction between a compound represented by General Formula (I-A) and hydrazine:

$$W^2\text{-}LG^2 \quad \text{(I-A)}$$

$W^2$ represents the same meaning as defined in General Formula (I-B-a), and $LG^2$ represents a chlorine atom, a bromine atom, an iodine atom, a methanesulfonyl group, or a p-toluenesulfonyl group the reaction is carried out in the presence of an alkali or a base, the polymerizable compound is represented by General Formula (I):

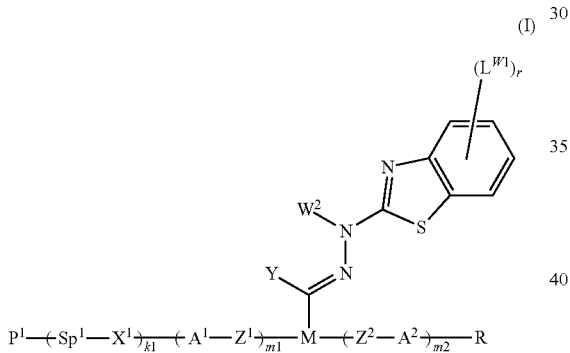
(I)

wherein $W^2$, r, and $L^{W1}$ represent the same meanings as defined in General Formula (I-B-a) or General Formula (I-B-b);

$P^1$ represents a polymerizable group, and the polymerizable group is a group polymerizable by radical polymerization, radical addition polymerization, cationic polymerization, or anionic polymerization;

$Sp^1$ represents a spacer group, and plural $Sp^1$'s, if any, may be the same or different;

$X^1$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—, a single bond, and plural $X^1$'s, if any, may be the same or different;

$k^1$ represents an integer of 0 to 10;

R represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which arbitrary hydrogen atoms in the group may be substituted with a fluorine atom, and one —CH$_2$— or two or more non-adjacent —CH$_2$—'s may each independently be substituted with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—, or R represents a group represented by —(X$^2$—Sp$^2$)$_{k2}$-P$^2$, where P$^2$ represents a polymerizable group, and the polymerizable group is a group polymerizable by radical polymerization, radical addition polymerization, cationic polymerization, or anionic polymerization, Sp$^2$ represents a spacer group, plural Sp$^2$'s, if any, Sp$^2$'s may be the same or different, $X^2$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, plural $X^2$'s, if any, may be the same or different, and k2 represents an integer of 0 to 10;

$A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted with one or more substituents L, plural $A^1$'s, if any, may be the same or different, and plural $A^2$'s, if any, may be the same or different, L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— or two or more non-adjacent —CH$_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, or L may represent a group represented by $P^L$—$(Sp^L$-$X^L)_{kL}$— where, $P^L$ represents a polymerizable group, and the polymerizable group is a group polymerizable by radical polymerization, radical addition polymerization, cationic polymerization, or anionic polymerization, $Sp^L$ represents a spacer group or a single bond, plural $Sp^L$'s, if any, may be the same or different, $X^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, plural $X^L$'s, if any, may be the same or different, kL represents an integer of 0 to 10, and plural kL's, if present in the compound, may be the same or different;

$Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, plural $Z^1$'s, if any, may be the same or different, and plural $Z^2$'s, if any, may be the same or different;

m1 and m2 each independently represent an integer of 0 to 6, provided that m1+m2 represents an integer of 0 to 6;

M represents a trivalent aromatic group which may be substituted; and

Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— or two or more non-adjacent —CH$_2$—'s may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, provided that the compound represented by General Formula (I) does not include an —O—O— bond.

2. The method for producing a polymerizable compound according to claim 1, wherein, in General Formula (I-B-a), $W^2$ represents a linear or branched alkyl group having 2 to 20 carbon atoms in which one —CH$_2$— or two or more non-adjacent —CH$_2$—'s may each independently be substituted with —O—, —S—, —CH=CH—, —CF=CF—, or —C≡C—, provided that arbitrary hydrogen atoms in the alkyl group and the hydroxyalkyl group may be substituted with a fluorine atom.

3. The method for producing a polymerizable compound according to claim 1,
wherein, in General Formula (I), $O^1$, and if present, $P^2$ represent a group selected from Formula (P-1) to Formula (P-20):

(P-1)

(P-2)

(P-3)

(P-4)
(P-5)
(P-6)
(P-7)
(P-8)

(P-9)

(P-10)

(P-11)

(P-12)

(P-13)

-continued

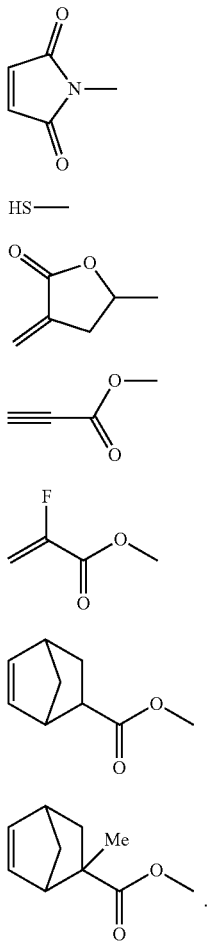

(P-14)
(P-15)
(P-16)
(P-17)
(P-18)
(P-19)
(P-20)

4. The method for producing a polymerizable compound according to claim 1,
wherein, in General Formula (I), $Sp^1$ and if present, $Sp^1$ each independently represent an alkylene group having 1 to 20 carbon atoms in which one —$CH_2$— or two or more non-adjacent —$CH_2$—'s may each independently be substituted with —O—, —COO—, —OCO—, —OCO—O—, —CO—NH—, —NH—CO—, —CH=CH—, or —C≡C—.

5. The method for producing a polymerizable compound according to claim 1,
wherein, in General Formula (I), M represents a group selected from Formula (M-1) to Formula (M-6):

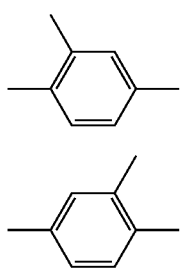

(M-1)
(M-2)

-continued

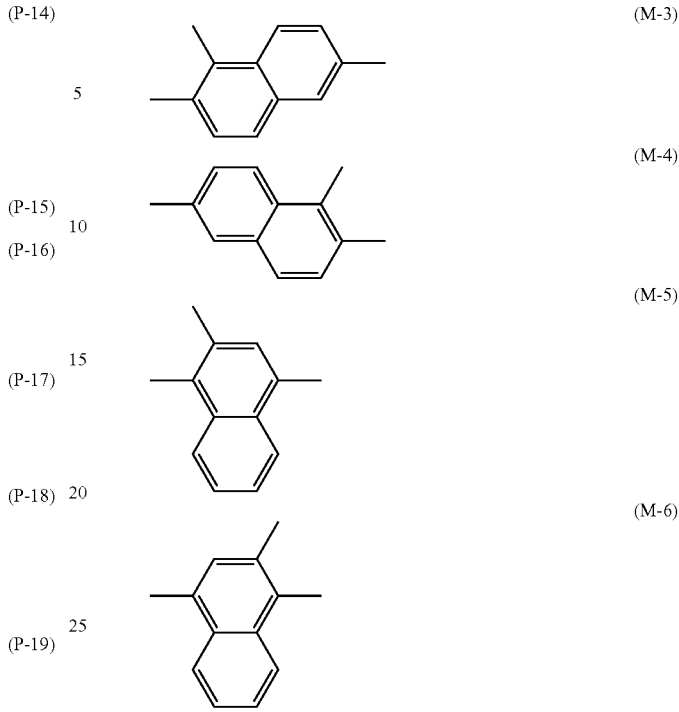

(M-3)
(M-4)
(M-5)
(M-6)

wherein these groups are unsubstituted or may be substituted with one or more substituents $L^M$ ($L^M$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more non-adjacent —$CH_2$—'s may each independently be substituted with —O—, —S—, —CO—, —OCO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, or $L^M$ may represent a group represented by $P^{LM}$—$(Sp^{LM}$-$X^{LM})_{kLM}$— where $P^{LM}$ represents a polymerizable group, and the polymerizable group is a group polymerizable by radical polymerization, radical addition polymerization, cationic polymerization, or anionic polymerization, Sp' represents a spacer group or a single bond, plural $Sp^{LM}$'s, if any, may be the same or different, $X^{LM}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, plural s, if any, may be the same or different, kLM represents an integer of 0 to 10, and plural $L^M$'s present in the compound, these $L^M$'s may be the same or different, and any —CH= may each independently be substituted with —N=.

* * * * *